US009822182B2

(12) United States Patent
Cizeau et al.

(10) Patent No.: US 9,822,182 B2
(45) Date of Patent: Nov. 21, 2017

(54) ANTI-EPCAM ANTIBODIES AND METHODS OF USE

(71) Applicant: Viventia Bio, Inc., Winnipeg (CA)

(72) Inventors: Jeannick Cizeau, Winnipeg (CA); Arjune Premsukh, Winnipeg (CA); Shilpa Chooniedass, Winnipeg (CA); Glen MacDonald, Winnipeg (CA); Joycelyn Entwistle, Winnipeg (CA)

(73) Assignee: VIVENTIA BIO INC., Winnipeg, Manitoba (CA)

( * ) Notice: Subject to any disclaimer, the term of this patent is extended or adjusted under 35 U.S.C. 154(b) by 37 days.

(21) Appl. No.: 15/026,834

(22) PCT Filed: Oct. 2, 2014

(86) PCT No.: PCT/CA2014/050950

§ 371 (c)(1),
(2) Date: Apr. 1, 2016

(87) PCT Pub. No.: WO2015/048901

PCT Pub. Date: Apr. 9, 2015

(65) Prior Publication Data

US 2016/0237164 A1 Aug. 18, 2016

Related U.S. Application Data

(60) Provisional application No. 62/030,805, filed on Jul. 30, 2014, provisional application No. 61/885,817, filed on Oct. 2, 2013.

(51) Int. Cl.

| | |
|---|---|
| ***C07K 16/30*** | (2006.01) |
| ***G01N 33/574*** | (2006.01) |
| ***A61K 47/48*** | (2006.01) |
| ***A61K 49/00*** | (2006.01) |
| ***A61K 45/06*** | (2006.01) |
| ***A61K 39/395*** | (2006.01) |

(52) U.S. Cl.

CPC ........ *C07K 16/30* (2013.01); *A61K 39/39558* (2013.01); *A61K 45/06* (2013.01); *A61K 47/48438* (2013.01); *A61K 47/48446* (2013.01); *A61K 47/48484* (2013.01); *A61K 47/48569* (2013.01); *A61K 49/0002* (2013.01); *G01N 33/574* (2013.01); *C07K 2317/24* (2013.01); *C07K 2317/55* (2013.01); *C07K 2317/56* (2013.01); *C07K 2317/92* (2013.01); *C07K 2319/55* (2013.01)

(58) Field of Classification Search

None

See application file for complete search history.

(56) References Cited

U.S. PATENT DOCUMENTS

| | | | |
|---|---|---|---|
| 5,082,767 | A | 1/1992 | Hatfield et al. |
| 5,690,928 | A | 11/1997 | Heimbrook et al. |
| 6,339,070 | B1 | 1/2002 | Emery et al. |
| 7,033,798 | B2 | 4/2006 | Pluckthun et al. |
| 7,339,031 | B2 | 3/2008 | Baker et al. |
| 7,341,722 | B2 | 3/2008 | Pluckthun et al. |
| 7,655,437 | B2 | 2/2010 | Jevsevar et al. |
| 7,858,088 | B2 | 12/2010 | Pluckthun et al. |
| 8,137,932 | B2 | 3/2012 | Pluckthun et al. |
| 8,263,744 | B2 * | 9/2012 | Cizeau ............ A61K 47/48438 424/130.1 |
| 8,318,472 | B2 | 11/2012 | Cizeau et al. |
| 8,545,840 | B2 | 10/2013 | Zangemeister-Wittke et al. |
| 9,259,484 | B2 | 2/2016 | Zangemeister-Wittke et al. |
| 2002/0146846 | A1 | 10/2002 | Pluckthun et al. |
| 2002/0193570 | A1 | 12/2002 | Gillies et al. |
| 2003/0148950 | A1 | 8/2003 | Xin et al. |
| 2004/0022726 | A1 | 2/2004 | Goldenberg et al. |
| 2005/0136049 | A1 | 6/2005 | Ledbetter et al. |
| 2007/0196366 | A1 | 8/2007 | Zangemeister-Wittke et al. |
| 2009/0081191 | A1 | 3/2009 | Kufer et al. |
| 2009/0171317 | A1 | 7/2009 | Versi |
| 2010/0215670 | A1 | 8/2010 | Cizeau et al. |
| 2010/0249039 | A1 | 9/2010 | Zangemeister-Wittke et al. |
| 2010/0310463 | A1 | 12/2010 | Gunnarsson et al. |
| 2011/0104062 | A1 | 5/2011 | Siu et al. |
| 2014/0178417 | A1 | 6/2014 | Zangemeister-Wittke et al. |
| 2014/0193436 | A1 | 7/2014 | Prudent et al. |
| 2016/0060352 | A1 | 3/2016 | Tanaka et al. |
| 2016/0199507 | A1 | 7/2016 | Zangemeister-Wittke et al. |

FOREIGN PATENT DOCUMENTS

| | | | |
|---|---|---|---|
| CA | 2424255 | A1 | 9/2004 |
| CA | 2560278 | A1 | 9/2005 |
| WO | WO 98/55623 | A1 | 12/1998 |
| WO | WO 99/65521 | A1 | 12/1999 |
| WO | WO 00/61635 | A2 | 10/2000 |

(Continued)

OTHER PUBLICATIONS

European Patent Application No. 14850812.0, Extended European Search Report dated Feb. 27, 2017, 9 pages.

(Continued)

*Primary Examiner* — Laura B Goddard
*Assistant Examiner* — Meera Natarajan
(74) *Attorney, Agent, or Firm* — Cooley LLP

(57) ABSTRACT

The present disclosure is related to compositions of antibodies and immunoconjugates that potentially lack T-cell epitopes and elicit reduced immune response. The antibody may be an antibody fragment, such as Fab, Fab', F(ab')2, scFv, dsFv, ds-scFv, dimers, minibodies, diabodies, bispecific antibody fragments, multimers, and any combination thereof. In a further embodiment, the antibody may bind to an antigen epithelial cell adhesion molecule (EpCAM). In another embodiment, an immunoconjugate may comprise an antibody attached to an effector molecule, wherein the effector molecule may be a radioisotope, an antineoplastic agent, an immunomodulator, a biological response modifier, lectin, a toxin, a chromophore, a fluorophore, a chemiluminescent compound, an enzyme, a metal ion, and any combination thereof.

29 Claims, 19 Drawing Sheets

(56) References Cited

FOREIGN PATENT DOCUMENTS

| | | | |
|---|---|---|---|
| WO | WO 00/69914 | A2 | 11/2000 |
| WO | WO 02/090566 | A2 | 11/2002 |
| WO | WO 03/033654 | A2 | 4/2003 |
| WO | WO 2004/096271 | A1 | 11/2004 |
| WO | WO 2005/090579 | A1 | 9/2005 |
| WO | WO 2005/121341 | A1 | 12/2005 |
| WO | WO 2008/128330 | A1 | 10/2008 |
| WO | WO 2009/039630 | A1 | 4/2009 |
| WO | WO 2010/115630 | A1 | 10/2010 |
| WO | WO 2011/116387 | A1 | 9/2011 |
| WO | WO 2014/166002 | A1 | 10/2014 |
| WO | WO 2015/048901 | A1 | 4/2015 |
| WO | WO 2016/145354 | A1 | 9/2016 |
| WO | WO 2017/040801 | A2 | 3/2017 |

OTHER PUBLICATIONS

Jones, Tim D., et al., "Deimmunization of Monoclonal Antibodies." Methods in Molecular Biology (2009); Chapter 21, 525: 405-423.

Schumann, et al., "Importance of Kupffer Cells for T-Cell-Dependent Liver Injury in Mice," American Journal of Pathology, 157(5):1672-1683 (2000).

Schumann, et al., "Acute Hepatotoxicity of Pseudomonas aeruginosa Exotoxin A in Mice Depends on T Cells and TNF," Journal of Immunology, 1661:5745-5754 (1998).

International Patent Application No. PCT/US2016/049932, International Search Report and Written Opinion dated Mar. 23, 2017, 12 pages.

Ma, Tianzhong, et al. "Human papillomavirus type 18 E6 and E7 genes integrate into human hepatoma derived cell line Hep G2." PloS One (2012); 7.5: e37964, pp. 1-9.

Al-Lazikani, B., et al. "Standard conformations for the canonical structures of immunoglobulins." J Mol Biol. Nov. 7, 1997; 273(4):927-48.

Apantaku, L.M., "Breast cancer diagnosis and screening." American Family Physician (2000); 62.3: 9 pages.

Azemar et al., "Recombinant antibody toxins specific for ErbB2 and EGF receptor inhibit the in vitro growth of human head and neck cancer cells and cause rapid tumor regression in vivo." International Journal of Cancer 86.2 (2000): 269-275.

Balzar et al., "The biology of the 17-1A antigen (Ep-CAM)." Journal of Molecular Medicine (1999); 77.10: 699-712.

Battelli et al., "Toxicity of ribosome-inactivating proteins-containing immunotoxins to a human bladder carcinoma cell line." Int J Cancer (1996); 65(4):485-490.

Bothmann and Plückthun, "Selection for a periplasmic factor improving phage display and functional periplasmic expression." Nat Biotechnol. (1998); 16(4):376-380.

Breuhahn et al., "Expression of epithelial cellular adhesion molecule (Ep-CAM) in chronic (necro-) inflammatory liver diseases and hepatocellular carcinoma." Hepatology Research (2006); 34.1: 50-56.

Carter and Merchant, "Engineering antibodies for imaging and therapy." Curr Opin Biotechnol. Aug. 1997; 8(4):449-54.

Carter, P., et al. "Humanization of an anti-p185HER2 antibody for human cancer therapy." Proc Natl Acad Sci U S A. May 15, 1992; 89(10):4285-9.

Casset et al., "A peptide mimetic of an anti-CD4 monoclonal antibody by rational design." Biochem Biophys Res Commun. (2003); 307(1):198-205.

Chatterjee, M.B., et al. "Idiotypic antibody immunotherapy of cancer." Cancer Immunol Immunother. Feb. 1994; 38 (2):75-82.

Chaubal et al., "Ep-CAM—a marker for the detection of disseminated tumor cells in patients suffering from SCCHN." Anticancer Research (1999); 19(3B): 2237-2242.

Chen et al., "Selection and analysis of an optimized anti-VEGF antibody: crystal structure of an affinity-matured fab in complex with antigen." J Mol Biol. (1999); 293(4): 865-881.

De Pascalis et al., "Grafting of "abbreviated" complementarity-determining regions containing specificity-determining residues essential for ligand contact to engineer a less immunogenic humanized monoclonal antibody." J. Immunol. (2002); 169(6): 3076-3084.

Dermer, G.B. "Another Anniversary for the war on Cancer." Bio/Technology. 1994; 12:320.

Di Paolo et al., "A recombinant immunotoxin derived from a humanized epithelial cell adhesion molecule-specific single-chain antibody fragment has potent and selective antitumor activity." Clin Cancer Res. (2003); 9(7): 2837-2848.

Eigenbrot, C., et al. "X-ray structures of the antigen-binding domains from three variants of humanized antip-185HER2 antibody 4D5 and comparison with molecular modeling." J Mol Biol. Feb. 20, 1993; 229(4):969-95.

European Patent Application No. 10011667.2, Extended European Search Report dated Sep. 29, 2011, 9 pages.

European Patent Application No. 14172801.4, Extended European Search Report dated Jan. 8, 2015, 11 pages.

Gherardi et al., "Structural basis of haptocyte growth factor/scatter factor and MET signalling." Proc. Nat. Acad. Sci. USA (2006); 103(11): 4046-4051.

Gibson, A.L., et al. "Differences in crystal properties and ligand affinities of an antifluorescyl Fab (4-4-20) in two solvent systems." Proteins. 1988; 3(3):155-60.

Glockshuber, R., et al. "A comparison of strategies to stabilize immunoglobulin Fv-fragments." Biochemistry. Feb. 13, 1990; 29(6):1362-7.

Gura, T. "Systems for identifying new drugs are often faulty." Science. Nov. 7, 1997; 278(5340):1041-2.

Helfrich, W., et al. "Construction and characterization of a bispecific diabody for retargeting T cells to human carcinomas." Int J Cancer. Apr. 13, 1998; 76(2):232-9.

Holm et al., "Functional mapping and single chain construction of the anti-cytokeratin 8 monoclonal antibody TS1." Mol Immunol. (2007); 44(6): 1075-1084. Epub Sep. 20, 2006.

International Patent Application No. PCT/EP/2000/003176, International Search Report dated Jan. 29, 2001, 3 pages.

International Patent Application No. PCT/CA2004/000637, International preliminary Report on Patentability dated Nov. 4, 2005, 10 pages.

International Patent Application No. PCT/CA2004/000637, International Search Report and Written Opinion dated Oct. 28, 2004, 15 pages.

International Patent Application No. PCT/CA2008/000711, International Preliminary Report on Patentability dated Oct. 20, 2009, 8 pages.

International Patent Application No. PCT/CA2008/000711, International Search Report and Written Opinion dated Aug. 8, 2008, 13 pages.

International Patent Application No. PCT/CA2008/001680, International Preliminary Report on Patentability dated Mar. 30, 2010, 8 pages.

International Patent Application No. PCT/CA2008/001680, International Search Report and Written Opinion dated Jan. 29, 2009, 11 pages.

International Patent Application No. PCT/CA2014/050373, International Search Preliminary Report on Patentability dated Oct. 13, 2015, 8 pages.

International Patent Application No. PCT/CA2014/050373, International Search Report and Written Opinion dated Jul. 11, 2014, 15 pages.

International Patent Application No. PCT/CA2014/050950, International Preliminary Report on Patentability dated Apr. 5, 2016, 9 pages.

International Patent Application No. PCT/CA2014/050950, International Search Report and Written Opinion dated Jan. 2, 2015, 15 pages.

International Patent Application No. PCT/US2016/022077, International Search Report and Written Opinion dated Jun. 10, 2016, 21 pages.

International Patent Application No. PCT/US2016/022085, International Search Report and Written Opinion dated Jun. 10, 2016, 20 pages.

(56) References Cited

OTHER PUBLICATIONS

Jain, R.K., et al. "Barriers to drug delivery in solid tumors." Sci Am. Jul. 1994; 271(1):58-65.
Jung and Plückthun, "Improving in vivo folding and stability of a single-chain Fv antibody fragment by loop grafting." Protein Eng. Aug. 1997; 10(8):959-66.
Kehoe and Capra. "Sequence relationships among the variable regions of immunoglobulin heavy chains from various mammalian species." PNAS USA (1972); 69(8): 2052-2055.
Kimura et al., "Characterization of the epithelial cell adhesion molecule (EpCAM)+ cell population in hepatocellular carcinoma cell lines." Cancer Science (2010); 101.10: 2145-2155.
Knappik and Plückthun, "Engineered turns of a recombinant antibody improve its in vivo folding." Protein Eng. Jan. 1995; 8 (1):81-9.
Kowalski et al., "A Phase I study of an intravesically administered immunotoxin targeting EpCAM for the treatment of nonmuscle-invasive bladder cancer in BCGrefractory and BCG-intolerant patients." Drug Des Devel Ther (2010); 4: 313-320.
Kowalski et al., "A phase II study of oportuzumab monatox: an immunotoxin therapy for patients with noninvasive urothelial carcinoma in situ previously treated with bacillus Calmette-Guerin." The Journal of Urology (2012); 188.5: 1712-1718.
Krebber, A., et al. "Reliable cloning of functional antibody variable domains from hybridomas and spleen cell repertoires employing a reengineered phage display system." J Immunol Methods. Feb. 14, 1997; 201(1):35-55.
Kreitman, "Immunotoxins in cancer therapy." Curr Opin Immunol. (1999); 11(5): 570-578.
Kubetzko and Zangemeister-Wittke, "Engineering of an EGP-2 (Ep-CAM) specific antibody-immunotoxin for targeted therapy of solid tumors." Swiss Cancer Bulletin (2000); 20(4): 182-187.
Langedijk, A.C., et al. "The nature of antibody heavy chain residue H6 strongly influences the stability of a VH domain lacking the disulfide bridge." J Mol Biol. 1998; 283(1):95-110.
LeMaistre et al., "An immunotoxin cytotoxic for breast cancer cells in vitro." Cancer Res. (1987); 47(3): 730-734.
MacCallum et al., "Antibody-antigen interactions: contact analysis and binding site topography." J Mol Biol. (1996); 262(5): 732-745.
Martin and Weber, "Genetic and hormonal risk factors in breast cancer." J Natl Cancer Inst. (2000); 92(14): 1126-1135.
McKiernan et al., "Phase I trial of intravesical docetaxel in the management of superficial bladder cancer refractory to standard intravesical therapy." Journal of Clinical Oncology (2006); 24.19: 3075-3080.
McLaughlin et al., "The epithelial glycoprotein 2 (EGP-2) promoter-driven epithelial-specific expression of EGP-2 in transgenic mice: a new model to study carcinoma-directed immunotherapy." Cancer Res. (2001); 61(10): 4105-4111.
Mueller et al., "Expression of tissue factor by melanoma cells promotes efficient hematogenous metastasis." Proc Natl Acad Sci USA (1992); 89(24): 11832-11836.
Ogawa et al., "EpCAM-targeted therapy for human hepatocellular carcinoma." Annals of Surgical Oncology (2014); 21.4: 1314-1322.
Oishi and Wang, "Novel therapeutic strategies for targeting liver cancer stem cells." Int J Biol Sci (2011); 7.5: 517-535.
Öelschläger et al., "Identification of factors impeding the production of a single-chain antibody fragment in *Escherichia coli* by comparing in vivo and in vitro expression." Applied Microbiology and Biotechnology (2003); 61.2: 123-132.
Pang and Poon, "Cancer stem cell as a potential therapeutic target in hepatocellular carcinoma." Current Cancer Drug Targets (2012); 12.9: 1081-1094.
Parker et al., "Optimization algorithms for functional deimmunization of therapeutic proteins." BMC Bioinformatics (2010); 11: 180, 15 pages.
Plückthun and Pack, "New protein engineering approaches to multivalent and bispecific antibody fragments." Immunotechnology. Jun. 1997; 3(2):83-105.
Proba, K., et al. "Antibody scFv fragments without disulfide bonds made by molecular evolution." J Mol Biol. Jan. 16, 1998; 275(2):245-53.
Rudikoff et al., "Single amino acid substitution altering antigen-binding specificity." Proc Natl Acad Sci USA (1982); 79(6): 1979-1983.
Saul, F.A. "Structural implications of VH sequence patterns." 55th Forum in Immunology, A Structural view of immune recognition by antibodies. Research in Immunology (1994); 145.1: 61-66.
Saul and Poljak, "Structural patterns at residue positions 9, 18, 67 and 82 in the VH framework regions of human and murine immunoglobulins." J Mol Biol. Mar. 5, 1993; 230(1):15-20.
Seaver. "Monoclonal Antibodies in Industry: More Difficult Than Originally Thought." Genetic Engineering News (1994); 14(14): 10 and 21.
Shan et al., "Angiogenesis and clinicopathologic characteristics in different hepatocellular carcinoma subtypes defined by EpCAM and α-fetoprotein expression status." Medical Oncology (2011); 28.4: 1012-1016.
Simon et al., "Epithelial cell adhesion molecule-targeted drug delivery for cancer therapy." Expert Opinion on Drug Delivery (2013); 10.4: 451-468.
Starling et al., "In vivo efficacy of monoclonal antibody-drug conjugates of three different sub isotypes which bind the human tumor-associated antigen defined by the KS1/4 monoclonal antibody." Cancer Immunol Immunother. (1989); 28(3): 171-178.
Stratagen Catalog (1988)(pp. 1-2).
Strome et al., "Interleukin 4 Receptor-directed Cytotoxin Therapy for Human Head and Neck Squamous Cell Carcinoma in Animal Models." Clin Cancer Res. (2002); 8(1): 281-286.
Syrigos et al., "Use of monoclonal antibodies for the diagnosis and treatment of bladder cancer." Hybridoma (1999); 18(3): 219-224.
Thiesen et al., "Selective killing of human bladder cancer cells by combined treatment with A and B chain ricin antibody conjugates." Cancer Res. (1987); 47(2): 419-423.
Vajdos et al., "Comprehensive functional maps of antigen-binding site of an anti-ErbB2 antibody obtained with shotgun scanning mutagenesis." J Mol Biol. (2002); 320(2): 415-428.
Velders et al., "The impact of antigen density and antibody affinity of antibody-dependent cellular cytotoxicity: relevance for immunotherapy of carcinomas." Br J Cancer (1998); 78(4): 478-483.
Waibel, R., et al. "Stable one-step technetium-99m labeling of His-tagged recombinant proteins with a novel Tc(I)-carbonyl complex." Nat Biotechnol. Sep. 1999; 17(9):897-901.
Wawrzynczak et al., "Pharmacokinetics in the rat of a panel of immunotoxins made with abrin A chain, ricin A chain, gelonin, and momordin." Cancer Res. (1990); 50(23): 7519-7526.
Willuda et al., "High thermal stability is essential for tumor targeting of antibody fragments: engineering of a humanized anti-epithelial glycoprotein-2 (epithelial cell adhesion molecule) single-chain Fv fragment." Cancer Res. (1999); 59(22): 5758-5767.
Willuda, J., et al. "Rational engineering for high stability is required for tumor targeting of a high-affinity scFv fragment specific for the panepithelial glycoprotein egp-2." Proceedings of the American Association for Cancer Research Annual Meeting (Mar. 1999), vol. 40, O. 354, Abst. 2343, Meeting Info,: 90th Annual Meeting of the American Association for Cancer Research, Philadelphia, PA, USA, Apr. 10-14, 1999.
Winter et al., "The Epithelial Cell Adhesion Molecule (Ep-CAM) as a Morphoregulatory Molecule Is a Tool in Surgical Pathology." Am J Pathol. (2003); 163(6): 2139-2148.
Wörn and Plückthun, "An intrinsically stable antibody scFv fragment can tolerate the loss of both disulfide bonds and fold correctly." FEBS Lett. (1998); 427(3): 357-361.
Wu et al., "Humanization of murine monoclonal antibody by simultaneous optimization of framework and CDR residues." J Mol Biol. (1999); 294(1): 151-162.
Yamashita et al., "EpCAM-positive hepatocellular carcinoma cells are tumor-initiating cells with stem/progenitor cell features." Gastroenterology (2009); 136.3: 1012-1024.

(56) References Cited

OTHER PUBLICATIONS

Zimmermann et al., "A novel immunotoxin recognising the epithelial glycoprotein-2 has potent antitumoural activity on chemotherapy-resistant lung cancer." Cancer Immunol Immunother. (1997); 44(1): 1-9.
Zorzos et al., "Expression of a cell surface antigen recognized by the monoclonal antibody AUA1 in bladder carcinoma: an immunohistochemical study." European Urology (1994); 28.3: 251-254.
Colombo, Federico, et al. "Evidence of distinct tumour-propagating cell populations with different properties in primary human hepatocellular carcinoma." PLoS One (2011); 6.6: e21369.
Entwistle, Joycelyn, et al. "Preclinical evaluation of VB6-845: an anti-EpCAM immunotoxin with reduced immunogenic potential." Cancer Biotherapy and Radiopharmaceuticals (2012); 27.9: 582-592.
European Patent Application No. 14782607.7, Extended European Search Report dated Nov. 16, 2016, 12 pages.
Wahl, Kristin, et al. "Increased apoptosis induction in hepatocellular carcinoma by a novel tumor-targeted Trail fusion protein combined with bortezomib." Hepatology (2013); 57.2: 625-636.

* cited by examiner

| | | Fold Increase (Mean ± S.E.) | |
|---|---|---|---|
| | Conc. (ng/mL) | Cal-27 | A-375 |
| VB5-845-DI | 7.8125 | 20.815 ± 0.0938 | 0.939 ± 0.00832 |
| | 31.25 | 64.363 ± 0.579 | 0.902 ± 0.0446 |
| | 125 | 204.543 ± 6.437 | 0.987 ± 0.0129 |
| VB5-845 WT | 7.8125 | 39.796 ± 1.253 | 0.940 ± 0.0416 |
| | 31.25 | 112.918 ± 0.509 | 0.961 ± 0.00454 |
| | 125 | 314.829 ± 1.416 | 0.978 ± 0.0129 |

FIG. 7

*GAA TTC* CTG CAG GTC TAT GGA ACG ATA AAT GCC CAT GAA AAT TCT ATT TCA AGG
*EcoRI*

AGA CAG TCA TA ATG AAA TAC CTA TTG CCT ACG GCA GCC GCT GGA TTG TTA TTA
M K Y L L P T A A A G L L L
PelB Leader Sequence CTC GCT GCC CAA CCA GCG ATG GCG GAA GTA CAG CTG GTC gaa TCC GGT ggt GGT
L A A Q P A M A E V Q L V E S G G G
$V_H$ Start
1 5 10

CTG GTT CAG CCG GGT GGT AGC ctg CGT ctg AGC TGC GCG GCG AGC GGT TAC
L V Q P G G S L R L S C A A S G Y
15 20 25

ACC TTC ACC gcg TAC GGT ATG AAC TGG GTT cgt CAG GCT CCG GGT AAA GGT TTG GAA
T F T A Y G M N W V R Q A P G K G L E
CDR 1
30 35 40 45

TGG ATG GGT TGG ATC AAC ACC TAT ACC GGT GAG TCT ACC TAC GCT GAT AGC gtt AAA
W M G W I N T Y T G E S T Y A D S V K
CDR 2
50 52a 55 60

GGC CGT TTC ACC atc AGC gct GAC ACT TCT aaa aac acc GCG TAC CTG CAG atg AAC
G R F T I S A D T S K N T A Y L Q M N
65 70 75 80 82a TCT CTG CGT GCT GAG GAC ACT GCG GTT TAC TAC TGC GCT CGT TTC GCG ATC AAA GGT
S L R A E D T A V Y Y C A R F A I K G
CDR3
82b 82c 85 90 95

GAC TAT TGG GGT CAG GGT ACT CTG gtt ACC GTT AGC AGC GCT AGC ACT AAG GGC CCG
D Y W G Q G T L V T V S S A S T K G P
$V_H$ End $C_H$ Start
101 105 110

TCC GTT TTC CCA CTG GCT CCG TCT TCT AAA AGC ACT TCT GGT GGT ACC GCG GCT CTG
S V F P L A P S S K S T S G G T A A L

GGT TGC CTT GTT AAA GAC TAC TTC CCT GAA CCG GTC ACC GTT AGC TGG AAC TCC GGT
G C L V K D Y F P E P V T V S W N S G

FIG. 11

```
GCG TTG ACC TCT GGT GTT CAC ACC TTC CCA GCG GTT CTG CAG TCT AGC GGT CTG TAT
 A   L   T   S   G   V   H   T   F   P   A   V   L   Q   S   S   G   L   Y

AGC CTG AGC TCT GTA GTT ACC GTT CCG TCT TCT AGC CTG GGT ACG CAG ACC TAC ATC
 S   L   S   S   V   V   T   V   P   S   S   S   L   G   T   Q   T   Y   I

TGC AAC GTG AAC CAC AAA CCG AGC AAC ACT AAA GTG GAT AAA AAA GTT GAA CCG AAG TCT
 C   N   V   N   H   K   P   S   N   T   K   V   D   K   K   V   E   P   K   S
                                                                     CH end ---

TGC TAG TAA TCT AGA GTC GAC CTG CAG GTC TAT GGA ACG ATA AAT GCC CAT GAA AAT TCT
 C
----|

ATT TCA AGG AGA CAG TCA TA ATG AAA TAC CTT CTG CCG ACC GCT GCC GCT GGT CTG CTG
                            M   K   Y   L   L   P   T   A   A   A   G   L   L
                           |_________________________PelB Leader Sequence ______

CTG TTG GCT GCT CAA CCG GCT ATG GCA GAC ATC CAG ATG ACC CAG TCC CCG TCT AGC CTG
 L   L   A   A   Q   P   A   M   A   D   I   Q   M   T   Q   S   P   S   S   L
___________________________________| |---------- VL Start
                                     1               5                   10

AGC GCA AGC GTT GGT GAC CGT GTG ACC ATC ACC TGC CGT AGC ACT AAA TCC CTG CTG CAC
 S   A   S   V   G   D   R   V   T   I   T   C   R   S   T   K   S   L   L   H
                                                |------------------------------
         15                  20                  25          27a 27b 27c 27d

TCT AAC GGC ATC ACC TAC CTG TAT TGG TAC CAA CAG AAA CCG GGT AAA GCT CCG AAA CTG
 S   N   G   I   T   Y   L   Y   W   Y   Q   Q   K   P   G   K   A   P   K   L
CDR 1 ------------------------|
27e      30                  35                  40                  45

CTG ATC TAC CAG ATG TCT AAC CTG GCT AGC GGC GTT CCT TCT CGT TTT TCT TCT AGC GGT
 L   I   Y   Q   M   S   N   L   A   S   G   V   P   S   R   F   S   S   S   G
            |-------- CDR 2 --------|
             50                  55                  60                  65

AGC GGT ACT GAC TTC ACC CTG ACC ATT AGC TCT CTG CAG CCT GAA GAC TTT GCG ACC TAC
 S   G   T   D   F   T   L   T   I   S   S   L   Q   P   E   D   F   A   T   Y
             70                  75                  80                  85

TAT TGC GCT CAG AAC CTT GAA ATC CCG CGT ACC TTC GGC acc GGT ACC AAA GTT GAA atc
 Y   C   A   Q   N   L   E   I   P   R   T   F   G   T   G   T   K   V   E   I
        |-------- CDR 3 --------|
             90                  95                 100                 105

AAG CGT ACC GTT GCG GCT CCG TCT GTT TTC ATC TTC CCA CCT AGC GAT GAA CAG CTT AAA
 K   R   T   V   A   A   P   S   V   F   I   F   P   P   S   D   E   Q   L   K
VL End ---| |--------- CL Start

TCT GGT ACT GCT AGC GTA GTT TGC CTG CTT AAC AAC TTC TAC CCT CGT GAA GCT AAA GTT
 S   G   T   A   S   V   V   C   L   L   N   N   F   Y   P   R   E   A   K   V
```

FIG. 11 continued

CAG TGG AAA GTT GAC AAC GCT CTG CAG TCT GGT AAC TCT CAG GAA TCT GTG ACC GAA
Q W K V D N A L Q S G N S Q E S V T E

CAG GAT AGC AAA GAT AGC ACC TAT AGC CTG TCT AGC ACC CTG ACC CTT AGC AAG GCG
Q D S K D S T Y S L S S T L T L S K A

GAC TAT GAA AAA CAC AAA GTT TAC GCT TGC GAG GTG ACC CAC CAA GGT CTG TCT TCT CCG
D Y E K H K V Y A C E V T H Q G L S S P

GTG ACT AAA TCC TTT AAC CGT GGC GAA TGC TAG TGA *CTC GAG*
V T K S F N R G E C *XhoI*
$C_L$ End -------|

FIG. 11 continued

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| $V_H$-WT | E | V | Q | L | V | Q | S | G | P | G | L | V | Q | P | G | G | S | V | R | I |
| $V_H$-deImmunized | E | V | Q | L | V | *E* | S | G | *G* | G | L | V | Q | P | G | G | S | *L* | R | *L* |

| | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| $V_H$-WT | S | C | A | A | S | G | Y | T | F | T | N | Y | G | M | N | W | V | K | Q | A |
| $V_H$-deImmunized | S | C | A | A | S | G | Y | T | F | T | *A* | Y | G | M | N | W | V | *R* | Q | A |

| | 41 | 42 | 43 | 44 | 45 | 46 | 47 | 48 | 49 | 50 | 51 | 52 | 52a | 53 | 54 | 55 | 56 | 57 | 58 | 59 |
|---|---|---|---|---|---|---|---|---|---|---|---|---|---|---|---|---|---|---|---|---|
| $V_H$-WT | P | G | K | G | L | E | W | M | G | W | I | N | T | Y | T | G | E | S | T | Y |
| $V_H$-deImmunized | P | G | K | G | L | E | W | M | G | W | I | N | T | Y | T | G | E | S | T | Y |

| | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|
| $V_H$-WT | A | D | S | F | K | G | R | F | T | F | S | L | D | T | S | A | S | A | A | Y |
| $V_H$-deImmunized | A | D | S | *V* | K | G | R | F | T | *I* | S | *A* | D | T | S | *K* | *N* | *T* | A | Y |

| | 80 | 81 | 82 | 82a | 82b | 82c | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|---|
| $V_H$-WT | L | Q | I | N | S | L | R | A | E | D | T | A | V | Y | Y | C | A | R | F | A |
| $V_H$-deImmunized | L | Q | *M* | N | S | L | R | A | E | D | T | A | V | Y | Y | C | A | R | F | A |

| | 97 | 98 | 99 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|
| $V_H$-WT | I | K | G | D | Y | W | G | Q | G | T | L | L | T | V | S | S |
| $V_H$-deImmunized | I | K | G | D | Y | W | G | Q | G | T | L | *V* | T | V | S | S |

FIG. 12

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| $V_L$-WT | D | I | Q | M | T | Q | S | P | S | S | L | S | A | S | V |
| $V_L$-deImmunized | D | I | Q | M | T | Q | S | P | S | S | L | S | A | S | V |

| | 16 | 17 | 18 | 19 | 20 | 21 | 22 | 23 | 24 | 25 | 26 | 27 | 27a | 27b | 27c |
|---|---|---|---|---|---|---|---|---|---|---|---|---|---|---|---|
| $V_L$-WT | G | D | R | V | T | I | T | C | R | S | T | K | S | L | L |
| $V_L$-deImmunized | G | D | R | V | T | I | T | C | R | S | T | K | S | L | L |

| | 27d | 27e | 28 | 29 | 30 | 31 | 32 | 33 | 34 | 35 | 36 | 37 | 38 | 39 | 40 |
|---|---|---|---|---|---|---|---|---|---|---|---|---|---|---|---|
| $V_L$-WT | H | S | N | G | I | T | Y | L | Y | W | Y | Q | Q | K | P |
| $V_L$-deImmunized | H | S | N | G | I | T | Y | L | Y | W | Y | Q | Q | K | P |

| | 41 | 42 | 43 | 44 | 45 | 46 | 47 | 48 | 49 | 50 | 51 | 52 | 53 | 54 | 55 |
|---|---|---|---|---|---|---|---|---|---|---|---|---|---|---|---|
| $V_L$-WT | G | K | A | P | K | L | L | I | Y | Q | M | S | N | L | A |
| $V_L$-deImmunized | G | K | A | P | K | L | L | I | Y | Q | M | S | N | L | A |

| | 56 | 57 | 58 | 59 | 60 | 61 | 62 | 63 | 64 | 65 | 66 | 67 | 68 | 69 | 70 |
|---|---|---|---|---|---|---|---|---|---|---|---|---|---|---|---|
| $V_L$-WT | S | G | V | P | S | R | F | S | S | S | G | S | G | T | D |
| $V_L$-deImmunized | S | G | V | P | S | R | F | S | S | S | G | S | G | T | D |

| | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|
| $V_L$-WT | F | T | L | T | I | S | S | L | Q | P | E | D | F | A | T |
| $V_L$-deImmunized | F | T | L | T | I | S | S | L | Q | P | E | D | F | A | T |

| | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|
| $V_L$-WT | Y | Y | C | A | Q | N | L | E | I | P | R | T | F | G | Q |
| $V_L$-deImmunized | Y | Y | C | A | Q | N | L | E | I | P | R | T | F | G | *T* |

| | 101 | 102 | 103 | 104 | 105 | 106 | 107 | 108 |
|---|---|---|---|---|---|---|---|---|
| $V_L$-WT | G | T | K | V | E | L | K | R |
| $V_L$-deImmunized | G | T | K | V | E | *I* | K | R |

FIG. 12 continued

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| $V_H$-MOCB | E | V | Q | L | V | Q | S | G | P | G | L | V | Q | P | G | G | S | V | R | I |
| $V_H$-Algo | E | V | Q | L | Q | Q | S | G | P | G | L | V | Q | P | G | G | S | V | R | I |

| | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| $V_H$-MOCB | S | C | A | A | S | G | Y | T | F | T | N | Y | G | M | N | W | V | K | Q | A |
| $V_H$-Algo | S | C | A | A | S | G | Y | T | F | T | A | Y | G | M | N | W | V | R | Q | A |

| | 41 | 42 | 43 | 44 | 45 | 46 | 47 | 48 | 49 | 50 | 51 | 52 | 52a | 53 | 54 | 55 | 56 | 57 | 58 | 59 |
|---|---|---|---|---|---|---|---|---|---|---|---|---|---|---|---|---|---|---|---|---|
| $V_H$-MOCB | P | G | K | G | L | E | W | M | G | W | I | N | T | Y | T | G | E | S | T | Y |
| $V_H$-Algo | P | G | K | G | L | E | W | M | G | W | I | N | T | Y | T | G | E | S | T | Y |

| | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|
| $V_H$-MOCB | A | D | S | F | K | G | R | F | T | F | S | L | D | T | S | A | S | A | A | Y |
| $V_H$-Algo | A | D | S | F | K | G | R | F | E | F | S | L | D | T | H | N | S | S | A | Y |

| | 80 | 81 | 82 | 82a | 82b | 82c | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|---|
| $V_H$-MOCB | L | Q | I | N | S | L | R | A | E | D | T | A | V | Y | Y | C | A | R | F | A |
| $V_H$-Algo | L | Q | I | Q | S | L | R | E | E | D | T | A | V | Y | Y | C | A | R | F | A |

| | 97 | 98 | 99 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|
| $V_H$-MOCB | I | K | G | D | Y | W | G | Q | G | T | L | L | T | V | S | S |
| $V_H$-Algo | I | K | G | D | Y | W | G | Q | G | T | L | V | T | V | S | S |

FIG. 17

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| $V_L$-MOCB | D | I | Q | M | T | Q | S | P | S | S | L | S | A | S | V |
| $V_L$-Algo | D | I | Q | M | T | Q | S | P | S | S | L | S | A | S | V |

| | 16 | 17 | 18 | 19 | 20 | 21 | 22 | 23 | 24 | 25 | 26 | 27 | 27a | 27b | 27c |
|---|---|---|---|---|---|---|---|---|---|---|---|---|---|---|---|
| $V_L$-MOCB | G | D | R | V | T | I | T | C | R | S | T | K | S | L | L |
| $V_L$-Algo | G | D | R | V | T | I | T | C | K | S | T | K | S | L | L |

| | 27d | 27e | 28 | 29 | 30 | 31 | 32 | 33 | 34 | 35 | 36 | 37 | 38 | 39 | 40 |
|---|---|---|---|---|---|---|---|---|---|---|---|---|---|---|---|
| $V_L$-MOCB | H | S | N | G | I | T | Y | L | Y | W | Y | Q | Q | K | P |
| $V_L$-Algo | H | S | N | G | I | T | Y | L | Y | W | Y | Q | Q | K | P |

| | 41 | 42 | 43 | 44 | 45 | 46 | 47 | 48 | 49 | 50 | 51 | 52 | 53 | 54 | 55 |
|---|---|---|---|---|---|---|---|---|---|---|---|---|---|---|---|
| $V_L$-MOCB | G | K | A | P | K | L | L | I | Y | Q | M | S | N | L | A |
| $V_L$-Algo | G | S | A | P | K | L | L | I | Y | Q | M | S | H | L | A |

| | 56 | 57 | 58 | 59 | 60 | 61 | 62 | 63 | 64 | 65 | 66 | 67 | 68 | 69 | 70 |
|---|---|---|---|---|---|---|---|---|---|---|---|---|---|---|---|
| $V_L$-MOCB | S | G | V | P | S | R | F | S | S | S | G | S | G | T | D |
| $V_L$-Algo | S | G | V | P | S | R | F | S | S | S | G | S | G | T | D |

| | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|
| $V_L$-MOCB | F | T | L | T | I | S | S | L | Q | P | E | D | F | A | T |
| $V_L$-Algo | F | T | L | T | I | S | S | L | Q | P | E | D | F | A | T |

| | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|
| $V_L$-MOCB | Y | Y | C | A | Q | N | L | E | I | P | R | T | F | G | Q |
| $V_L$-Algo | Y | Y | C | A | Q | N | L | E | I | P | R | T | F | G | Q |

| | 101 | 102 | 103 | 104 | 105 | 106 | 107 | 108 |
|---|---|---|---|---|---|---|---|---|
| $V_L$-MOCB | G | T | K | V | E | L | K | R |
| $V_L$-Algo | G | T | K | V | E | I | K | R |

FIG. 17 continued

ANTI-EPCAM ANTIBODIES AND METHODS OF USE

CROSS-REFERENCE TO RELATED APPLICATIONS

This application is a U.S. National phase application of International PCT Patent Application No. PCT/CA2014/050950, filed on Oct. 2, 2014, which claims priority to U.S. Provisional Application No. 61/885,817 filed on Oct. 2, 2013 and to U.S. Provisional Application No. 62/030,805 filed on Jul. 30, 2014, each of which are hereby incorporated by reference in their entireties.

BRIEF SUMMARY OF THE INVENTION

The present disclosure is related to antibodies and immunoconjugates that potentially lack T-cell epitopes and elicit reduced immune response. In one embodiment, an antibody may comprise a heavy chain having an amino acid sequence selected from SEQ ID NO: 1, SEQ ID NO: 11, SEQ ID NO: 31, or SEQ ID NO: 32; and a light chain having an amino acid sequence selected from SEQ ID NO: 2 or SEQ ID NO: 12. In some embodiments, the antibody may be an antibody fragment such as Fab, Fab', $F(ab')_2$, scFv, dsFv, ds-scFv, dimers, minibodies, diabodies, bispecific antibody fragments, non-immunoglobulin scaffolds, multimers, and any combination thereof. In a further embodiment, the antibody may bind to an antigen epithelial cell adhesion molecule (EpCAM). In additional embodiments, a composition may include the antibody described herein and a pharmaceutically acceptable excipient, carrier, buffer or stabilizer.

In another embodiment, an immunoconjugate may comprise an antibody (or fragment thereof) attached to an effector molecule, wherein the antibody may have a heavy chain with an amino acid sequence selected from SEQ ID NO: 1, SEQ ID NO: 11, SEQ ID NO: 31, or SEQ ID NO: 32; and a light chain with an amino acid sequence selected from SEQ ID NO: 2 or SEQ ID NO: 12. In other embodiments, the effector molecule may be a radioisotope, an antineoplastic agent, an immunomodulator, a biological response modifier, lectin, a toxin, a chromophore, a fluorophore, a chemiluminescent compound, an enzyme, a metal ion, and any combination thereof.

In an additional embodiment, a method of treating a subject with cancer may comprise administering a therapeutically effective amount of an immunoconjugate comprising an antibody attached to an effector molecule, wherein the antibody comprises a heavy chain having an amino acid sequence selected from SEQ ID NO: 1, SEQ ID NO: 11, SEQ ID NO: 31, or SEQ ID NO: 32; and a light chain having an amino acid sequence selected from SEQ ID NO: 2 or SEQ ID NO: 12. In some embodiments, the effector molecule may be radioisotopes, antineoplastic agents, immunomodulators, biological response modifiers, lectins, toxins, a chromophore, a fluorophore, a chemiluminescent compound, an enzyme, a metal ion, and any combination thereof. In certain embodiments, the method may further comprise detecting or imaging the immunoconjugate in the subject. In further embodiments, the method may further comprise removing cancerous tissue from the subject that is detected or imaged.

In a further embodiment, a method of diagnosing, detecting or monitoring cancer in a subject may comprise contacting a test sample taken from said subject with an antibody to form an antibody-antigen complex, wherein the antibody comprises a heavy chain amino acid sequence selected from SEQ ID NO: 1, SEQ ID NO: 11, and a light chain having amino acid sequence selected from SEQ ID NO: 2 and SEQ ID NO: 12; measuring the amount of antibody-antigen complex in the test sample; and normalizing the results against a control is provided.

In another embodiment, a method of diagnosing, detecting or monitoring cancer in a subject may involve administering to the subject an antibody comprising a heavy chain having an amino acid sequence selected from SEQ ID NO: 1, SEQ ID NO: 11, SEQ ID NO: 31, or SEQ ID NO: 32; and a light chain having an amino acid sequence selected from SEQ ID NO: 2 or SEQ ID NO: 12; and detecting the antibody in the subject.

In another embodiment, a kit for diagnosing, detecting, or monitoring cancer may include an antibody having a heavy chain amino acid sequence selected from SEQ ID NO: 1, SEQ ID NO: 11, SEQ ID NO: 31, or SEQ ID NO: 32; and a light chain having amino acid sequence selected from SEQ ID NO: 2 or SEQ ID NO: 12, and instructions for the use thereof.

In another embodiment, a method of imaging a tumor in a subject may involve administering to the subject an antibody comprising a heavy chain having an amino acid sequence selected from SEQ ID NO: 1, SEQ ID NO: 11, SEQ ID NO: 31, or SEQ ID NO: 32; and a light chain having an amino acid sequence selected from SEQ ID NO: 2 or SEQ ID NO: 12; and detecting the antibody by in vivo imaging.

DESCRIPTION OF DRAWINGS

FIG. 7 displays binding specificity of VB5-845-DI and VB5-845-WT against EpCAM-positive Cal-27 and EpCAM-negative A-375, as measured by flow cytometry.

FIG. 11 depicts the nucleotide and amino acid sequence of VB5-845-DI.

FIG. 12 shows alignment of $V_H$ and $V_L$ domains of VB5-845-WT and VB5-845-DI, with Kabat numbering.

FIG. 17 shows alignment of $V_H$ and $V_L$ domains of VB5-845-WT and VB5-845 Algo, with Kabat numbering.

DETAILED DESCRIPTION

Figure 1:
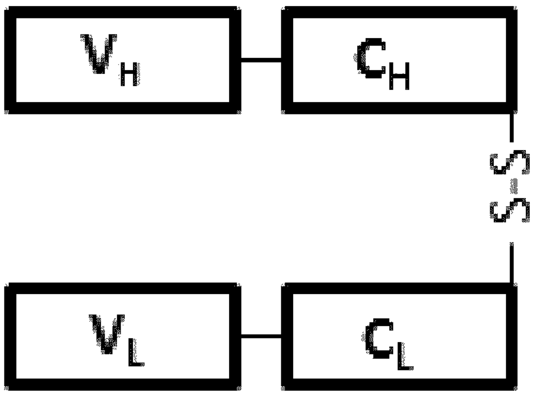
FIG. 1 is a schematic of an embodiment of the present invention, in particular de-immunized VB5-845 Fab fragment (VB5-845-DI), as well as VB5-845 non-de-immunized Fab fragment (VB5-845-WT).
Figure 2:
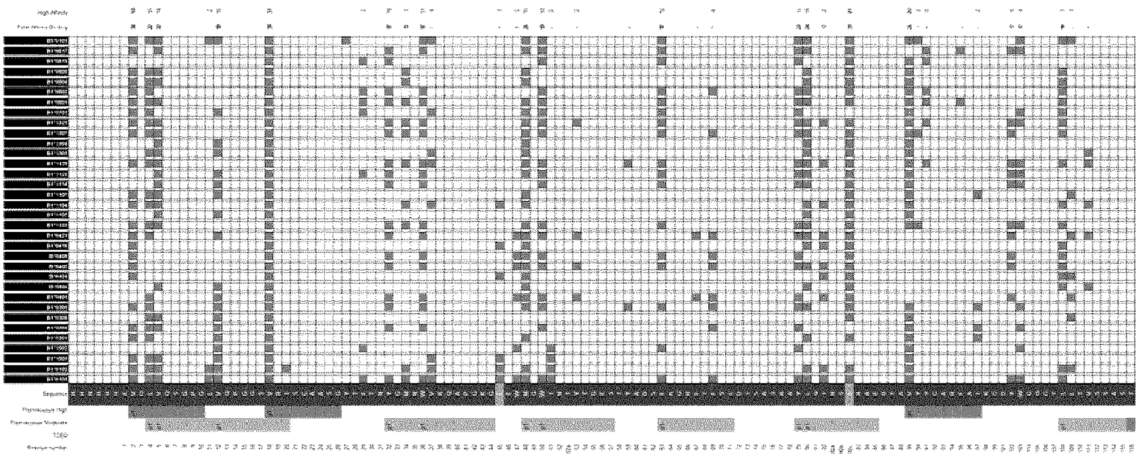
FIG. 2 shows the analysis of sequence $V_H$-WT ($V_H$-wild type) using iTope™. Regions containing potentially immunogenic peptides are indicated in the "Promiscuous High" and "Promiscuous Moderate" rows.
Figure 3:
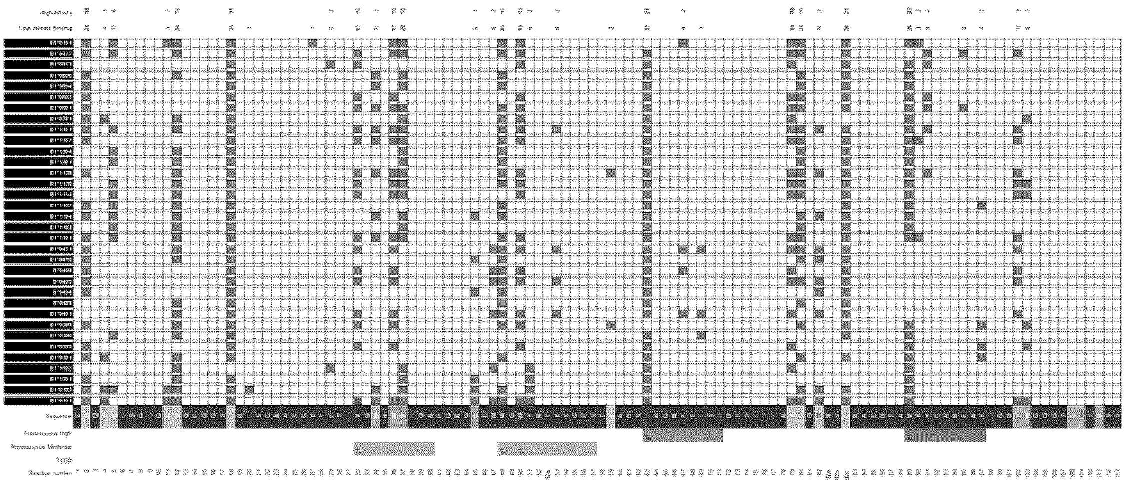
FIG. 3 shows analysis of sequence $V_H$-DI ($V_H$-deimmunized) using iTope™. Regions containing potentially immunogenic peptides are indicated in the "Promiscuous High" and "Promiscuous Moderate" rows.
Figure 4:
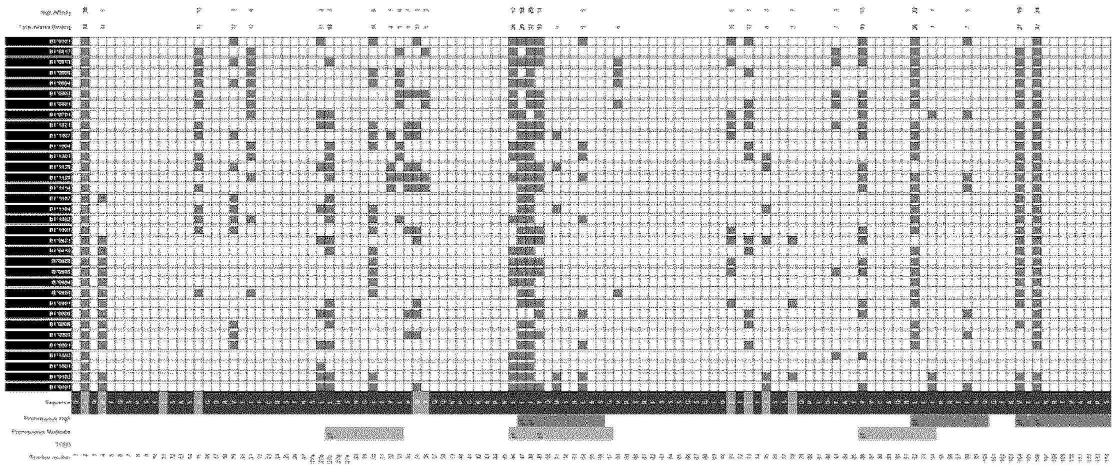
FIG. 4 shows analysis of sequence $V_L$-WT ($V_L$-wild-type) using iTope™. Regions containing potentially immunogenic peptides are indicated in the "Promiscuous High" and "Promiscuous Moderate" rows.
Figure 5:
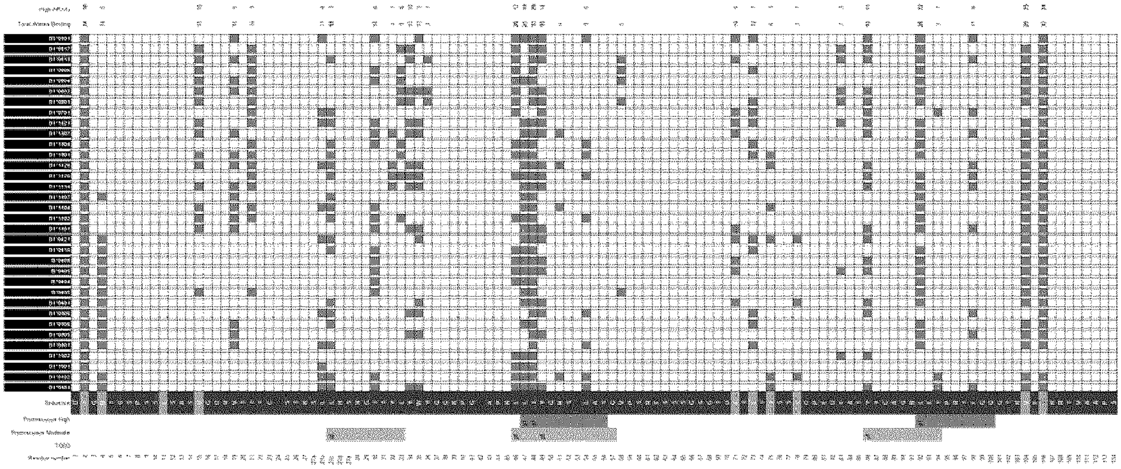
FIG. 5 shows analysis of sequence $V_L$-DI ($V_L$-deimmunized) using iTope™. Regions containing potentially immunogenic peptides are indicated in the "Promiscuous High" and "Promiscuous Moderate" rows.
Figure 6:
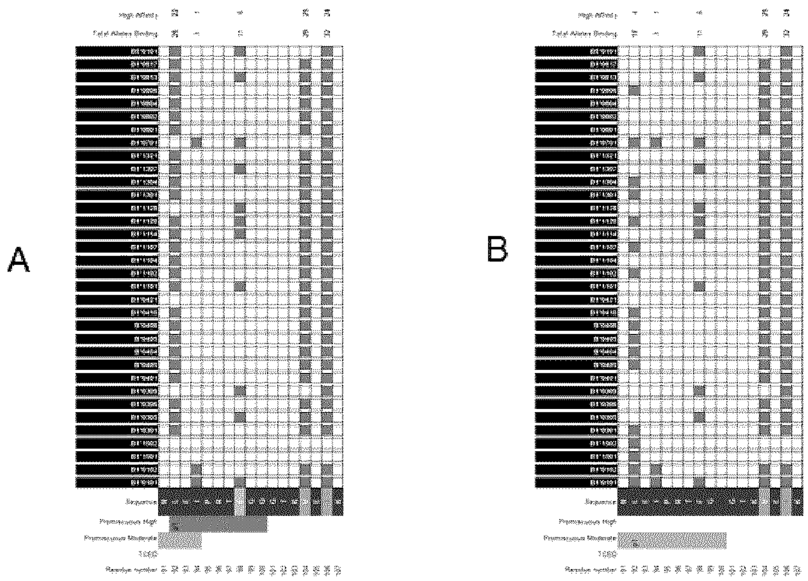
FIG. 6 shows analysis of sequences $V_L$-DI and $V_L$-DIF ($V_L$-DI plus additional C-terminal) spanning the single amino acid change using iTope™.

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. Nothing herein is to be construed as an admission that the invention is not entitled to antedate such disclosure by virtue of prior invention.

Singular forms "a", "an", and "the" include plural reference unless the context clearly dictates otherwise. Thus, for example, reference to an "antioxidant" is a reference to one or more antioxidants and equivalents thereof known to those skilled in the art, and so forth.

The term "about" means plus or minus 10% of the numerical value of the number with which it is being used. Therefore, about 50% means in the range of 45%-55%.

The term "animal," "patient," or "subject" as used herein includes, but is not limited to, humans and non-human vertebrates such as wild, domestic and farm animals.

"Antibody fragments" that may be used include Fab, Fab', F(ab')2, scFv, dsFv, ds-scFv, dimers, minibodies, diabodies, bispecific antibody fragments, multimers, and any combination thereof, and fragments from recombinant sources and/or produced in transgenic animals. The antibody or fragment may be from any species including mice, rats, rabbits, hamsters and humans. Chimeric antibody derivatives, i.e., antibody molecules that combine a non-human animal variable region and a human constant region are also contemplated within the scope of the invention. Chimeric antibody molecules can include, for example, humanized antibodies which comprise the antigen binding domain from an antibody of a mouse, rat, or other species, with human constant regions. Conventional methods may be used to make chimeric antibodies. It is expected that chimeric antibodies would be less immunogenic in a human subject than the corresponding non-chimeric antibody. The humanized antibodies can be further stabilized for example as described in WO 00/61635 and is incorporated by reference in its entirety.

"Anticancer agents" refers to compounds or treatments that are effective in treating or preventing cancer including, without limitation, chemical agents, other immunotherapeutics, cancer vaccines, anti-angiogenic compounds, certain cytokines, certain hormones, gene therapy, radiotherapy, surgery, and dietary therapy.

"De-immunized" refers to a molecule that lacks or elicits reduced immune response when compared to the wild type counterpart.

"De-immunized antibodies" or "de-immunized antibody fragments" refers to antibodies and antibody fragments that lack one or more T-cell epitopes and elicit reduced immune response when compared to the wild type counterpart.

"De-immunized VB5-845" refers to Fab fragment of EpCAM antibody wherein the putative T-cell epitopes on the $V_H$ domain and the $V_L$ domain are mutated and might result in eliciting a reduced immune response when compared to the non-deimmunized Fab fragment VB5-845 (VB5-845-WT). De-immunized VB5-845 Fab fragment (VB5-845-DI) comprises a de-immunized $V_H$-$C_H$ domain (SEQ ID NO: 1) and a de-immunized $V_L$-$C_L$ domain (SEQ ID NO: 2). The non-deimmunized VB5-845 Fab fragment (VB5-845-WT) comprises a wild type $V_H$-$C_H$ domain (SEQ ID NO: 5) and a wild type $V_L$-$C_L$ domain (SEQ ID NO: 6).

"Effective amount" or "therapeutically effective amount" means an amount effective, at dosages and for periods of time necessary to achieve the desired result. Effective amounts of an immunoconjugate may vary according to factors such as the disease state, age, sex, weight of the animal. Dosage regimen may be adjusted to provide the optimum therapeutic response. For example, several divided doses may be administered daily or the dose may be proportionally reduced as indicated by the exigencies of the therapeutic situation.

"Humanized antibody or antibody fragment" means that the antibody or fragment comprises human framework regions.

"Immunoconjugate" refers to an antibody or fragment thereof conjugated to an effector molecule. In some embodiments, the antibody may be full length antibody or antibody fragments, such as Fab, Fab', F(ab')2, scFv, dsFv, ds-scFv, dimers, minibodies, diabodies, bispecific antibody fragments, multimers, and any combination thereof, and fragments from recombinant sources and/or produced in transgenic animals. In some embodiments, the antibody may be a synthetic protein, a binding protein or a polypeptide. In some embodiments, the effector molecule may be a toxin, a radionucleotide, a radiopharmaceutical, a labeling agent, a drug, a cytotoxic agent, a peptide, a protein and the like. These effector molecules may be capable of killing, lysing or labeling or inducing other effects when the antibody binds to an antigen.

"Reduced propensity to elicit an immune response" as used herein means that the modified EpCAM antibody or the antibody fragment is less immunogenic than non-modified EpCAM antibody.

"Immune response" includes both cellular and humoral immune responses.

The term "is administered directly to the cancer site" refers to direct or substantially direct introduction including, without limitation, single or multiple injections of the immunoconjugate directly into the tumor or peritumorally, continuous or discontinuous perfusion into the tumor or peritumorally, introduction of a reservoir into the tumor or peritumorally, introduction of a slow-release apparatus into the tumor or peritumorally, introduction of a slow-release formulation into the tumor or peritumorally, direct application onto the tumor, direct injection into an artery that substantially directly feeds the area of the tumor, direct injection into a lymphatic vessel that substantially drains into the area of the tumor, direct or substantially direct introduction in a substantially enclosed cavity (e.g., pleural cavity) or lumen (e.g., intravesicular). "Peritumoral" is a term that describes a region, within about 10 cm, preferably within 5 cm, more preferably within 1 cm, of what is regarded as the tumor boundary, such as, but not limited to, a palpable tumor border. "Direct administration" in the context of prevention of occurrence or prevention of recurrence is defined as administration directly into a site at risk for development or recurrence of a cancer.

"Pharmaceutically acceptable" refers to general clinical use and/or approval by a regulatory agency of the Federal or state government, listing in the United States Pharmacopoeia, or general acceptance by those skilled in the relevant art.

"Physiologic conditions" for antibody binding reflect but do not necessarily exactly duplicate the conditions in which an EpCAM-binding polypeptide would encounter an EpCAM molecule in vivo. Binding under physiologic conditions should be reasonably predictive that binding in vivo will occur.

"Preventing cancer" refers to prevention of cancer occurrence. In certain instances, the preventative treatment reduces the recurrence of the cancer. In other instances, preventative treatment decreases the risk of a patient from developing a cancer, or inhibits progression of a pre-cancerous state (e.g. a colon polyp) to actual malignancy.

"Reduced dose" refers to a dose that is below the normally administered and/or recommended dose. The normally administered dose of an anticancer agent can be found in reference materials well known in the art such as, for example, the latest edition of the Physician's Desk Reference.

"Treating cancer" refers to inhibition of cancer cell replication, apoptosis, inhibition of cancer spread (metastasis), inhibition of tumor growth, reduction of cancer cell number or tumor growth, decrease in the malignant grade of a cancer (e.g., increased differentiation), or improved cancer-related symptoms.

"Therapeutic" means an agent utilized to discourage, combat, ameliorate, prevent or improve an unwanted condition, disease or symptom of a patient.

"Variant" refers to any pharmaceutically acceptable derivative, analogue, or fragment of an immunoconjugate, an antibody or antibody fragment, a toxin (e.g., *Pseudomonas* toxin), or an effector molecule described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting embodiments, an immunoconjugate may be a "variant" relative to a reference immunoconjugate by virtue of alteration(s) in the EpCAM-binding portion and/or the toxin portion of the reference immunoconjugate. For example, a variant immunoconjugate may contain multimers of the antibody portion and/or the toxin portion. A variant of the toxin portion of the molecule retains toxicity of at least 10%, at least 30%, at least 50%, at least 80%, at least 90%, in a standard assay used to measure toxicity of a preparation of the reference toxin. In some embodiments, a variant may also refer to polypeptides having at least 50%, at least 60%, at least 70%, at least 80%, at least 90%, or 95% sequence identity to the immunoconjugate of the present invention. In some embodiments, a variant antibody may refer to polypeptides or proteins having at least 30%, at least 60%, at least 70%, at least 80%, at least 90%, or 95% sequence identity of the antibody of the present invention. In some embodiments, a variant antibody or the immnunoconjugate may refer to polypeptides or proteins having at least 30%, at least 60%, at least 70%, at least 80%, at least 90%, or 95% binding affinity of the antibody of the present invention when measured by a competitive binding assay.

A variant immunoconjugate having a variation of the EpCAM-binding portion of the reference immunoconjugate competes with the binding of an anti-EpCAM reference antibody, under physiologic conditions, by at least 10 percent and preferably at least 30 percent (and see infra). Competition by 10 percent means that, in an assay where a saturating concentration of anti-EpCAM reference antibody is bound to EpCAM, 10 percent of these bound reference antibodies is displaced when equilibrium is reached with an equivalent concentration of the variant anti-EpCAM immunoconjugate. As a non-limiting example, competition between antibodies, or between an antibody and an immunoconjugate, is measured by binding labeled anti-EpCAM reference antibody to EpCAM on the surface of cells or to an EpCAM-coated solid substrate, such that virtually all EpCAM sites are bound by the antibody, contacting these antibody-antigen complexes with unlabeled test anti-EpCAM antibody or unlabeled test immunoconjugate, and measuring the amount of labeled antibody displaced from EpCAM binding sites, wherein the amount of freed, labeled antibody indicates the amount of competition that has occurred.

"VB5-845" refers to a Fab fragment of EpCAM antibody without toxin conjugate.

"VB6-845" refers to a Fab fragment of EpCAM antibody genetically linked to a modified bouganin protein (deBouganin) toxin.

"4D5MOC-B" or "4D5" means the humanized scFv MOC31 antibody grafted onto the artificial human consensus framework of scFv 4D5 as described in WO 00/61635 which is incorporated herein by reference in its entirety. 4D5MOC-B is represented by SEQ ID NO: 8. "MOC-31 antibody" means the murine anti-EpCAM or anti-EGP-2 antibody and is available from commercial sources such as BioGenex, Cat No. MU316-UC, Zymed Laboratories Inc., Cat No. 18-0270 or United States Biological, Cat No. M4165.

Immunotherapy has emerged as a powerful tool to combat cancer. Murine and humanized/chimeric antibodies, and their respective antibody fragments, directed against tumor-associated antigens ("TAAs") have been used for diagnosis and therapy of certain human cancers. Unconjugated, toxin-conjugated, and radiolabeled forms of these antibodies have been used in such therapies.

One tumor associated antigen of interest for immunotherapy is Epithelial Cell Adhesion Molecule (EpCAM) which is also known as 17-1 A, KSA, EGP-2 and GA733-2. EpCAM is a transmembrane protein that is highly expressed in many solid tumors, including carcinomas of the lung, breast, ovary, colorectal, and squamous cell carcinoma of the head and neck, but weakly expressed in most normal epithelial tissues. Its expression correlates with the rate of cellular proliferation. EpCAM-specific antibodies have been used to image and detect primary tumors and metastases in patients with small cell lung cancer and non-small cell lung cancer.

There are many instances whereby the efficacy of a therapeutic protein is limited by an unwanted immune reaction to the therapeutic protein. Several mouse monoclonal antibodies have shown promise as therapies in a number of human disease settings, but in certain cases, have failed due to the induction of significant degrees of a human anti-murine antibody (HAMA) response. For monoclonal antibodies, a number of techniques have been developed in attempt to reduce the HAMA response. These recombinant DNA approaches have generally reduced the mouse genetic information in the final antibody construct whilst increasing the human genetic information in the final construct. Notwithstanding, the resultant "humanized" antibodies have, in several cases, still elicited an immune response in patients.

The key to the induction of an immune response is the presence within the protein of peptides that can stimulate the activity of T-cells via presentation on MHC class II molecules, so-called "T-cell epitopes". Such T-cell epitopes are commonly defined as any amino acid residue sequence with the ability to bind to MHC Class II molecules. Implicitly, a "T-cell epitope" means an epitope, which when bound to MHC molecules, can be recognized by a T-cell receptor (TCR), and which can, at least in principle, cause the activation of these T-cells by engaging a TCR to promote a T-cell response. Thus, it is desirable to identify and to remove T-cell epitopes from antibodies and antibody fragments and to develop better antibody/antibody fragments that elicit reduced immune response.

Antibodies

Disclosed herein are de-immunized antibodies and de-immunized antibody fragments that bind to a cancer cell antigen. In some embodiments, the antigen may be EpCAM. In some embodiments, the antibody may have a heavy chain with an amino acid sequence of SEQ ID NO: 1, SEQ ID NO: 11, SEQ ID NO: 31, or SEQ ID NO: 32; and a light chain with an amino acid sequence of SEQ ID NO: 2 or SEQ ID NO: 12. The antibody may be full length antibody or antibody fragments, such as Fab, Fab', $F(ab')_2$, scFv, dsFv, ds-scFv, dimers, minibodies, diabodies, bispecific antibody fragments, multimers, and any combination thereof.

In some embodiments, the antibodies described herein may have a heavy chain with an amino acid sequence of SEQ ID NO: 1, and a light chain with an amino acid sequence of SEQ ID NO: 2. In some embodiments, the antibodies described herein may have a heavy chain with an amino acid sequence of SEQ ID NO: 11, and a light chain with an amino acid sequence of SEQ ID NO: 12. In some embodiments, the antibodies described herein may have a heavy chain with an amino acid sequence of SEQ ID NO: 1, and a light chain with an amino acid sequence of SEQ ID NO: 12. In some embodiments, the antibodies described herein may have a heavy chain with an amino acid sequence of SEQ ID NO: 11, and a light chain with an amino acid sequence of SEQ ID NO: 2. In some embodiments, the antibodies described herein may have a heavy chain with an amino acid sequence of SEQ ID NO: 31, and a light chain with an amino acid sequence of SEQ ID NO: 2. In some embodiments, the antibodies described herein may have a heavy chain with an amino acid sequence of SEQ ID NO: 31, and a light chain with an amino acid sequence of SEQ ID NO: 12. In some embodiments, the antibodies described herein may have a heavy chain with an amino acid sequence of SEQ ID NO: 32, and a light chain with an amino acid sequence of SEQ ID NO: 2. In some embodiments, the antibodies described herein may have a heavy chain with an amino acid sequence of SEQ ID NO: 32, and a light chain with an amino acid sequence of SEQ ID NO: 12.

In some embodiments, the sequences of the light chain and the heavy chain fragments may be modified or replaced with other amino acids such that the antibody elicits reduced immune response in humans. For making humanized antibody or antibody fragments, any method known in the art may be used. For example, human antibody fragments can be obtained by screening human antibody libraries. Another solution is to transplant the specificity of a non-human monoclonal antibody by grafting the CDR regions onto a human framework. In an improvement of said technique, humanized antibodies or antibody fragments with improved binding behavior can be produced by incorporating additional residues derived from said non-human antibody. In addition to achieving humanization, techniques to "repair" antibody fragments with suboptimal stability and/or folding or yield may be used by grafting the CDRs of a scFv fragment with the desired binding affinity and specificity onto the framework of a different, better behaved scFv. Such methods for making humanized antibodies or antibody fragments are well known in the art and include, by way of example, production in SCID mice, and in vitro immunization.

In some embodiments, the antibody fragment may be Fab, and the light chain and the heavy chain are linked by a covalent bond. In some embodiments, the covalent linkage may be disulfide bond. In some embodiments, the covalent linkage may be through chemical crosslinkers, such as dimethyl adipimidate, dimethyl suberimidate, and the like. In some embodiments, amino acid crosslinkers, such as $(Gly_4\text{-}Ser)_n$ may be used. The sequences of the light chain and the heavy chain described herein may be used to derive scFv, diabodies, tribodies, tetrabodies, and the like. Various protein linking strategies may be used to produce bivalent or bispecific Fab and scFvs, as well as bifunctional Fab and scFv fusions.

The antibody fragments described herein may be cloned and expressed in *E. coli* in a biologically functional form. Antibodies and antibody fragments may also be produced by recombinant DNA technology using either bacterial or mammalian cells.

In some embodiments, affinity maturation process may be used whereby the binding specificity, affinity or avidity of the antibody described herein can be modified. A number of laboratory techniques have been devised whereby amino acid sequence diversity is created by the application of various mutation strategies, either on the entire antibody fragment or on selected regions such as the CDRs.

In some embodiments, the variant amino acid sequences of the heavy chain and the light chain have at least 50%, preferably at least 60%, more preferably at least 70%, most preferably at least 80%, even more preferably at least 90%, and even most preferably 95% sequence identity to SEQ ID NOS: 1 and 2, respectively. In other embodiments, the variant amino acid sequences of the heavy chain and the light chain have at least 50%, preferably at least 60%, more preferably at least 70%, most preferably at least 80%, even more preferably at least 90%, and even most preferably 95% sequence identity to SEQ ID NOS: 11 and 12, respectively.

Immunoconjugates

In some embodiments, immunoconjugates are provided. In some embodiments, the immunoconjugate disclosed herein may be an antibody attached to an effector molecule, wherein the antibody comprises a heavy chain having an amino acid sequence of SEQ ID NO: 1, SEQ ID NO: 11, SEQ ID NO: 31, or SEQ ID NO: 32; and a light chain having an amino acid sequence of SEQ ID NO: 2 or SEQ ID NO: 12. In some embodiments, the antibody may be an antibody fragment, such as Fab, Fab', $F(ab')_2$, scFv, dsFv, ds-scFv, dimers, minibodies, diabodies, bispecific antibody fragments, multimers, and any combination thereof. The antibody or the antibody fragment may be any of the de-immunized antibodies or de-immunized antibody fragments disclosed herein.

In some embodiments, the antibody in the immunoconjugate may have a heavy chain with an amino acid sequence of SEQ ID NO: 1, and a light chain with an amino acid sequence of SEQ ID NO: 2. In some embodiments, the antibody in the immunoconjugate may have a heavy chain with an amino acid sequence of SEQ ID NO: 11, and a light chain with an amino acid sequence of SEQ ID NO: 12. In some embodiments, the antibody in the immunoconjugate may have a heavy chain with an amino acid sequence of SEQ ID NO: 1, and a light chain with an amino acid sequence of SEQ ID NO: 12. In some embodiments, the antibody in the immunoconjugate may have a heavy chain with an amino acid sequence of SEQ ID NO: 11, and a light chain with an amino acid sequence of SEQ ID NO: 2. In some embodiments, the antibodies described herein may have a heavy chain with an amino acid sequence of SEQ ID NO: 31, and a light chain with an amino acid sequence of SEQ ID NO: 2. In some embodiments, the antibodies described herein may have a heavy chain with an amino acid sequence of SEQ ID NO: 31, and a light chain with an amino acid sequence of SEQ ID NO: 12. In some embodiments, the antibodies described herein may have a heavy chain with an amino acid sequence of SEQ ID NO: 32, and a light chain with an amino acid sequence of SEQ ID NO: 2. In some embodiments, the antibodies described herein may have a heavy chain with an amino acid sequence of SEQ ID NO: 32, and a light chain with an amino acid sequence of SEQ ID NO: 12.

In the embodiments described herein, the effector molecule may be radioisotopes, antineoplastic agents, immunomodulators, biological response modifiers, lectins, toxins, a chromophore, a fluorophore, a chemiluminescent compound, an enzyme, a metal ion, and any combination thereof. In some embodiments, the effector molecule may be a toxin, such as abrin, modeccin, viscumin, gelonin, bouganin, modified or de-immunized bouganin protein (deBouganin), saporin, ricin, ricin A chain, bryodin, luffin, momordin, restrictocin, *Pseudomonas* exotoxin A, pertussis toxin, tetanus toxin, botulinum toxin, *Shigella* toxin, cholera toxin, diphtheria toxin and any combination thereof. In embodiments, the toxin may be deBouganin as shown in SEQ ID NO: 4, SEQ ID NO: 9, SEQ ID NO: 33, SEQ ID NO: 42, or SEQ ID NO: 43. In embodiments, the toxin may be *Pseudomonas* exotoxin A as shown in SEQ ID NO: 3.

In other non-limiting embodiments, the toxin comprises an agent that acts to disrupt DNA. Thus, toxins may be, without limitation, enediynes (e.g., calicheamicin and esperamicin) and non-enediyne small molecule agents (e.g., bleomycin, methidiumpropyl-EDTA-Fe(II)). Other toxins useful in accordance with the invention include, without limitation, daunorubicin, doxorubicin, distamycin A, cisplatin, mitomycin C, ecteinascidins, duocarmycin/CC-1065, and bleomycin/pepleomycin. In other non-limiting embodiments, the toxin comprises an agent that acts to disrupt tubulin. Such toxins may comprise, without limitation, rhizoxin/maytansine, paclitaxel, vincristine and vinblastine, colchicine, auristatin, dolastatin 10, peloruside A, alkylating agents, antimitotic agents, topoisomerase I inhibitors, and camptothecin derivatives.

In other non-limiting embodiments, the toxin portion of the immunoconjugate may be an alkylating agent including, without limitation, busulfan, carboxyphthalatoplatinum, chlorambucil, chlorozotocin, cisplatinum, clomesone, cyanomorpholinodoxorubicin, cyclodisone, dianhydrogalactitol, fluorodopan, hepsulfam, hycanthone, melphalan, mitomycin C, mitozolamide, nitrogen mustard, piperazine, piperazinedione, pipobroman, porfiromycin, spirohydantoin mustard, teroxirone, tetraplatin, triethylenemelamine, and the like.

In other non-limiting embodiments, the toxin portion of the immunoconjugate of the invention may be an antimitotic agent including, without limitation, allocolchicine, halichondrin B, colchicine, colchicine derivative, maytansine, rhizoxin, taxol, taxol derivative, thiocolchicine, trityl cysteine, vinblastine sulfate, and vincristine sulfate.

In other non-limiting embodiments, the toxin portion of an immunoconjugate of the invention may comprise a topoisomerase II inhibitor including, without limitation, doxorubicin, amonafide, anthrapyrazole derivative, pyrazoloacridine, bisantrene HCl, daunorubicin, deoxydoxorubicin, mitoxantrone, menogaril, N,N-dibenzyl daunomycin, oxanthrazole, and rubidazone.

In other non-limiting embodiments, the toxin portion of the immunoconjugate may be an RNA or DNA antimetabolite including, without limitation 5-azacytidine, 5-fluorouracil, acivicin, aminopterin, aminopterin derivative, 5,6-dihydro-5-azacytidine, methotrexate, methotrexate derivative, N-(phosphonoacetyl)-L-aspartate, pyrazofurin, trimetrexate, 2'-deoxy-5-fluorouridine, aphidicolin glycinate, 5-aza-2'-deoxycytidine, cyclocytidine, guanazole, hydroxyurea, inosine glycodialdehyde, macbecin II, pyrazoloimidazole, thioguanine, and thiopurine.

In some embodiments, the immunoconjugate is a humanized antibody fragment that binds to the extracellular domain of human EpCAM linked to *Pseudomonas* exotoxin A. In particular, the immunoconjugate may be a recombinant stabilized and humanized Fab fragment of EpCAM antibody that has been fused to a truncated form of *Pseudomonas* exotoxin A (ETA 252-608 amino acids), as shown in SEQ ID NO: 3. This immunoconjugate may bind to EpCAM expressed on cancer cells. Once bound, the immunoconjugate is internalized and the *Pseudomonas* exotoxin A kills cells or blocks the protein synthesis, thereby leading to cell death. Importantly, since most normal mucosal cells and fibroblasts do not widely express EpCAM, and therefore cannot internalize the immunoconjugate, they are protected from the potential side-effects of the exotoxin.

In some embodiments, the immunoconjugate may be a Fab attached to *Pseudomonas* exotoxin A. In some embodiments, the Fab may have a heavy chain with an amino acid sequence of SEQ ID NO: 1 and a light chain with an amino acid sequence of SEQ ID NO: 2, and the *Pseudomonas* exotoxin A (ETA 252-608 amino acids) is fused to the C-terminus of SEQ ID NO: 1. In some embodiments, the Fab may have a heavy chain with an amino acid sequence of SEQ ID NO: 1 and a light chain with an amino acid sequence of SEQ ID NO: 2, and the *Pseudomonas* exotoxin A (ETA 252-608 amino acids) is fused to the C-terminus of SEQ ID NO: 2. In some embodiments, the Fab may have a heavy chain with an amino acid sequence of SEQ ID NO: 11 and a light chain with an amino acid sequence of SEQ ID NO: 12, and the *Pseudomonas* exotoxin A (ETA 252-608 amino acids) is fused to the C-terminus of SEQ ID NO: 11. In some embodiments, the Fab may have a heavy chain with an amino acid sequence of SEQ ID NO: 11 and a light chain with an amino acid sequence of SEQ ID NO: 12, and the *Pseudomonas* exotoxin A (ETA 252-608 amino acids) is fused to the C-terminus of SEQ ID NO: 12.

In some embodiments, the immunoconjugate may be a humanized EpCAM antibody fragment attached to modified bouganin protein, wherein the modified bouganin has a reduced propensity to elicit an immune response. In a preferred embodiment, the modified bouganin has a reduced propensity to activate T-cells and the modified bouganin is modified at one or more amino acid residues in a T-cell epitope. In some embodiments, the modified bouganin protein (deBouganin) has amino acids as shown in SEQ ID NO: 4. In some embodiments, the modified bouganin protein may have amino acids as shown in SEQ ID NO: 9. In some embodiments, the modified bouganin protein may have amino acids as shown in SEQ ID NO: 33. In some embodiments, the modified bouganin protein may have amino acids as shown in SEQ ID NO: 42. In some embodiments, the modified bouganin protein may have amino acids as shown in SEQ ID NO: 43.

In some embodiments, the immunoconjugate may be a Fab attached to modified bouganin protein. In some embodiments, the Fab may have a heavy chain with an amino acid sequence of SEQ ID NO: 1 and a light chain with an amino acid sequence of SEQ ID NO: 2, and the modified bouganin protein is fused to the C-terminus of SEQ ID NO: 1. In some embodiments, the Fab may have a heavy chain with an amino acid sequence of SEQ ID NO: 1 and a light chain with an amino acid sequence of SEQ ID NO: 2, and the modified bouganin protein is fused to the C-terminus of SEQ ID NO: 2. In some embodiments, the Fab may have a heavy chain with an amino acid sequence of SEQ ID NO: 11 and a light chain with an amino acid sequence of SEQ ID NO: 12, and the modified bouganin protein is fused to the C-terminus of SEQ ID NO: 11. In some embodiments, the Fab may have a heavy chain with an amino acid sequence of SEQ ID NO: 11 and a light chain with an amino acid sequence of SEQ ID NO: 12, and the modified bouganin protein is fused to the C-terminus of SEQ ID NO: 12. In some embodiments, the Fab may have a heavy chain with an amino acid sequence of SEQ ID NO: 31 and a light chain with an amino acid sequence of SEQ ID NO: 12, and the modified bouganin protein is fused to the C-terminus of SEQ ID NO: 31. In some embodiments, the Fab may have a heavy chain with an amino acid sequence of SEQ ID NO: 31 and a light chain with an amino acid sequence of SEQ ID NO: 12, and the modified bouganin protein is fused to the C-terminus of SEQ ID NO: 12. In some embodiments, the Fab may have a heavy chain with an amino acid sequence of SEQ ID NO: 32 and a light chain with an amino acid sequence of SEQ ID NO: 12, and the modified bouganin protein is fused to the C-terminus of SEQ ID NO: 32. In some embodiments, the Fab may have a heavy chain with an amino acid sequence of SEQ ID NO: 32 and a light chain with an amino acid sequence of SEQ ID NO: 12, and the modified bouganin protein is fused to the C-terminus of SEQ ID NO: 12.

In some embodiments, the immunoconjugate may be VB6-845 Fab having a first polypeptide as shown in SEQ ID NO: 13 and a second polypeptide as shown in SEQ ID NO: 2. The first and the second polypeptide may be joined by one or more di-sulfide linkages. In some embodiments, the immunoconjugate may be VB6-845 Fab having a first polypeptide selected from SEQ ID NOS: 1, 11, 31, or 32, and a second polypeptide as shown in SEQ ID NO: 16. In some embodiments, the immunoconjugate may be VB6-845 Fab having a first polypeptide as shown in SEQ ID NO: 14 and a second polypeptide as shown in SEQ ID NO: 12. In some embodiments, the immunoconjugate may be VB6-845 Fab having a first polypeptide selected from SEQ ID NOS: 1, 11, 31, or 32, and a second polypeptide as shown in SEQ ID NO: 17. In some embodiments, the immunoconjugate may be VB6-845 Fab having a first polypeptide as shown in SEQ ID NO: 34 and a second polypeptide as shown in SEQ ID NO: 2. In some embodiments, the immunoconjugate may be VB6-845 Fab having a first polypeptide selected from SEQ ID NOS: 1, 11, 31, or 32, and a second polypeptide as shown in SEQ ID NO: 35. In some embodiments, the immunoconjugate may be VB6-845 Fab having a first polypeptide as shown in SEQ ID NO: 36 and a second polypeptide as shown in SEQ ID NO: 12. In some embodiments, the immunoconjugate may be VB6-845 Fab having a first polypeptide selected from SEQ ID NOS: 1, 11, 31, or 32, and a second polypeptide as shown in SEQ ID NO: 37. In some embodiments, the immunoconjugate may be VB6-845 Fab having a first polypeptide as shown in SEQ ID NO: 38 and a second polypeptide as shown in SEQ ID NO: 12. In some embodiments, the immunoconjugate may be VB6-845 Fab having a first polypeptide as shown in SEQ ID NO: 40 and a second polypeptide as shown in SEQ ID NO: 12. In some embodiments, the immunoconjugate may be VB6-845 Fab having a first polypeptide as shown in SEQ ID NO: 39 and a second polypeptide as shown in SEQ ID NO: 12. In some embodiments, the immunoconjugate may be VB6-845 Fab having a first polypeptide as shown in SEQ ID NO: 41 and a second polypeptide as shown in SEQ ID NO: 12. In some embodiments, the immunoconjugate may be VB6-845 Fab having a first polypeptide as shown in SEQ ID NO: 44 and a second polypeptide as shown in SEQ ID NO: 2. In some embodiments, the immunoconjugate may be VB6-845 Fab having a first polypeptide as shown in SEQ ID NO: 44 and a second polypeptide as shown in SEQ ID NO: 12. In some embodiments, the immunoconjugate may be VB6-845 Fab having a first polypeptide selected from SEQ ID NOS: 1, 11, 31, or 32, and a second polypeptide as shown in SEQ ID NO: 45. In some embodiments, the immunoconjugate may be VB6-845 Fab having a first polypeptide as shown in SEQ ID NO: 46 and a second polypeptide as shown in SEQ ID NO: 2. In some embodiments, the immunoconjugate may be VB6-845 Fab having a first polypeptide as shown in SEQ ID NO: 46 and a second polypeptide as shown in SEQ ID NO: 12. In some embodiments, the immunoconjugate may be VB6-845 Fab having a first polypeptide selected from SEQ ID NOS: 1, 11, 31, or 32, and a second polypeptide as shown in SEQ ID NO: 47. In some embodiments, the immunoconjugate may be VB6-845 Fab having a first polypeptide as shown in SEQ ID NO: 48 and a second polypeptide as shown in SEQ ID NO: 2. In some embodiments, the immunoconjugate may be VB6-845 Fab having a first polypeptide as shown in SEQ ID NO: 48 and a second polypeptide as shown in SEQ ID NO: 12. In some embodiments, the immunoconjugate may be VB6-845 Fab having a first polypeptide as shown in SEQ ID NO: 49 and a second polypeptide as shown in SEQ ID NO: 2. In some embodiments, the immunoconjugate may be VB6-845 Fab having a first polypeptide as shown in SEQ ID NO: 49 and a second polypeptide as shown in SEQ ID NO: 12.

The first and the second polypeptide disclosed herein in the above immunoconjugates may be joined by one or more di-sulfide linkages.

The antibodies or the antibody fragments described herein may be conjugated to the effector molecule by any means. For example, the antibody or the antibody fragment may be attached to the toxin by chemical or recombinant means. Chemical means for preparing fusions or conjugates are known in the art and can be used to prepare the immunoconjugate. The method used to conjugate the antibody or the antibody fragment and toxin must be capable of joining the antibody with the toxin without interfering with the ability of the antibody or the antibody fragment to bind to the target molecule.

In one embodiment, the antibody and toxin are both proteins and can be conjugated using techniques well known in the art. There are several hundred crosslinkers disclosed in the art that can conjugate two proteins. The crosslinker is generally chosen based on the reactive functional groups available or inserted on the antibody or toxin. In addition, if there are no reactive groups, a photoactivatible crosslinker can be used. In certain instances, it may be desirable to include a spacer between the antibody and the toxin. Crosslinking agents known to the art include the homobifunctional agents: glutaraldehyde, dimethyladipimidate and bis (diazobenzidine) and the heterobifunctional agents: m-maleimidobenzoyl-N-hydroxysuccinimide and sulfo-m maleimidobenzoyl-N-hydroxysuccinimide.

Other crosslinkers that may be used to couple an effector molecule to the antibody fragment include TPCH(S-(2-thiopyridyl)-L-cysteine hydrazide and TPMPH ((S-(2-thiopyridyl) mercapto-propionohydrazide). TPCH and TPMPH react at the carbohydrate moieties of glycoproteins that have been previously oxidized by mild periodate treatment, thus forming a hydrazone bond between the hydrazide portion of the crosslinker and the periodate generated aldehydes. The hetero-bifunctional crosslinkers GMBS (N-gama-malimidobutyryloxy)-succinimide) and SMCC (succinimidyl 4-(N-maleimido-methyl)cyclohexane) react with primary amines, thus introducing a maleimide group onto the component. This maleimide group can subsequently react with sulfhydryls on the other component, which can be introduced by previously mentioned crosslinkers, thus forming a stable thioether bond between the components. If steric hindrance between components interferes with either component's activity, crosslinkers can be used which introduce long spacer arms between components and include derivatives, such as n-succinimidyl-3-(2-pyridyldithio)propionate (SPDP). Thus, there is an abundance of suitable crosslinkers that can be used and each of which is selected depending on the effects it has on optimal immunoconjugate production.

An antibody-effector molecule fusion protein may also be prepared using recombinant DNA techniques. In such a case a DNA sequence encoding the antibody is fused to a DNA sequence encoding an effector molecule, such as a toxin, resulting in a chimeric DNA molecule. The chimeric DNA sequence is transfected into a host cell that expresses the antibody-effector molecule fusion protein. The fusion protein can be recovered from the cell culture and purified using techniques known in the art.

The antibody portion of an immunoconjugate may be immunoglobulin derived, i.e., can be traced to a starting molecule that is an immunoglobulin (or antibody). For example, the antibody may be produced by modification of an immunoglobulin scaffold using standard techniques known in the art. In another, non-limiting example, immunoglobulin domains (e.g., variable heavy and/or light chains) may be linked to a non-immunoglobulin scaffold. Further, the antibody may be developed by, without limitation, chemical reaction or genetic design. Accordingly, in a non-limiting example, an immunoconjugate may comprise an immunoglobulin-derived polypeptide (e.g., an antibody selected from an antibody library), or variant thereof, that specifically binds to liver cancer cells; and a toxin or variant thereof. Such immunoglobulin polypeptides can be re-designed to affect their binding characteristics to a target a tumor associated molecule, or to improve their physical characteristics, for example.

The antibody portion of the immunoconjugate need not be immunoglobulin based. Accordingly, an immunoconjugate may comprise a non-immunoglobulin polypeptide (e.g., Affibody®), or variant thereof, that specifically binds to liver cancer cells; and a toxin or variant thereof. Such non-immunoglobulin polypeptide can be designed to bind to a target tumor associated molecule. Moreover, non-immunoglobulin polypeptide can be engineered to a desired affinity or avidity and can be designed to tolerate a variety of physical conditions, including extreme pH ranges and relatively high temperature.

Indeed, for use in a pharmaceutical composition, the design of a non-immunoglobulin polypeptide with a relatively long half-life at physiological conditions (e.g., 37° C. in the presence of peptidases) can be advantageous. Furthermore, such molecules, or variants thereof, may demonstrate good solubility, small size, proper folding and can be expressed in readily available, low-cost bacterial systems, and thus manufactured in commercially reasonable quantities. The ability to design a non-immunoglobulin polypeptide is within the skill of the ordinary artisan.

Examples of epitope-binding polypeptides include, without limitation, ligands comprising a fibronectin type III domain, binding molecules based on assembly of repeat protein domains comprising Pleckstrin-Homology (PH) domains, ankyrin repeats, and the like.

In other non-limiting embodiments, the immunoconjugate comprises a variant that has amino acid sequences, by at least 10%, 15%, 20%, 25%, 30%, 35%, 40%, 45%, 50%, 55%, 60%, 65%, 70%, 75%, 80%, 85%, 90%, or 95% identical to *Pseudomonas* exotoxin A as shown in SEQ ID NO: 3.

In other embodiments, the immunoconjugate comprises a variant that has amino acid sequences, by at least 10%, 15%, 20%, 25%, 30%, 35%, 40%, 45%, 50%, 55%, 60%, 65%, 70%, 75%, 80%, 85%, 90%, or 95% identical to bouganin protein as shown in SEQ ID NO: 4.

Methods of Use

Disclosed herein are methods of using antibodies, antibody fragments and immunoconjugates described herein. In each of the foregoing embodiments, the antibodies, the antibody fragments, and/or the immunoconjugates used may include any of the de-immunized antibodies/antibody fragments disclosed herein, wherein the antibody/antibody fragment comprises a heavy chain having an amino acid sequence of SEQ ID NO: 1, SEQ ID NO: 11, SEQ ID NO: 31, or SEQ ID NO: 32; and a light chain having an amino acid sequence of SEQ ID NO: 2 or SEQ ID NO: 12.

In some embodiments, a method of treating a subject with cancer may involve administering a therapeutically effective amount of an antibody, wherein the antibody comprises a heavy chain having an amino acid sequence of SEQ ID NO: 1, SEQ ID NO: 11, SEQ ID NO: 31, or SEQ ID NO: 32; and a light chain having an amino acid sequence of SEQ ID NO: 2 or SEQ ID NO: 12. The antibody may be an antibody fragment, such as Fab, Fab', $F(ab')_2$, scFv, dsFv, ds-scFv, dimers, minibodies, diabodies, bispecific antibody fragments, multimers, and any combination thereof. The antibody or the antibody fragment may be any of the de-immunized antibodies or de-immunized antibody fragments disclosed herein. In some embodiments, the antibody further comprises an effector molecule attached to the antibody (collectively, an immunoconjugate). In some embodiments described herein, the effector molecule may be a radioisotope, an antineoplastic agent, an immunomodulator, a biological response modifier, lectin, a toxin, a chromophore, a fluorophore, a chemiluminescent compound, an enzyme, a metal ion, and any combination thereof.

In some embodiments, the antibodies and immunoconjugates may be used to treat cancer, such as lung cancer, gastric cancer, renal cancer, thyroid cancer, breast cancer, bladder cancer, ovarian cancer, colorectal cancer, head and neck cancer, hepatocellular carcinoma, esophageal, pancreas, and prostate cancer. Cancers originating from any epithelial cell may also be targeted by these immunoconjugates and antibodies.

In preferred non-limiting embodiments, the cancer is amenable to treatment by direct administration of the antibody or immunoconjugate to the cancer site. For example, a target tumor mass may be close to the surface of the skin. In another example, a diseased tissue may be encapsulated by a cyst, or is found in a substantially enclosed cavity including, without limitation, a lumen. In other embodiments, the cancer is amenable to treatment by intravenous administration of the antibody or immunoconjugate.

In some embodiments, a kit for diagnosing cancer may include an antibody or fragment thereof having a heavy chain amino acid sequence of SEQ ID NO: 1, SEQ ID NO: 11, SEQ ID NO: 31, or SEQ ID NO: 32; and a light chain having amino acid sequence of SEQ ID NO: 2 or SEQ ID NO: 12, and instructions for the use thereof. In some embodiments, a kit for diagnosing cancer may include an immunoconjugate, wherein said immunoconjugate comprises an antibody or fragment thereof having a heavy chain amino acid sequence of SEQ ID NO: 1, SEQ ID NO: 11, SEQ ID NO: 31, or SEQ ID NO: 32; and a light chain having amino acid sequence of SEQ ID NO: 2 or SEQ ID NO: 12, attached to an effector molecule and instructions for the use thereof. The antibody or the antibody fragment may be any of the de-immunized antibodies or de-immunized antibody fragments disclosed herein.

In some embodiments, the kit for detecting cancer may include anti-EpCAM antibody fragment, and preferably further include a reagent containing a labeled anti-Ig antibody, for example, an anti-Ig antibody linked with an enzyme such as alkaline phosphatase or a radiolabeled anti-Ig antibody. In some embodiments, the anti-EpCAM antibody fragment may be attached to a chromophore, a fluorophore or a radiolabelled ligand.

The immunoconjugates and the antibodies disclosed herein may also be used to detect or monitor in a subject. In some embodiments, a method of detecting or monitoring cancer in a subject may involve contacting a test sample taken from the subject with an antibody to form an antibody-antigen complex, wherein the antibody comprises a heavy chain amino acid sequence of SEQ ID NO: 1 SEQ ID NO: 11, SEQ ID NO: 31, or SEQ ID NO: 32; and a light chain having an amino acid sequence of SEQ ID NO: 2 or SEQ ID NO: 12; measuring the amount of the antibody-antigen complex in the test sample; and normalizing the results against a control. The test sample may be serum, lymph, ascitic exudate, intercellular fluid, tissue lysate, saliva, tissue sections, cells, biopsy samples, and the like. The antibody-antigen complex may be detected by any means, such as for example, dot-blot method, Western blot method, ELISA method, or sandwich ELISA method. Also, the antibody-antigen complex can be detected by use according to multistage reactions, such as reaction with a biotin-bound anti-Ig antibody and then with an avidin-bound material. In other embodiments, a method of detecting or monitoring cancer in a subject may involve contacting a test sample taken from the subject with an immunoconjugate to form a complex, wherein the immunoconjugate comprises an antibody having a heavy chain amino acid sequence of SEQ ID NO: 1, SEQ ID NO: 11, SEQ ID NO: 31, or SEQ ID NO: 32; and a light chain having an amino acid sequence of SEQ ID NO: 2 or SEQ ID NO: 12; measuring the amount of the complex in the test sample; and normalizing the results against a control.

In another embodiment, a method of detecting or monitoring cancer in a subject may involve administering to the subject an antibody comprising a heavy chain having an amino acid sequence selected from SEQ ID NO: 1, SEQ ID NO: 11, SEQ ID NO: 31, or SEQ ID NO: 32; and a light chain having an amino acid sequence selected from SEQ ID NO: 2 and SEQ ID NO: 12; and detecting the antibody. In a further embodiment, a method of detecting or monitoring cancer in a subject may involve administering to the subject an immunoconjugate comprising an antibody having a heavy chain having an amino acid sequence selected from SEQ ID NO: 1, SEQ ID NO: 11, SEQ ID NO: 31, or SEQ ID NO: 32; and a light chain having an amino acid sequence selected from SEQ ID NO: 2 and SEQ ID NO: 12; and detecting the immunoconjugate.

In some embodiments, the antibodies and the immunoconjugates disclosed herein may be used for imaging a tumor in a subject. In some embodiments, a method of imaging a tumor in a subject may involve administering to the subject an antibody or an antibody fragment comprising a heavy chain having an amino acid sequence of SEQ ID NO: 1, SEQ ID NO: 11, SEQ ID NO: 31, or SEQ ID NO: 32; and a light chain having an amino acid sequence of SEQ ID NO: 2 or SEQ ID NO: 12; and detecting the antibody or the antibody fragment by in vivo imaging. The antibody or the antibody fragment may be any of the de-immunized antibodies or de-immunized antibody fragments disclosed herein and may be attached to an effector molecule. In some embodiments, a method of imaging a tumor in a subject may involve administering to the subject an immunoconjuate comprising an antibody having a heavy chain having an amino acid sequence of SEQ ID NO: 1, SEQ ID NO: 11, SEQ ID NO: 31, or SEQ ID NO: 32; and a light chain having an amino acid sequence of SEQ ID NO: 2 or SEQ ID NO: 12; and detecting the immunoconjugate by in vivo imaging. The immunoconjugate may further include an effector molecule.

In some embodiments, the effector molecule utilized for detecting cancer or imaging a tumor may be a radioisotope, a chromophore, a fluorophore, a chemiluminescent compound, an enzyme, a metal ion, and any combination thereof. The in vivo imaging may be performed by any known technique in the art, such as near-infrared fluorescence imaging (NIRF), fluorescence reflectance imaging (FRI), fluorescence-mediated tomography (FMT), positron emission tomography (PET), single photon emission tomography (SPECT), magnetic resonance imaging (MRI), PET with concurrent computed tomography imaging (PET/CT), PET with concurrent magnetic resonance imaging (PET/MRI), and any combination thereof.

In some embodiments, the method may further include resecting cancerous tissue, such as a tumor or a part of an organ, after in vivo imaging of the subject. Surgical resection can be performed by any technique known in the art. In some embodiments, the method may further include administering the antibody or immunoconjugate after resection to measure the completeness of tumor resection.

In certain embodiments, the antibodies as described herein are labeled with a radiotracer. A radiotracer is typically a substance containing a radioisotope that allows for easy detection and measurement. A number of different forms of hydrogen, carbon, phosphorous, sulfur and iodine are commonly used in medical diagnostics. The antibodies of the present invention may be labeled with any suitable radiotracer. Preferred radiotracers include radiotracers for medical imaging. Common radiotracers used include $^{18}F$, $^{67}Ga$, $^{81m}Kr$, $^{82}Rb$, $^{99m}Tc$, $^{m}In$, $^{123}I$, $^{131}I$, $^{133}Xe$, $^{201}Tl$ and $^{90}Y$. Preferably, the antibodies as described herein are labeled with $^{18}F$, $^{123/131}I$, $^{m}In$, $^{90}Y$ or $^{99m}Tc$.

The antibodies of the present invention may also be labeled with any fluorescent probes known in the art. Non-limiting examples include fluorescein, amino coumarin acetic acid, tetramethylchodomine isocyanate, Texas Red, Cy 3.0, Cy 5.0, green fluorescent protein, and the like.

In another preferred embodiment, the antibodies as described herein are labeled with a contrast agent. A contrast agent is a substance used to increase or modify the contrast of organs, fluids or anatomical structures in the human or animal body. The antibodies of the present invention may be labeled with any suitable contrast agent. Preferred contrast agents include contrast agents for medical imaging. Preferably, the antibodies of the present invention are labeled with an MRI (magnetic resonance imaging) contrast agent such as a superparamagnetic contrast agent or a paramagnetic contrast agent. MRI contrast agents are typically chelated metals or colloids. The most commonly used contrast agents include gadolinium (Gd) based contrast agents such as gadolinium-DTPA, iron oxide based contrast agents such as superparamagnetic Small Particles of Iron Oxide (SPIO) and superparamagnetic Ultrasmall Small Particles of Iron Oxide (USPIO) and paramagnetic contrast agents based on manganese chelates such as Mn-DPDP.

The invention also provides methods for reducing the risk of post-surgical complications comprising administering an effective amount of an immunoconjugate before, during, or after surgery, and in specific non-limiting embodiments, surgery to treat cancer.

The invention also provides methods for preventing occurrence, preventing or delaying recurrence, or reducing the rate of recurrence of cancer comprising directly administering to a patient in need thereof an effective amount of an immunoconjugate.

The invention also provides methods for sensitizing a tumor or cancer to one or more other anticancer agents comprising administering an immunoconjugate of the invention. In a non-limiting embodiment, the other anticancer agent comprises another EpCAM-targeted immunoconjugate. In another non-limiting embodiment, the other anticancer agent comprises radiation. The other anticancer agents may be administered prior to, overlapping with, concurrently, and/or after administration of the immunoconjugate. When administered concurrently, the immunoconjugate and other anticancer agent may be administered in a single formulation or in separate formulations, and if separately, then optionally, by different modes of administration. Accordingly, the combination of one or more immunoconjugates and one or more other anticancer agents may synergistically act to combat the tumor or cancer. In some embodiments, the immunoconjugate may be co-administered, concurrently administered, or sequentially administered with one or more anticancer agents.

In some embodiments, the anticancer agents may be tamoxifen, toremifen, raloxifene, droloxifene, iodoxyfene, megestrol acetate, anasfrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, Irinotecan, topotecan, an epothilone, Iressa, Tarceva, Sorafenib, angiogenesis inhibitors, EGF inhibitors, VEGF inhibitors, CDK inhibitors, cytokines, Her1 and Her2 inhibitors, and monoclonal antibodies.

In another embodiment, methods of treating cancer comprising administering an immunoconjugate in combination with a regimen of radiation therapy is provided. The therapy may also comprise surgery and/or chemotherapy. For example, the immunoconjugate may be administered in combination with radiation therapy and cisplatin (Platinol), fluo-rouracil (5-FU, Adrucil), carboplatin (Paraplatin), and/or paclitaxel (Taxol). Treatment with the immunoconjugate may allow use according to lower doses of radiation and/or less frequent radiation treatments, which may for example, reduce the incidence of severe sore throat that impedes swallowing function potentially resulting in undesired weight loss or dehydration.

Pharmaceutical compositions for combination therapy may also include, without limitation, antibiotics (e.g., dactinomycin, bleomycin, mithramycin, anthramycin), asparaginase, BCG protein, diphtheria toxin, procaine, tetracaine, lidocaine, propranolol, antimitotic agents, abrin, ricin A, *Pseudomonas* exotoxin, nerve growth factor, platelet derived growth factor, tissue plasminogen activator, antihistaminic agents, anti-nausea agents, etc.

Indeed, direct administration of an effective amount of an immunoconjugate to a patient in need of such treatment may result in reduced doses of another anticancer agent having clinically significant efficacy. Such efficacy of the reduced dose of the other anticancer agent may not be observed absent administration with an immunoconjugate. Accordingly, the present invention provides methods for treating a tumor or cancer comprising administering a reduced dose of one or more other anticancer agents.

Moreover, combination therapy comprising an immunoconjugate to a patient in need of such treatment may permit relatively short treatment times when compared to the duration or number of cycles of standard treatment regimens. Accordingly, the present invention provides methods for treating a tumor or cancer comprising administering one or more other anticancer agents for relatively short duration and/or in fewer treatment cycles.

Thus, in accordance with the present invention, combination therapies comprising an immunoconjugate and another anticancer agent may reduce toxicity (i.e., side effects) of the overall cancer treatment. For example, reduced toxicity, when compared to a monotherapy or another combination therapy, may be observed when delivering a reduced dose of immunoconjugate and/or other anticancer agent, and/or when reducing the duration of a cycle (i.e., the period of a single administration or the period of a series of such administrations), and/or when reducing the number of cycles.

Clinical outcomes of cancer treatments using an antibody or immunoconjugate of the invention are readily discernible by one of skill in the relevant art, such as a physician. For example, standard medical tests to measure clinical markers of cancer may be strong indicators of the treatment's efficacy. Such tests may include, without limitation, physical examination, performance scales, disease markers, 12-lead ECG, tumor measurements, tissue biopsy, cytoscopy, cytology, longest diameter of tumor calculations, radiography, digital imaging of the tumor, vital signs, weight, recordation of adverse events, assessment of infectious episodes, assessment of concomitant medications, pain assessment, blood or serum chemistry, detecting serum markers, urinalysis, CT scan, and pharmacokinetic analysis. Furthermore, synergistic effects of a combination therapy comprising the immunoconjugate and another anticancer agent may be determined by comparative studies with patients undergoing monotherapy.

The effective dose of the antibody or immunoconjugate to be administered during a cycle varies according to the mode of administration. Direct administration (e.g., intratumoral injection) requires much smaller total body doses of immunoconjugate as compared to systemic, intravenous administration of the immunoconjugate. It will be evident to the skilled artisan that local administration can result in lower body doses, and in those circumstances, and resulting low circulating plasma level of immunoconjugate would be expected and desired.

In one embodiment, the effective dose by direct administration of antibody or immunoconjugate may range from about 10 to 3000, 20 to 900, 30 to 800, 40 to 700, 50 to 600, 60 to 500, 70 to 400, 80 to 300, 90 to 200, or 100 to 150 micrograms/tumor/day. In other embodiments, the dose may range from approximately 10 to 20, 21 to 40, 41 to 80, 81 to 100, 101 to 130, 131 to 150, 151 to 200, 201 to 280, 281 to 350, 351 to 500, 501 to 1000, 1001 to 2000, or 2001 to 3000 micrograms/tumor/day. In specific embodiments, the dose may be at least approximately 20, 40, 80, 130, 200, 280, 400, 500, 750, 1000, 2000, or 3000 micrograms/tumor/day.

In other embodiments, the antibody or immunoconjugate administration is at a dosage of about 0.01 mg/kg/dose to about 2000 mg/kg/dose.

In another embodiment, the effective dose of antibody or immunoconjugate may range from about 100 to 5000, 200 to 4000, 300 to 3000, 400 to 2000, 500 to 1000, 600 to 900, or 700 to 1500 micrograms/tumor/month. In other embodiments, the dose may range from approximately 100 to 199, 200 to 399, 400 to 649, 650 to 999, 1000 to 1799, 1800 to 2499, 2500 to 3499, 3500 to 4999, 5000 to 7499, 7500 to 10000, or 10001 to 20000 micrograms/tumor/month. In specific embodiments, the dose may be at least approximately 100, 200, 400, 650, 1000, 1400, 2000, 2500, 3000, 3500, 4000, 4500, 5000, 7500, 10000, or 20000 micrograms/tumor/month.

In another embodiment, the antibody or immunoconjugate is administered intratumourally at a total dose per cycle equivalent to, or below the maximum tolerated dose established in a safety trial but the dosage is standardized in relation to the tumor volume. For example, subjects will receive between 1 microgram per $cm^3$ and 500 microgram per $cm^3$ tumor or a dose sufficient to reach about between 14 picomole and 7 nanomole per $cm^3$ tumor tissue. The dose will be administered in a volume not exceeding about 20-50% of the tumor volume. The immunoconjugate will be diluted in a suitable salt solution. For example, for a tumor of estimated volume of 3 $cm^3$, a target dose of 14 picomoles (1 microgram per $cm^3$), and a maximum injection relative volume of about ⅓ of the tumor, 3 microgram of immunoconjugate will be diluted into about 1 ml of diluent.

The effective dose of another anticancer agent to be administered together with an antibody or immunoconjugate during a cycle also varies according to the mode of administration. The one or more anticancer agent may be delivered intratumorally, or by other modes of administration. Typically, chemotherapeutic agents are administered systemically. Standard dosage and treatment regimens are known in the art (see, e.g., the latest editions of the Merck Index and the Physician's Desk Reference).

For example, in one embodiment, the additional anticancer agent comprises dacarbazine at a dose ranging from approximately 200 to 4000 $mg/m^2$/cycle. In a preferred embodiment, the dose ranges from 700 to 1000 $mg/m^2$/cycle.

In another embodiment, the additional anticancer agent comprises fludarabine at a dose ranging from approximately 25 to 50 $mg/m^2$/cycle.

In another embodiment, the additional anticancer agent comprises cytosine arabinoside (Ara-C) at a dose ranging from approximately 200 to 2000 $mg/m^2$/cycle.

In another embodiment, the additional anticancer agent comprises docetaxel at a dose ranging from approximately 1.5 to 7.5 mg/kg/cycle.

In another embodiment, the additional anticancer agent comprises paclitaxel at a dose ranging from approximately 5 to 15 mg/kg/cycle.

In yet another embodiment, the additional anticancer agent comprises cisplatin at a dose ranging from approximately 5 to 20 mg/kg/cycle.

In yet another embodiment, the additional anticancer agent comprises 5-fluorouracil at a dose ranging from approximately 5 to 20 mg/kg/cycle.

In yet another embodiment, the additional anticancer agent comprises doxorubicin at a dose ranging from approximately 2 to 8 mg/kg/cycle.

In yet another embodiment, the additional anticancer agent comprises epipodophyllotoxin at a dose ranging from approximately 40 to 160 mg/kg/cycle.

In yet another embodiment, the additional anticancer agent comprises cyclophosphamide at a dose ranging from approximately 50 to 200 mg/kg/cycle.

In yet another embodiment, the additional anticancer agent comprises irinotecan at a dose ranging from approximately 50 to 75, 75 to 100, 100 to 125, or 125 to 150 $mg/m^2$/cycle.

In yet another embodiment, the anticancer agent comprises vinblastine at a dose ranging from approximately 3.7 to 5.4, 5.5 to 7.4, 7.5 to 11, or 11 to 18.5 $mg/m^2$/cycle.

In yet another embodiment, the additional anticancer agent comprises vincristine at a dose ranging from approximately 0.7 to 1.4, or 1.5 to 2 $mg/m^2$/cycle.

In yet another embodiment, the additional anticancer agent comprises methotrexate at a dose ranging from approximately 3.3 to 5, 5 to 10, 10 to 100, or 100 to 1000 $mg/m^2$/cycle.

Combination therapy with an antibody or immunoconjugate may sensitize the cancer or tumor to administration of an additional anticancer agent. Accordingly, the present invention contemplates combination therapies for preventing, treating, and/or preventing recurrence of cancer comprising administering an effective amount of an antibody or immunoconjugate prior to, subsequently, or concurrently with a reduced dose of an anticancer agent. For example, initial treatment with an immunoconjugate may increase the sensitivity of a cancer or tumor to subsequent challenge with a dose of anticancer agent. This dose is near, or below, the low range of standard dosages when the anticancer agent is administered alone, or in the absence of an antibody or immunoconjugate. When concurrently administered, the antibody or immunoconjugate may be administered separately from the anticancer agent, and optionally, via a different mode of administration.

Accordingly, in one embodiment, the additional anticancer agent comprises cisplatin, e.g., PLATINOL or PLATINOL-AQ (Bristol Myers), at a dose ranging from approximately 5 to 10, 11 to 20, 21 to 40, or 41 to 75 $mg/m^2$/cycle.

In another embodiment, the additional anticancer agent comprises carboplatin, e.g., PARAPLATIN (Bristol Myers), at a dose ranging from approximately 2 to 3, 4 to 8, 9 to 16, 17 to 35, or 36 to 75 mg/m$^2$/cycle.

In another embodiment, the additional anticancer agent comprises cyclophosphamide, e.g., CYTOXAN (Bristol Myers Squibb), at a dose ranging from approximately 0.25 to 0.5, 0.6 to 0.9, 1 to 2, 3 to 5, 6 to 10, 11 to 20, or 21 to 40 mg/kg/cycle.

In another embodiment, the additional anticancer agent comprises cytarabine, e.g., CYTOSAR-U (Pharmacia & Upjohn), at a dose ranging from approximately 0.5 to 1, 2 to 4, 5 to 10, 11 to 25, 26 to 50, or 51 to 100 mg/m$^2$/cycle. In another embodiment, the additional anticancer agent comprises cytarabine liposome, e.g., DEPOCYT (Chiron Corp.), at a dose ranging from approximately 5 to 50 mg/m$^2$/cycle.

In another embodiment, the additional anticancer agent comprises dacarbazine, e.g., DTIC or DTICDOME (Bayer Corp.), at a dose ranging from approximately 15 to 250 mg/m$^2$/cycle or ranging from approximately 0.2 to 2 mg/kg/cycle.

In another embodiment, the additional anticancer agent comprises topotecan, e.g., HYCAMTIN (SmithKline Beecham), at a dose ranging from approximately 0.1 to 0.2, 0.3 to 0.4, 0.5 to 0.8, or 0.9 to 1.5 mg/m$^2$/Cycle.

In another embodiment, the additional anticancer agent comprises irinotecan, e.g., CAMPTOSAR (Pharmacia & Upjohn), at a dose ranging from approximately 5 to 9, 10 to 25, or 26 to 50 mg/m$^2$/cycle.

In another embodiment, the additional anticancer agent comprises fludarabine, e.g., FLUDARA (Berlex Laboratories), at a dose ranging from approximately 2.5 to 5, 6 to 10, 11 to 15, or 16 to 25 mg/m$^2$/cycle.

In another embodiment, the additional anticancer agent comprises cytosine arabinoside (Ara-C) at a dose ranging from approximately 200 to 2000 mg/m$^2$/cycle, 300 to 1000 mg/m$^2$/cycle, 400 to 800 mg/m$^2$/cycle, or 500 to 700 mg/m$^2$/cycle.

In another embodiment, the additional anticancer agent comprises docetaxel, e.g., TAXOTERE (Rhone Poulenc Rorer) at a dose ranging from approximately 6 to 10, 11 to 30, or 31 to 60 mg/m$^2$/cycle.

In another embodiment, the additional anticancer agent comprises paclitaxel, e.g., TAXOL (Bristol Myers Squibb), at a dose ranging from approximately 10 to 20, 21 to 40, 41 to 70, or 71 to 135 mg/kg/cycle.

In another embodiment, the additional anticancer agent comprises 5-fluorouracil at a dose ranging from approximately 0.5 to 5 mg/kg/cycle, 1 to 4 mg/kg/cycle, or 2-3 mg/kg/cycle.

In another embodiment, the additional anticancer agent comprises doxorubicin, e.g., ADRIAMYCIN (Pharmacia & Upjohn), DOXIL (Alza), RUBEX (Bristol Myers Squibb), at a dose ranging from approximately 2 to 4, 5 to 8, 9 to 15, 16 to 30, or 31 to 60 mg/kg/cycle.

In another embodiment, the additional anticancer agent comprises etoposide, e.g., VEPESID (Pharmacia & Upjohn), at a dose ranging from approximately 3.5 to 7, 8 to 15, 16 to 25, or 26 to 50 mg/m$^2$/cycle.

In another embodiment, the additional anticancer agent comprises vinblastine, e.g., VELBAN (Eli Lilly), at a dose ranging from approximately 0.3 to 0.5, 0.6 to 0.9, 1 to 2, or 3 to 3.6 mg/m$^2$/cycle.

In another embodiment, the additional anticancer agent comprises vincristine, e.g., ONCOVIN (Eli Lilly), at a dose ranging from approximately 0.1, 0.2, 0.3, 0.4, 0.5, 0.6 or 0.7 mg/m$^2$/cycle.

In another embodiment, the additional anticancer agent comprises methotrexate at a dose ranging from approximately 0.2 to 0.9, 1 to 5, 6 to 10, or 11 to 20 mg/m$^2$/cycle.

In another embodiment, an immunoconjugate is administered in combination with at least one other immunotherapeutic which includes, without limitation, rituxan, rituximab, campath-1, gemtuzumab, and trastuzutmab.

In another embodiment, an immunoconjugate is administered in combination with one or more anti-angiogenic agents which include, without limitation, angiostatin, thalidomide, kringle 5, endostatin, Serpin (Serine Protease Inhibitor), anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13 amino acid peptide corresponding to a fragment of platelet factor-4, a 14-amino acid peptide corresponding to a fragment of collagen I, a 19 amino acid peptide corresponding to a fragment of thrombospondin I, a 20-amino acid peptide corresponding to a fragment of SPARC, and a variant thereof, including a pharmaceutically acceptable salt thereof.

In another embodiment, an antibody or immunoconjugate is administered in combination with one or more cytokines which include, without limitation, lymphokines, tumor necrosis factors, tumor necrosis factor-like cytokine, lymphotoxin, interferon, macrophage inflammatory protein, granulocyte monocyte colony stimulating factor, interleukin (including, without limitation, interleukin-1, interleukin-2, interleukin-6, interleukin-12, interleukin-15, interleukin-18), and a variant thereof, including a pharmaceutically acceptable salt thereof.

In yet another embodiment, an antibody or immunoconjugate is administered in combination with a cancer vaccine including, without limitation, autologous cells or tissues, non-autologous cells or tissues, carcinoembryonic antigen, alpha-feto-protein, human chorionic gonadotropin, BCG live vaccine, melanocyte lineage proteins, and mutated, tumor-specific antigens.

In yet another embodiment, an antibody or immunoconjugate is administered in association with hormonal therapy. Hormonal therapeutics include, without limitation, a hormonal agonist, hormonal antagonist (e.g., flutamide, tamoxifen, leuprolide acetate (LUPRON)), and steroid (e.g., dexamethasone, retinoid, betamethasone, cortisol, cortisone, prednisone, dehydrotestosterone, glucocorticoid, mineralocorticoid, estrogen, testosterone, progestin).

In yet another embodiment, an antibody or immunoconjugate is administered in association with a gene therapy program to treat or prevent cancer.

In yet another embodiment, an EpCAM-targeted antibody or immunoconjugate is administered in combination with one or more agents that increase expression of EpCAM in the tumor cells of interest. EpCAM expression preferably is increased so that a greater number of EpCAM molecules are expressed on the tumor cell surface. For example, the agent may inhibit the normal cycles of EpCAM antigen endocytosis. Such combination treatment may improve the clinical efficacy of the EpCAM-targeted immunoconjugate alone, or with other anticancer agents or radiation therapy. In specific, nonlimiting embodiments, the agent which increases EpCAM expression in the tumor cells is vinorelbine tartrate (Navelbine) and/or paclitaxel (Taxol).

Combination therapy may thus increase the sensitivity of the cancer or tumor to the administered immunoconjugate and/or additional anticancer agent. In this manner, shorter treatment cycles may be possible thereby reducing toxic events. Accordingly, the invention provides a method for treating or preventing cancer comprising administering to a patient in need thereof an effective amount of an immunoconjugate and at least one other anticancer agent for a short treatment cycle. The cycle duration may range from approximately 1 to 30, 2 to 27, 3 to 15, 4 to 12, 5 to 9, or 6-8 days. The cycle duration may vary according to the specific anticancer agent in use. The invention also contemplates continuous or discontinuous administration, or daily doses divided into several partial administrations. An appropriate cycle duration for a specific anticancer agent will be appreciated by the skilled artisan, and the invention contemplates the continued assessment of optimal treatment schedules for each anticancer agent. Specific guidelines for the skilled artisan are known in the art.

Alternatively, longer treatment cycles may be desired. Accordingly, the cycle duration may range from approximately 10 to 56, 12 to 48, 14 to 28, 16 to 24, or 18 to 20 days. The cycle duration may vary according to the specific anticancer agent in use.

Routes of Administration

The antibodies and/or immunoconjugates described herein may be administered to the patient via any suitable route. The antibodies and/or immunoconjugates may be administered by injection into the vascular system or by injection into an organ. Preferred administration routes include parenteral, intravascular and/or intravenous injection. Parenteral administration includes subcutaneous, intramuscular, intraperitoneal, intracavity, intrathecal, intratumoral, transdermal and intravenous injection. In a preferred embodiment, the antibodies and/or immunoconjugates are administered intravenously as a bolus or by continuous infusion over a period of time. In other embodiments, the antibodies and/or immunoconjugates may be administered directly to the cancer site.

The immunoconjugate and antibodies of the present invention can be administered in the conventional manner by any route where they are active. Administration can be systemic, parenteral, topical, or oral. For example, administration can be, but is not limited to, parenteral, oral, buccal, or ocular routes, or intravaginally, by inhalation, by depot injections, or by implants. Thus, modes of administration for the antibodies/immunoconjugates of the present invention (either alone or in combination with other pharmaceuticals) can be, but are not limited to, sublingual, injectable (including short-acting, depot, implant and pellet forms injected subcutaneously or intramuscularly), or by use according to vaginal creams, suppositories, pessaries, vaginal rings, rectal suppositories, intrauterine devices, and transdermal forms such as patches and creams.

In accordance with one aspect of the present invention, the antibody or immunoconjugate and/or other anticancer agent is delivered to the patient by direct administration. Accordingly, the immunoconjugate and/or other anticancer agent may be administered, without limitation, by one or more direct injections into the tumor, by continuous or discontinuous perfusion into the tumor, by introduction of a reservoir of the immunoconjugate, by introduction of a slow-release apparatus into the tumor, by introduction of a slow-release formulation into the tumor, and/or by direct application onto the tumor. By the mode of administration into the tumor, introduction of the immunoconjugate and/or other anticancer agent to the area of the tumor, or into a blood vessel or lymphatic vessel that substantially directly flows into the area of the tumor, is also contemplated. In each case, the pharmaceutical composition is administered in at least an amount sufficient to achieve the endpoint, and if necessary, comprises a pharmaceutically acceptable carrier.

It is contemplated that the antibodies or immunoconjugates may be administered intratumorally, whereas any other anticancer agent may be delivered to the patient by other modes of administration (e.g., intravenously). Additionally, where multiple anticancer agents are intended to be delivered to a patient, the immunoconjugate and one or more of the other anticancer agent may be delivered intratumorally, whereas other anticancer agents may be delivered by other modes of administration (e.g., intravenously and orally).

In some embodiments, a composition may be an antibody described herein and a pharmaceutically acceptable excipient, carrier, buffer or stabilizer. In some embodiments, a composition may be an immunoconjugate described herein and a pharmaceutically acceptable excipient, carrier, buffer or stabilizer. An immunoconjugate according to the invention may be comprised in a pharmaceutical composition or medicament. Pharmaceutical compositions adapted for direct administration include, without limitation, lyophilized powders or aqueous or non-aqueous sterile injectable solutions or suspensions, which may further contain antioxidants, buffers, bacteriostats and solutes that render the compositions substantially isotonic with the blood of an intended recipient. Other components that may be present in such compositions include water, alcohols, polyols, glycerin and vegetable oils, for example. Extemporaneous injection solutions and suspensions may be prepared from sterile powders, granules and tablets. Immunoconjugate may be supplied, for example but not by way of limitation, as a lyophilized powder which is reconstituted with sterile water or saline prior to administration to the patient.

Pharmaceutical compositions of the invention may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy) propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

In another embodiment, a pharmaceutical composition comprises an antibody or immunoconjugate and one or more additional anticancer agent, optionally in a pharmaceutically acceptable carrier.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylarnino ethanol, histidine, procaine, etc.

In various embodiments of the invention, the pharmaceutical composition is directly administered to the area of the tumor(s) by, for example, local infusion during surgery, topical application (e.g., in conjunction with a wound dressing after surgery), injection, means of a catheter, means of a suppository, or means of an implant. An implant can be of a porous, non-porous, or gelatinous material, including membranes, such as sialastic membranes, or fibers. Suppositories generally contain active ingredients in the range of 0.5% to 10% by weight.

In other embodiments, a controlled release system can be placed in proximity of the target tumor. For example, a micropump may deliver controlled doses directly into the area of the tumor, thereby finely regulating the timing and concentration of the pharmaceutical composition.

In some embodiments, the pharmaceutical carrier may include, without limitation, binders, coating, disintegrants, fillers, diluents, flavors, colors, lubricants, glidants, preservatives, sorbents, sweeteners, conjugated linoleic acid (CLA), gelatin, beeswax, purified water, glycerol, any type of oil, including, without limitation, fish oil or soybean oil, or the like. Pharmaceutical compositions of the antibodies/immunoconjugates also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

For oral administration, the immunoconjugates and antibodies can be formulated readily by combining these immunoconjugates/antibodies with pharmaceutically acceptable carriers well known in the art. Such carriers enable the immunoconjugates of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of antibodies/immunoconjugates doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the immunoconjugates/antibodies can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compositions for use according to the present invention are conveniently delivered in the form of an aerosol spray presentation from pressurized packs or a nebulizer, with the use according to a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the immunoconjugates/antibodies and a suitable powder base such as lactose or starch.

The compositions of the present invention can also be formulated in rectal compositions such as suppositories or retention enemas, e.g., containing conventional suppository bases such as cocoa butter or other glycerides.

In addition to the formulations described previously, the compositions of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the immunoconjugates/antibodies can be formulated with suitable polymeric or hydrophobic materials (for example as an emulsion in an acceptable oil) or ion exchange resins, or as sparingly soluble derivatives, for example, as a sparingly soluble salt.

In transdermal administration, the compositions of the present invention, for example, can be applied to a plaster, or can be applied by transdermal, therapeutic systems that are consequently supplied to the organism.

The compositions of the present invention can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

EXAMPLES

Example 1: Method of Mapping the T-Cell Epitopes on the $V_H$ and $V_L$ Domains of the EpCAM Antibody Fragment The sequences of $V_H$-$C_H$ and $V_L$-$C_L$ domains of non-deimmunized EpCAM antibody fragment (Fab) VB5-845-WT are represented by SEQ ID NOs: 5 and 6, and have also been disclosed in U.S. Pat. No. 7,339,031, which is incorporated by reference herein. Analysis of the sequences using iTope™ was performed with overlapping 9mers spanning the proteins which were tested against each of 34 MHC class II alleles. Each 9mer was scored based on the potential 'fit' and interactions with the MHC class II molecules. The peptide scores calculated by the software lie between 0 and 1. Peptides that produced a high mean binding score (>0.55 in the iTope™ scoring function) were highlighted. If >=50% of the MHC class II binding peptides (i.e. 17 out of 34 alleles) had a high binding affinity (score >0.6), such peptides were defined as "promiscuous high affinity" MHC class II binding peptides. MHC class II binding peptides binding >=50% of alleles with a score >0.55 were defined as "promiscuous moderate affinity." The sequences were also used to interrogate the TCED™ by BLAST search in order to identify any high sequence homology to previously identified T cell epitopes.

Non-deimmunized $V_H$-$C_H$ domain is designated as wild-type (WT) $V_H$-$C_H$ (SEQ ID NO: 5) and the de-immunized $V_H$-$C_H$ domain is designated as de-immunized (DI) $V_H$-$C_H$ (SEQ ID NO: 1). Similarly, non-deimmunized $V_L$-$C_L$ domain is designated as wild-type (WT) $V_L$-$C_L$ (SEQ ID NO: 6) and the de-immunized $V_L$-$C_L$ domain is designated as de-immunized (DI) $V_L$-$C_L$ (SEQ ID NO: 2). The analysis of peptides of variable domain only-$V_H$-WT, $V_H$-DI, $V_L$-WT, and $V_L$-DI are show in FIGS. 2-6. Table 1 shows the mutated amino acids required to generate $V_H$-DI. Table 2 shows the mutated acids required to generate $V_L$-DI.

TABLE 1

| Epitope | WT amino acids | Mutated amino acids | Epitope removed (In Silico) | Comments |
|---|---|---|---|---|
| 2-11 | Q6, P9, | E6, G9, L18, | Yes | |
| 4-13 | V18, V20 | L20 | Yes | |
| 5-14 | | | Yes | |
| 12-21 | | | Yes | |
| 18-27 | | | Yes | |
| 32-41 | N31, K38 | A31, R38 | No | N35 residue critical |
| 36-45 | | | Yes | for binding, could not be mutated |
| 48-57 | M48, W50 | | No | Y53 residue critical |
| 50-59 | | | No | for binding, could not be mutated |
| 63-72 | F63, F69, L71, A75, S76, A77 | V63, I69, A71, K75, N76, T77 | No | * Change to 4D5 frame work and the presence of the epitope is due to the over predictive analysis of the in silico analysis |

TABLE 1-continued

| Epitope | WT amino acids | Mutated amino acids | Epitope removed (In Silico) | Comments |
|---|---|---|---|---|
| 79-88 | I82 | M82 | Yes | |
| 80-89 | | | | |
| 89-98 | Y91, A93, I97 | | No | Y91, A93 and I97 residues critical for binding, could not be mutated |
| 108-117 | L109 | V109 | Yes | |
| Total: 14 | | | Total: 4 * | |

TABLE 2

| Epitope | WT amino acids | Mutated amino acids | Epitope removed (In Silico) | Comments |
|---|---|---|---|---|
| 2-11 | Q6, P9, | E6, G9, L18, | Yes | |
| 4-13 | V18, V20 | L20 | Yes | |
| 5-14 | | | Yes | |
| 12-21 | | | Yes | |
| 18-27 | | | Yes | |
| 32-41 | N31, K38 | A31, R38 | No | N35 residue critical |
| 36-45 | | | Yes | for binding, could not be mutated |
| 48-57 | M48, W50 | | No | Y53 residue critical |
| 50-59 | | | No | for binding, could not be mutated |
| 63-72 | F63, F69, L71, A75, S76, A77 | V63, I69, A71, K75, N76, T77 | No | * Change to 4D5 framework and the presence of the epitope is due to the over predictive analysis of the in silico analysis |
| 79-88 | I82 | M82 | Yes | |
| 80-89 | | | | |
| 89-98 | Y91, A93, I97 | | No | Y91, A93 and I97 residues critical for binding, could not be mutated |
| 108-117 | L109 | V109 | Yes | |
| Total: 14 | | | Total: 4 * | |

Other mutations were tested but are not listed in the above tables, because they failed to express or failed in binding studies.

Example 2: Preparation of De-Immunized VB5-845

While the Fab mutations were assessed in silico with the molecule VB5-845, biological characterization was done using both the de-immunized Fab alone as well as a fusion protein containing the de-immunized Fab fragment fused to the deBouganin toxin payload on the C-terminus of the light chain. The deBouganin toxin payload (SEQ ID NO:4) was used as a tag for flow cytometry study and as a capture step for the ELISA quantification of the induced supernatant.

The mutated 845 $V_H$ and $V_L$ fragments were generated by Splice Overlapping Extension PCR method, SOE-PCR using the corresponding primers. Each $V_H$ and $V_L$ fragment was cloned into the pCR 2.1 vector and transformed into 1° F. *E. coli* cells for sequencing. The pCR 2.1 plasmid containing the correct insert was digested with an identified set of restriction enzymes, specific to either $V_H$ or $V_L$.

The $V_H$ fragment was digested with the restriction enzymes EcoRI and SacII and ligated with the SacII-$C_H$-$V_L$-$C_L$-de-Boug-XhoI fragment into the pING3302 vector, pre-digested with EcoRI and XhoI. Chemically competent 10F *E. coli* cells were transformed with the ligation reaction and a transformed colony grown for small-scale expression.

The $V_L$ fragment, digested with the restriction enzymes SalI and BsmI, was ligated with the VB6-845/pSP73 plasmid, pre-digested with the same restriction enzymes. The ligation reaction was transformed into 1° F. *E. coli* cells and, after ampicillin selection, the VB6-845/pSV73 plasmid was extracted from a colony grown overnight. The VB6-845 insert was obtained with the combination of ScaI, EcoRI and XhoI restriction enzymes and ligated into the pING3302 vector, pre-digested with the EcoRI and XhoI restriction enzymes. Chemically competent 10F *E. coli* cells were then transformed with the VB6-845/3302 ligation reaction and a transformed colony grown for small-scale expression.

To combine the mutated chains, the $V_H$ and $V_L$ fragments were digested with EcoRI-SacII and SacII-XhoI, respectively, and ligated in the presence of the pING3302 plasmid, previously digested with EcoRI and XhoI. Chemically competent 10F *E. coli* cells were transformed with the VB6-845 $V_H$+$V_L$/3302 ligation reaction and a transformed colony grown for small-scale expression.

VB5-845-DI Variant Engineering

The VB5-845 DI is represented by a heavy chain domain having an amino acid sequence of SEQ ID NO: 1 and a nucleotide sequence of SEQ ID NO: 19; and a light chain domain having an amino acid sequence of SEQ ID NO: 2 and a nucleotide sequence of SEQ ID NO: 20. The VB5-845-DI variant was engineered using the unique restriction site BssSI present in the $C_L$ kappa chain. The 845 EcoRI-$V_H$-$C_H$-$V_L$-$C_L$-BssSI fragment was ligated with the BssSI-$C_L$ kappa-XhoI fragment into the pING3302 plasmid, pre-digested with EcoRI and XhoI. Chemically competent 10F *E. coli* cells were transformed with the ligation reaction for sequencing and small-scale expression.

Small-Scale Expression

Transformed 10F cells containing the VB5-845-DI variant/3302 plasmid were inoculated into 5 mL 2-YT containing 25 μg/mL tetracycline and incubated at 37° C. with constant shaking at 225 rpm. After 16 hours of incubation, 300 μL overnight seed culture was inoculated into 30 mL TB (1% inoculum), and incubated at 37° C. with constant shaking at 225 rpm until an $OD_{600}$ of 2.0 was attained. The culture was induced with 150 μL L-Arabinose (0.1% final), and incubated at 25° C. with constant shaking at 225 rpm. At 16 hours post-induction, the culture supernatant was collected for analysis by Western blot, ELISA, and Flow Cytometry.

Expression of VB5-845-DI at 15 L Scale

Cultivation in Glycerol Minimal Media (GMM) of transformed E104 *E. coli* cells was performed in a 20 L bioreactor at 28° C., airflow and agitation of 10 SLPM and 1000 RPM, respectively, and a pH of 7.0 maintained with ammonium hydroxide. Briefly, 15 L of GMM was inoculated with 150 mL of seed culture grown in GMM containing 25 μg/mL tetracycline to an $OD_{600}$ of 2.0-2.5 in a shaking incubator set at 26° C. and 200 RPM. In the 20 L bioreactor, a spike in dissolved oxygen (DO) to ≥90% triggered feeding with 50% glycerol via the pO2 loop at a 40% DO set-point, to control the growth rate. At an $OD_{600}$ of 50, the culture was induced with a 50% glycerol feed containing L-arabinose using the same feeding strategy. After 40 hours induction, the supernatant containing VB5-845-DI was clarified by centrifugation followed by microfiltration, concentrated and diafiltered against 20 mM $NaPO_4$ buffer, pH 7.0.

Purification of a 15 L Batch Size

All chromatography columns were packed in GE healthcare re-useable column housings and depyrogenated by flowing 1 N NaOH through the columns for 35 minutes and washed with WFI until pH of the column effluent was <pH 8.0.

The theoretical isoelectric point of de-immunized VB5-845 is 8.65. The pH of the diafiltered culture supernatant was adjusted to pH 6.2 for binding to a weak cation exchange column (e.g CM sepharose prepared as per manufacturer instructions) that was previously equilibrated with 20 mM $NaPO_4$ buffer, 25 mM NaCl buffer pH 6.2. After loading, the column was washed to UV 280 nm baseline with equilibration buffer and the bound VB5-845-DI was eluted by increasing the pH and NaCl of the equilibration buffer to 20 mM $NaPO_4$ buffer, 150 mM NaCl buffer pH 7.5.

The product peak collected in the previous step was diluted 3-fold with 20 mM $NaPO_4$ buffer pH 7.0 and the final pH of the diluted solution adjusted to pH 7.5 prior to application onto to an anion exchange column (e,g Q-sepharose prepared as per manufacturer instructions) operated in flow-through mode. The column was equilibrated with 20 mM $NaPO_4$, 50 mM NaCl buffer, pH 7.5. The pH of the pooled column flow-through and wash was then adjusted to pH 6.0 for application onto the third column.

The pooled sample was then flowed through a cation exchange column (e.g SP sepharose prepared as per manufacturer instructions) previously equilibrated with 20 mM $NaPO_4$, 50 mM NaCl buffer, pH 6.0 and the effluent containing the product was collected. The pH of the effluent was adjusted to pH 7.5 and filter sterilized for long term storage at 4° C. and −20° C.

The level of expression of VB5-845-DI construct was estimated by Western blot analysis. Briefly, 16 μL of induced culture supernatant and 4 μL LDS sample buffer were loaded onto a NuPAGE 10% Bis-Tris gel. The gel was then transferred to a nitrocellulose membrane at 40V for 1 hour. After blocking and washing the membrane, the VB5-845-DI protein was detected using an anti-kappa-horseradish peroxidase antibody (1/1000) for 2 hours at room temperature. The membrane was developed using DAB, and the level of expression of VB5-845-DI constructs was compared to VB6-845 and VB5-845-WT. The specificity of the detected bands was confirmed using non-induced *E. coli* supernatant.

An ELISA was used to quantify the VB6-845 protein present in the induced culture supernatants. Briefly, an Immunolon 1B plate was coated with 10 μg/mL rabbit-anti-bouganin and incubated overnight at 4° C. After washing and blocking the plate, the VB6-845 variants supernatants, diluted 1/320, 1/640, and 1/1280 as well as a standard curve prepared from the purified VB6-845-WT antibody (25 ng/mL-0.195 ng/mL), were added to the plate and incubated for 2 hours at 22° C. Bound VB5-845-DI protein was detected using an anti-kappa-horseradish peroxidase antibody (1/1000) for 1 hour at 22° C. The plate was developed using TMB. The VB6-845-WT and the pING3302 plasmid induced culture supernatants were used as a positive and negative control, respectively.

Example 3: In Vitro Binding Assays

The binding of de-immunized VB5-845 (VB5-845-DI) and non-deimmunized VB5-845 (VB5-845-WT) antibody fragments were evaluated on cancer cell line CAL-27 by flow cytometry. The purified VB5-845 variants (DI and WT) were incubated at 1 μg/mL with $0.3\times10^6$ tumor cells for 2 hours on ice. After washing with PBS-5% FBS, a biotinylated goat-anti-human IgG (H&L) antibody (1/200) was added to the cells and incubated for 1 hour on ice. The cells were washed with PBS-5% FBS and streptavidin-cychrome was added for 30 minutes on ice to detect cell-bound VB5-845 proteins (FIG. 7).

Figure 8:
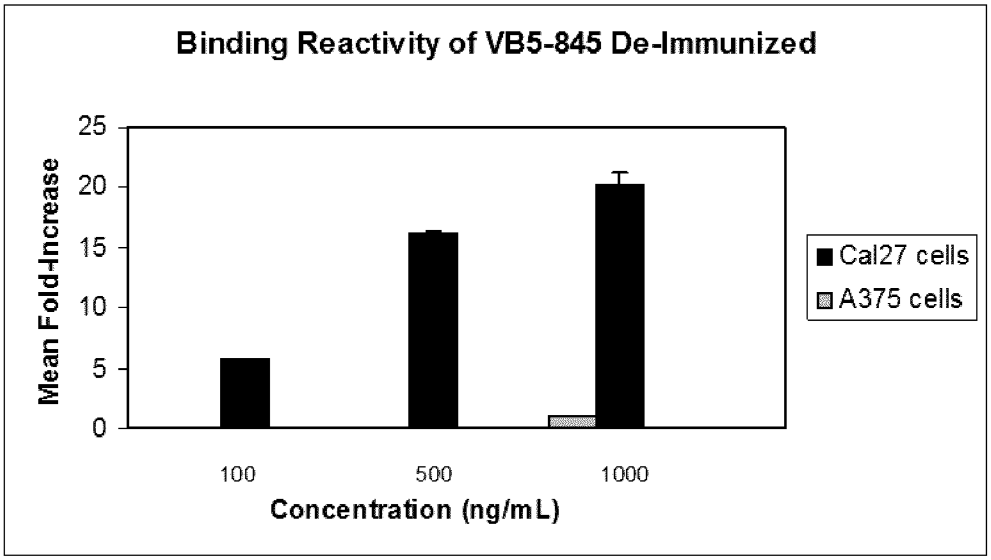
FIG. 8 shows dose-dependent binding of VB5-845-DI to EpCAM-positive H&N squamous cell carcinoma cell line Cal27. Binding is expressed as the mean fold-increase in median fluorescence over the PBS control, by flow cytometry.

FIG. 8 shows dose-dependent binding of VB5-845-DI to EpCAM-positive H&N squamous cell carcinoma cell line Cal-27. No binding was observed against the EpCAM-negative melanoma A375. Binding is expressed as the mean fold-increase in median fluorescence over the PBS control by flow cytometry.

Example 4: Binding Affinity

Figure 9:
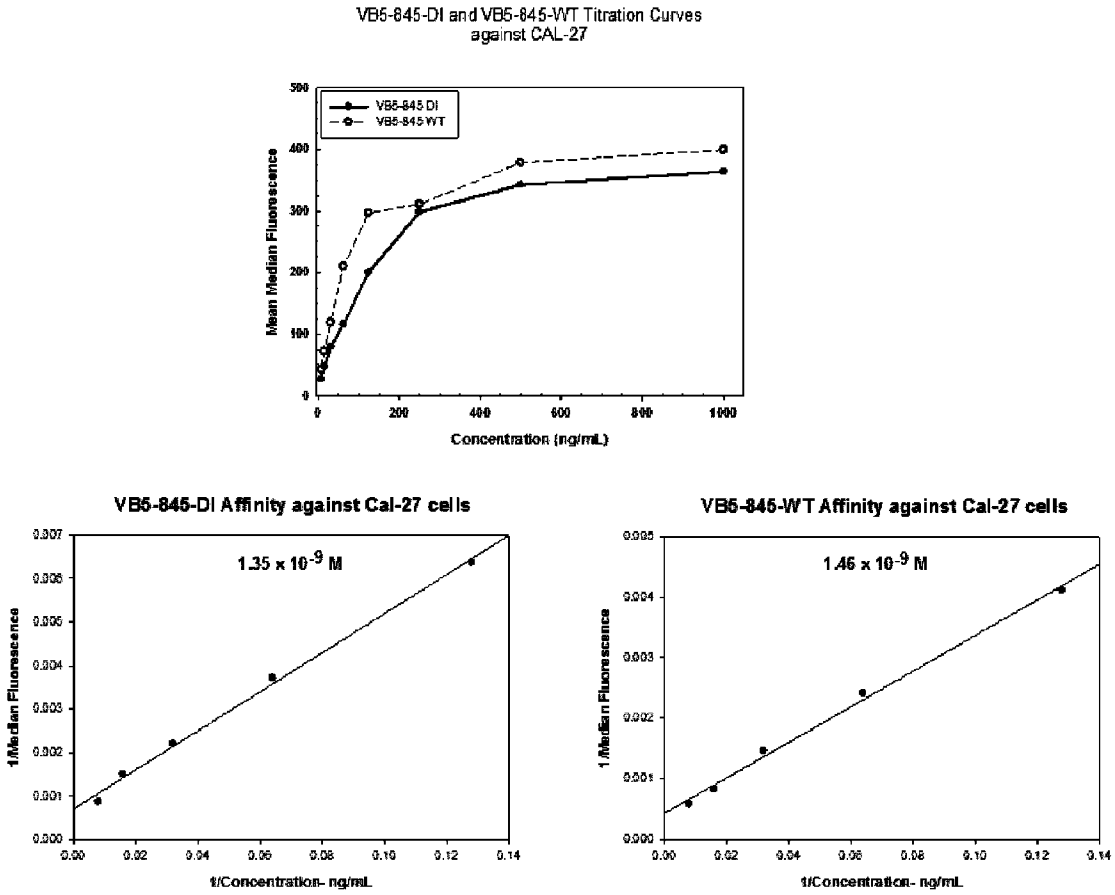
FIG. 9 shows binding affinity of the VB5-845-WT and VB5-845-DI against Cal-27 cells, as measured by flow cytometry.

The flow cytometry was used to measure the binding affinity of the VB5-845-WT and VB5-845-DI. Briefly, VB5-845 proteins were incubated at concentrations ranging from 3.2 ng/mL to 1000 ng/mL with $0.2\times10^6$ CAL 27 cells on ice for 2 hours. After washing with PBS-5% FBS, a biotinylated goat-anti-human IgG antibody was added and incubated for 1 hour on ice. The cells were washed with PBS-5% FBS and streptavidin-cychrome was added for 30 minutes on ice to detect cell-bound VB5-845. Values and graphical analysis were generated using Sigma Plot (Jandel Scientific, San Rafael, Calif.). The inverse of the determined median fluorescence was plotted as a function of the inverse of antibody concentration to determine KD by the Lineweaver-Burk method. A plot was generated and the KD was calculated from the slope of the curve. The dissociation constant, KD value, was determined by the following equation: 1/F=1/Fmax+(KD/Fmax) (1/Fab), where F=background subtracted median fluorescence and Fmax was calculated from the plot (FIG. 9).

Example 5: Competition Assays

Figure 10:
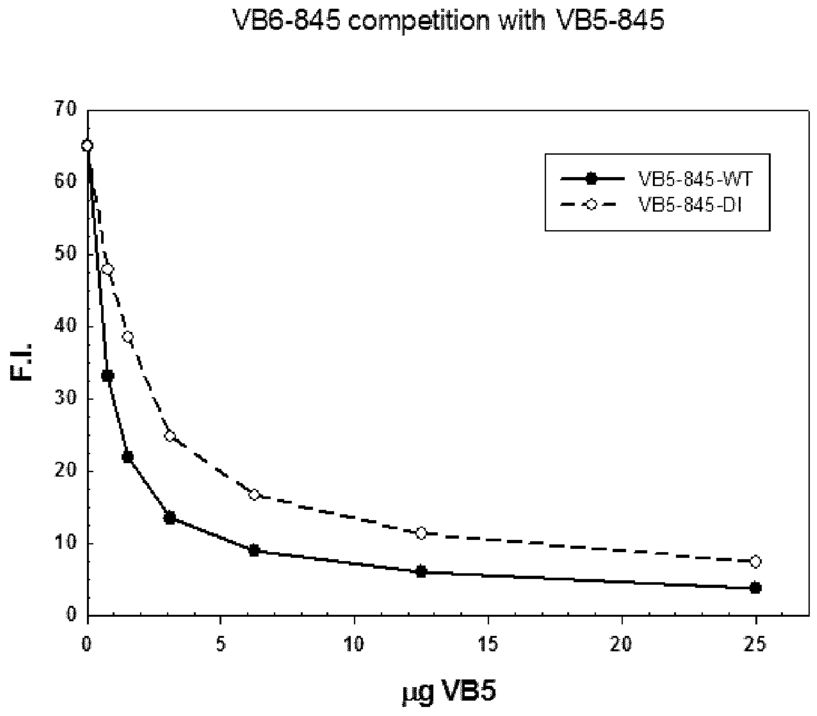
FIG. 10 shows competition assays between VB5-845 variants and VB6-845 by flow cytometry.

The ability of the VB5-845 variants (VB5-845-DI and VB5-845-WT) to compete with VB6-845 for binding to CAL 27 tumor cells was determined by flow cytometry. VB6-845 is an immunoconjugate attached to de-immunized bouganin toxin and has been described in U.S. Pat. No. 7,339,031 and is incorporated herein by reference. VB5-845 variants and VB6-845 were incubated together in 150 µL with $0.2\times10^6$ tumor cells for 2 hours on ice. The concentration of VB6-845 was held constant at 1 µg/mL while the concentration of VB5-845 variants was increased from 781 ng/mL to 25 µg/mL. Bound cell-surface VB6-845 was detected with a mouse anti-de-bouganin antibody followed by a goat anti-mouse H&L coupled to FITC (FIG. 10).

Example 6: EpiScreen Analysis of Wild-Type Vs. De-Immunized Clone

Preparation and Selection of Donor PBMC

Peripheral blood mononuclear cells (PBMC) are isolated from healthy community donorbuffy coats (from blood drawn within 24 hours) obtained from the UK National Blood Transfusion Service (Addenbrooke's Hospital, Cambridge, UK) and according to approval granted by Addenbrooke's Hospital Local Research Ethics Committee. PBMC are isolated from buffy coats by Lymphoprep (Axis-shield, Dundee, UK) density centrifugation and CD8+ T cells are depleted using CD8+ RosetteSep™ (StemCell Technologies Inc, London, UK). Donors are characterized by identifying HLA-DR haplotypes using an HLA SSP-PCR based tissue-typing kit (Biotest, Solihull, UK). T-cell responses to a control antigen (Keyhole Limpet Haemocyanin (KLH), [Pierce (Perbio), Cramlington, UK]), as well as peptides derived from Influenza A and Epstein Barr viruses are also determined. PBMC are then frozen and stored in liquid nitrogen until required.

A cohort of 51 donors are selected to best represent the number and frequency of HLA-DR allotypes expressed in the world population. Analysis of the allotypes expressed in the cohort against those expressed in the world population will reveal that coverage of >80% is achieved and that all major HLA-DR allotypes (individual allotypes with a frequency >5% expressed in the world population) are well represented.

EpiScreen™ Time Course T-Cell Proliferation Assays

PBMCs from each donor are thawed, counted and viability assessed. Cells are revived in room temperature AIM-VR culture medium, washed and resuspended in AIM-VR to $4\text{-}6\times10^6$ PBMC/ml. For each donor, bulk cultures are established in which 1 mL proliferation cell stock is added to the appropriate wells of a 24 well plate. 0.5 mL of culture medium and 0.5 mL of each diluted sample are added to the PBMC to give a final concentration of 0.3 µM. For each donor, a reproducibility control (cells incubated with 100 µg/ml KLH), a positive control (cells incubated with 2.5 µg/ml PHA) and a culture medium-only well are also included. Cultures are incubated for a total of 8 days at 37° C. with 5% $CO_2$. On days 5, 6, 7 and 8, the cells in each well are gently resuspended, and 3×100 µl aliquots transferred to each well of a round bottomed 96 well plate. The cultures are pulsed with 0.75 µCi [$^3$H]-Thymidine (Perkin ElmerR, Beaconsfield, UK) in 100 µl AIM-VR culture medium and incubated for a further 18 hours before harvesting onto filter mats (Perkin ElmerR) using a Skatron Micro 96S-10056 cell harvester. Counts per minute (cpm) for each well are determined by Meltilex™ (Perkin ElmerR) scintillation counting on a 1450 Microbeta Wallac Trilux Liquid Scintillation Counter (Perkin ElmerR) in paralux, low background counting.

EpiScreen™ IL-2 ELISpot Assays

Identical donors to those used in the proliferation assay are also used for the IL-2 ELISpot assay. Cells are thawed and revived as described above. ELISpot plates (Millipore, Watford, UK) are pre-wetted and coated overnight with 100 µl/well IL-2 capture sample (R&D Systems, Abingdon, UK) in PBS. Plates are then washed 3 times in PBS, incubated overnight in blocking buffer (1% BSA in PBS) and washed in AIM-VR medium. The cell density for each donor is adjusted to $4\text{-}6\times10^6$ PBMC/ml in AIM-VR culture medium and 100 µL of cells are added to each well. 50 µL of samples and controls are added to the appropriate wells as well as 50 µL of AIMV to bring the total volume to 200 µL/well. Samples are tested in sextuplicate cultures and, for each donor, a negative control (AIMV R medium alone), no cells control and a mitogen positive control (PHA at 2.5 µg/ml—used as an internal test for ELISpot function and cell viability), are also included on each plate. After an 8 day incubation period, ELISpot plates are developed by sequential washing in $dH_2O$ and PBS (×3) prior to the addition of 100 µL filtered, biotinylated detection sample (R&D Systems) in PBS/1% BSA. Following incubation at 37° C. for 1.5 hours, plates are further washed in PBS (×3) and 100 µL filtered streptavidin-AP (R&D Systems) in PBS/1% BSA was added for 1.5 hours (incubation at room temperature). Streptavidin-AP is discarded and plates are washed in PBS (×4). 100 µL BCIP/NBT substrate (R&D Systems) is added to each well and incubated for 30 minutes at room temperature. Spot development is stopped by washing the wells and the backs of the wells three times with $dH_2O$. Dried plates are scanned on an ImmunoscanR analyser and spots per well (spw) are determined using ImmunoscanR version 4 software.

EpiScreen™ Data Analysis

For proliferation and IL-2 ELISpot assays, an empirical threshold of a stimulation index (SI) equal to or greater than 2 (SI≥2.00) has been previously established, whereby samples inducing responses above this threshold are deemed positive (borderline SIs ≥1.90 are also highlighted). Extensive assay development and previous studies have shown that this is the minimum signal-to-noise threshold allowing maximum sensitivity without detecting large numbers of false positive responses or omitting subtle immunogenic events. For both proliferation (n=3) and IL-2 ELISpot data (n=6) sets, positive responses are defined by statistical and empirical thresholds as follows: (1) Significance ($p<0.05$) of the response by comparing cpm or spw of test wells against medium control wells using unpaired two sample student's t-test; (2) Stimulation index greater than or equal to 2 (SI≥2.00), where SI=mean of test wells (cpm or spw)/baseline (cpm or spw). Data presented in this way is indicated as SI≥2.00, $p<0.05$. In addition, intra-assay variation is assessed by calculating the coefficient of variance and standard deviation (SD) of the raw data from replicate cultures.

Example 7: Molecular Engineering and Expression of De-Immunized VB6-845 (Algo Clone)

Experimental Design

VB6-845 Variant Engineering

The mutated 845 $V_H$ and $V_L$ fragments were generated by Splice Overlapping Extension PCR method, SOE-PCR. Each $V_H$ and $V_L$ fragment was cloned into the pCR 2.1 vector and transformed into 1° F. *E. coli* cells for sequencing. The pCR 2.1 plasmid containing the correct insert was digested with an identified set of restriction enzymes, specific to either $V_H$ or $V_L$.

The $V_H$ fragment was digested with the restriction enzymes EcoRI and SacII and ligated with the SacII-$C_H$-$V_L$-$C_L$-de-Boug-XhoI fragment into the pING3302 vector, pre-digested with EcoRI and XhoI. Chemically competent 10F *E. coli* cells were transformed with the ligation reaction and a transformed colony grown for small-scale expression.

The $V_L$ fragment, digested with the restriction enzymes SalI and BsmI, was ligated with the VB6-845 pSP73 plasmid, pre-digested with the same restriction enzymes. The ligation reaction was transformed into 1° F. *E. coli* cells and, after ampicillin selection, the VB6-845/pSV73 plasmid was extracted from a colony grown overnight. The VB6-845 insert was obtained with the combination of ScaI, EcoRI and XhoI restriction enzymes and ligated into the pING3302 vector, pre-digested with the EcoRI and XhoI restriction enzymes. Chemically competent 10F *E. coli* cells were then transformed with the VB6-845/3302 ligation reaction and a transformed colony grown for small-scale expression.

To combine the mutated chains, the $V_H$ and $V_L$ fragments were digested with EcoRI-SacII and SacII-XhoI, respectively, and ligated in the presence of the pING3302 plasmid, previously digested with EcoRI and XhoI. Chemically competent 10F *E. coli* cells were transformed with the VB6-845 $V_H$+$V_L$/3302 ligation reaction and a transformed colony grown for small-scale expression.

VB5-845 Algo Engineering

The VB5-845-Algo Fab is represented by a heavy chain domain having an amino acid sequence of SEQ ID NO:11 and a nucleotide sequence of SEQ ID NO: 23; and a light chain domain having an amino acid sequence of SEQ ID NO: 12 and a nucleotide sequence of SEQ ID NO: 24. The VB5-845-Algo was engineered using the unique restriction site BssSI present in the $C_L$ kappa chain. The 845 EcoRI-$V_H$-$C_H$-$V_L$-$C_L$-BssSI fragment was ligated with the BssSI-$C_L$ kappa-XhoI fragment into the pING3302 plasmid, pre-digested with EcoRI and XhoI. Chemically competent 10F *E. coli* cells were transformed with the ligation reaction for sequencing and small-scale expression.

Small Scale Expression

Transformed 10F cells containing either the VB6-845-Algo/3302 plasmid or the VB5-845-Algo/3302 plasmid were inoculated into 5 mL 2-YT containing 25 μg/mL tetracycline and incubated at 37° C. with constant shaking at 225 rpm. After 16 hours of incubation, 300 μL overnight seed culture was inoculated into 30 mL TB (1% inoculum), and incubated at 37° C. with constant shaking at 225 rpm until an $OD_{600}$ of 2.0 was attained. The culture was induced with 150 μL L-Arabinose (0.1% final), and incubated at 25° C. with constant shaking at 225 rpm. At 16 hours post induction, the culture supernatant was collected for analysis by Western blot, ELISA, and Flow Cytometry.

Western Blot Analysis

The level of expression of the VB6-845 and VB5-845-Algo was estimated by Western blot analysis. Briefly, 16 μL of induced culture supernatant and 4 μL LDS sample buffer were loaded onto a NuPAGE 10% Bis-Tris gel. The gel was then transferred to a nitrocellulose membrane at 40V for 1 hour. After blocking and washing the membrane, the VB6/VB5-845-Algo protein was detected using an anti-kappa-horseradish peroxidase antibody (1/1000) for 2 hours at room temperature. The membrane was developed using DAB, and the level of expression of the VB6/VB5-845-Algo were compared to VB6/VB5-845 wild types (WT), respectively. The specificity of the detected bands was confirmed using non-induced *E. coli* supernatant.

Quantification by ELISA

An ELISA was used to quantify the VB6-845 protein present in the induced culture supernatants. Briefly, an Immunolon1B plate was coated with 10 μg/mL rabbit-anti-bouganin and incubated overnight at 4° C. After washing and blocking the plate, the VB6-845 supernatants, diluted 1/320, 1/640, and 1/1280 as well as a standard curve prepared from the purified VB6-845 antibody (25 ng/mL-0.195 ng/mL), were added to the plate and incubated for 2 hours at 22° C. Bound VB6-845 protein was detected using an anti-kappa-horseradish peroxidase antibody (1/1000) for 1 hour at 22° C. The plate was developed using TMB. The VB6-845-WT and the pING3302 plasmid induced culture supernatants were used as a positive and negative control, respectively.

Binding Reactivity Measured by Flow Cytometry

VB6-845 Induced Culture Supernatants: The reactivity of the VB6-845 constructs was assessed by flow cytometry using EpCAM-positive human squamous cell carcinoma CAL 27. Using the ELISA quantification, the volumes of the VB6-845 induced supernatant were adjusted to the lowest concentration and incubated with $0.2\times10^6$ tumor cells for 2 hours on ice. After washing with PBS-5% FBS, a rabbit-anti-bouganin antibody (1/100) was added to the cells and incubated for 1 hour on ice. The cells were washed with PBS-5% FBS, and a goat-anti-rabbit antibody coupled to FITC (1/100) was added for 30 minutes on ice to detect cell-bound VB6-protein. VB6-845-WT and the pING3302 plasmid induced culture supernatants were used as a positive and a negative control respectively.

Purified VB5-845: The binding reactivity of purified VB5-845 variants to the tumor cell line CAL 27 was measured by flow cytometry. The purified VB5-845 variants were incubated at 1 μg/mL with $0.3\times10^6$ tumor cells for 2 hours on ice. After washing with PBS-5% FBS, a biotinylated goat-anti-human IgG (H&L) antibody (1/200) was added to the cells and incubated for 1 hour on ice. The cells were washed with PBS-5% FBS and streptavidin-cychrome was added for 30 minutes on ice to detect cell-bound VB5-protein. VB5-845-WT was used as a positive control.

Purified VB6-845: The binding reactivity of purified VB6-845-Algo at 100 ng/mL was measured as described previously. The cytotoxicity was measured with a MTS assay using EpCAM-positive and negative cell lines. VB6-845-WT was used as a positive control.

Binding Affinity

Flow cytometry was used to measure the binding affinity of the VB5-845-Algo. Briefly, VB5-845-Algo was incubated at concentrations ranging from 3.2 ng/mL to 1000 ng/mL with $0.2\times10^6$ CAL 27 cells on ice for 2 hours. After washing with PBS-5% FBS, a biotinylated goat-anti-human IgG antibody (1/200) was added and incubated for 1 hour on ice. The cells were washed with PBS-5% FBS and streptavidin-cychrome (1/120) was added for 30 minutes on ice to detect cell-bound VB5-845-Algo. Values and graphical analysis were generated using Sigma Plot (Jandel Scientific, San Rafael, Calif.). The inverse of the determined median fluorescence was plotted as a function of the inverse of antibody concentration to determine KD by the Lineweaver-Burk method. A plot was generated and the KD was calculated from the slope of the curve. The dissociation constant, KD value, was determined by the following equation: 1/F=1/Fmax+(KD/Fmax) (1/Fab), where F=background subtracted median fluorescence and Fmax was calculated from the plot.

Competition Assay with VB6-845 or VB5-845-WT

The ability of the VB5-845-Algo to compete with VB6-845 for binding to CAL 27 tumor cells was determined by flow cytometry. VB5-845-Algo and VB6-845 were incubated together in 150 μL with $0.3\times10^6$ tumor cells for 2 hours on ice. The concentration of VB6-845 was held constant at 1 μg/mL while the concentration of VB5-845-Algo was increased from 17.8 μg/mL to 71 μg/mL. The cells were washed with PBS-5% FBS, and a rabbit-anti-bouganin antibody (1/100) added to the cells and incubated for 1 hour on ice. After washing with PBS-5% FBS, a goat-anti-rabbit antibody coupled to FITC (1/100) was added for 30 minutes on ice to detect cell-bound VB6 protein. VB4-845 was used as a positive control to compete with VB6-845 for the binding to the tumor cell line CAL 27.

Serum Stability

The serum stability of the VB5-845 and VB6-845 variants was determined by Western blot analysis. Briefly, variants were added at a concentration of 80 μg/mL in 500 μL human serum and incubated at 37° C., 5% $CO_2$ for 24 hours. At 0 hour, 3 hours, 6 hours, and 24 hours, samples were vortex and a 45 μL aliquot was removed and stored at −20° C. in presence of 15 μL LDS. The Western blot was performed as above, loading 200 ng/well of variant. The VB5-845 or VB6-845 proteins were detected using a rabbit-anti-4D5 antibody (1/1000) for 45 minutes at room temperature, followed by an anti-rabbit-horseradish peroxidase antibody (1/2000) for 45 minutes at room temperature. The membrane was developed with DAB. Purified VB5-845 or VB6-845 were used as positive controls.

Thermostability

Flow cytometry was used to determine the thermo-stability of the VB5-845 and VB6-845 variants. The VB5-845 and VB6-845 variants were added at a concentration of 80 μg/mL in PBS and incubated at 37° C., 5% $CO_2$ for 24 hours. At 0 hour, 3 hours, 6 hours and 24 hours, a 25 μL aliquot was removed and stored at −20° C. for analysis by flow cytometry. For testing, the VB5-845 and VB6-845 variant samples were diluted to 1 μg/mL and 100 ng/mL, respectively in 150 μL PBS-5% FBS and incubated with $0.3\times10^6$ cells for 2 hours on ice. After washing with PBS-5% FBS, a goat-anti-human IgG (H+L) biotinylated antibody (1/200) was added and incubated for 1 hour on ice. After washing, PE-Cy5 streptavidin fluorochrome (1/120) was added to detect VB5-845 cell surface binding. The purified VB5-845-WT and VB6-845-WT were used as a positive control.

T-Cell Proliferation of VB5-845-Algo

VB5-845-Algo and VB5-845 ability to induce T-cell proliferation was measured by gating on the CD3+CD4+ by flow cytometry. The proliferation with or without the Fab proteins was analyzed by the fluorescence intensity of EdU-A488, a DNA incorporation marker. The data was expressed as Stimulation indices (SI-values) which corresponds to the ratio of the number of activated CD3+CD4+ T-lymphocytes in Fab treated versus untreated wells.

Results

The Epibase® analysis identified the potential T-cell epitopes present in the heavy and light chains. The proposed changes are amino acids that correspond to germline sequences and were classified as "safe or risky mutations". Because according to the number of changes, it was not feasible to evaluate the effect of a single point mutation on the expression and biological activity. Therefore, safe mutations were grouped and introduced with two consecutive rounds of SOE-PCR. However, because according to the incertitude for positions $V_H38$ and $V_L50$, chains containing either mutated or wild-type residues were created. Once the sequences were verified, the mutated chains were cloned into the VB6-845 dicistronic unit and expressed in presence of their respective wild-type counterpart. If the level of expression and biological activity were comparable to WT, then mutated heavy and light chains were combined and tested. For the "risky mutations", $V_H53$, $V_H93$ and $V_H98$ were first evaluated as a single point mutation. If determined suitable, then they were incorporated within the final $V_H$ construct.

Molecular Engineering of VB6-845 First Generation

1) Engineering and Testing of VB6-845 First Version of the "Safe Mutations":

$V_H$-algo: Two successive rounds of SOE-PCR were required to introduce all the mutations. As seen in Table 3, the $V_H$-Ir clone contained the FR1 and part of the FR3 mutations. The $V_H$-Ir template was then employed in the next SOE-PCR reaction to create $V_H$-IIr which contains all the mutations and in case of $V_H$-IIr-K38, position 38 was unchanged. The sequencing reaction performed on the final SOE-PCR reaction also revealed that one of the sequenced clones, named IIr-CDR1, contains all the mutated amino acids except for the CDR1 and FR2 region. The expression level of the mutated heavy chains in presence of the WT light chain was similar to the WT. In addition, the biological activity, measured by flow cytometry, was unchanged compared to WT. Of note, the higher median fluorescence obtained with some of the variants could be the result of the underestimation of the concentration obtained by ELISA.

TABLE 3

| VH-algo mutations and biological activity | | | | | | | |
|---|---|---|---|---|---|---|---|
| clone | FR1 | CDR1 | FR2 | FR3 | FR4 | ELISA (μg/mL) | MF |
| WT | V5 | N31-N35 | K38 | T68-S74-A75-A77-N82a-A84 | L109 | 1.9 | 100 |
| Ir | **Q5** | N31-N35 | K38 | **E68**-S74-A75-A77-**Q82a-E84** | L109 | 1.5 | 123 |
| IIr | **Q5** | **A31-S35** | **R38** | **E68-H74-N75-S77-Q82a-E84** | **V109** | 1.3 | 117 |
| IIr-K38 | **Q5** | **A31-S35** | K38 | **E68-H74-N75-S77-Q82a-E84** | **V109** | 1.4 | 120 |
| IIr-CDR1 | **Q5** | N31-N35 | K38 | **E68-H74-N75-S77-Q82a-E84** | **V109** | 1.7 | 141 |

Amino acids in bold correspond to the mutated residues. The reported median fluorescence, MF, is an average of two independent experiments and is expressed as % of WT. Number as per Kabat nomenclature.

$V_L$-Algo: The light chains containing the CDR1/A50-CDR2/FR4 or CDR1/Q50-CDR2/FR4 mutations were introduced by the first SOE-PCR reaction. In contrast to the $V_H$ strategy, a construct containing only the FR2 mutations was engineered and tested separately. The biological activity of Ir-A50 clone decreased significantly demonstrating that the A50 mutation was detrimental for VB6-845 binding to EpCAM. As a consequence, the FR2 mutations were only added to Ir-Q50 light chain. When tested, the level of expression and biological activity of IIr-Q50 was 70 and 44% lower than the WT, respectively. Of note, the expression level and biological activity were only partially restored by reversing position 41 to WT amino acid.

TABLE 4

| VL-algo mutations and biological activity | | | | | | |
|---|---|---|---|---|---|---|
| Clone | CDR1 | FR2 | CDR2 | FR4 | ELISA (μg/mL) | MF |
| WT | R24 | G41-K42 | Q50-M51-N53-A55 | L106 | 1.47 | 100 |
| Ir-A50 | **K24** | G41-K42 | **A50-A51-S53-Q55** | **I106** | 1.42 | 20 |
| Ir-Q50 | **K24** | G41-K42 | Q50-**A51-S53-Q55** | **I106** | 1.15 | 93 |
| FR2 | R24 | **D41-Q42** | Q50-M51-N53-A55 | L106 | 0.91 | 84 |
| IIr-Q50 | **K24** | **D41-Q42** | Q50-**A51-S53-Q55** | **I106** | 0.44 | 56 |

Amino acids in bold correspond to the mutated residues. The reported median fluorescence, MF, is an average of two independent experiments and is expressed as % of WT. Numbered as per Kabat nomenclature.

$V_H$-$V_L$-algo: Based on the results described above, $V_H$-IIr and $V_L$-Ir-Q50 were selected, combined and expressed as a VB6-845 recombinant fusion protein. As seen in Table 5, more than 66% of the biological activity was lost suggesting that some mutations have affected the $V_H$-$V_L$ interface. To pinpoint the problematic area, $V_H$-Ir and $V_H$-IIr-CDR1 were also engineered in presence of $V_L$-Ir-Q50 and tested. The biological activity of VB6-845-($V_H$-IIr-CDR1/$V_L$-Ir-Q50) was partially restored suggesting that mutations within the CDR1 regions may have in part altered the $V_H$-$V_L$ interface.

TABLE 5

| $V_H$-$V_L$ Algo testing | | | |
|---|---|---|---|
| $V_H$ | $V_L$ | ELISA (μg/mL) | MF |
| WT | WT | 1.56 | 100 |
| IIr | Ir-Q50 | 1.2 | 34 |

TABLE 5-continued

| $V_H$-$V_L$ Algo testing | | | |
|---|---|---|---|
| $V_H$ | $V_L$ | ELISA (μg/mL) | MF |
| Ir | Ir-Q50 | 1.46 | 82 |
| IIr-CDR1 | Ir-Q50 | 2.05 | 78 |

The reported median fluorescence, MF, is an average of two independent experiments and is expressed as % of WT.

2) Engineering and Testing of the VB6-845 "Risky Mutations"

VB6-845 constructs containing a single "risky" point mutation were engineered by SOE-PCR and tested. As seen in Table 6, only position K98Q did not affect biological activity.

TABLE 6

| $V_H$ Algo, "risky mutations" and biological activity | | | | | |
|---|---|---|---|---|---|
| clone | CDR2 | FR3 | CDR3 | ELISA (μg/mL) | MF |
| WT | Y53 | A93 | K98 | 3.2 | 100 |
| $V_H$-N53 | N53 | A93 | K98 | 4.0 | 23 |
| $V_H$-S93 | Y53 | S93 | K98 | 2.7 | 35 |
| $V_H$-Q98 | Y53 | A93 | Q98 | 3.2 | 108 |

The reported median fluorescence, MF, is an average of two independent experiments and is expressed as % of WT. Numbered as per Kabat nomenclature.

3) Engineering and Testing of VB6-845 Second Version

Based on the results described above, some adjustments were undertaken. For the $V_H$ domain, position 35 was reversed to WT. For the $V_L$ domain, the difficulty of mutating the FR2 and position 50 led to a different set of mutations for the FR2 and CDR2 regions.

$V_H$-algo, second version: Position 35 was reversed to an asparagine residue using the IIr insert as a template in the SOE-PCR reaction. As expected, no differences in expression level or biological activity were observed when engineered with the wild-type light chain (Table 7). Similarly, the addition of the CDR3 mutation, Q98 to the IIr-N35 did not alter expression or biological activity.

TABLE 7

| VH-algo second version, mutations and biological activity | | | | | | | | |
|---|---|---|---|---|---|---|---|---|
| clone | FR1 | CDR1 | FR2 | FR3 | CDR3 | FR4 | ELISA (μg/mL) | MF |
| WT | V5 | N31-N35 | K38 | T68-S74-A75-A77-N82a-A84 | K98 | L109 | 1.2 | 100 |
| IIr | **Q5** | **A31-S35** | **R38** | **E68-H74-N75-S77-Q82a-E84** | K98 | **V109** | 1.35 | 72 |
| IIr-CDR1 | **Q5** | N31-N35 | K38 | **E68-H74-N75-S77-Q82a-E84** | K98 | **V109** | 1.23 | 117 |
| IIr-N35 | **Q5** | **A31-**N35 | **R38** | **E68-H74-N75-S77-Q82a-E84** | K98 | **V109** | 1.2 | 109 |
| IIr-N35-Q98 | **Q5** | **A31-**N35 | **R38** | **E68-H74-N75-S77-Q82a-E84** | **Q98** | **V109** | 1.2 | 100 |

Amino acids in bold correspond to the mutated residues. The reported median fluorescence, MF, is an average of two independent experiments and is expressed as % of WT. Numbered as per Kabat nomenclature.

$V_L$-algo, second version: Both light chains containing either the FR2 (H39-S42) or CDR2 (E51-H53-Q55) mutations showed decreased binding when tested as a VB6-845 molecule. This effect was further amplified when combined with the CDR1 and FR4 mutations as a final $V_L$ construct (IIr/FR2/CDR2). Of note, it is also possible that the light chain mutations will only be functional in presence of the mutated $V_H$. However, as a contingency, a light chain (IIr-KSHI) containing only few mutations which will have the greatest impact on depleting the T-cell epitopes was also engineered and the biological activity was found similar to VB6-845 WT.

TABLE 8

| $V_L$ algo second version, mutations and biological activity | | | | | | |
|---|---|---|---|---|---|---|
| clone | CDR1 | FR2 | CDR2 | FR4 | ELISA (μg/mL) | MF |
| WT | R24 | K39-K42 | Q50-M51-N53-A55 | L106 | 0.69 | 100 |
| CDR2 | R24 | K39-K42 | Q50-**E51-H53-Q55** | L106 | 0.78 | 70 |
| FR2 | R24 | **H39-S42** | Q50-M51-N53-A55 | L106 | 0.6 | 68 |
| Ir-CDR2 | **K24** | K39-K42 | Q50-**E51-H53-Q55** | **I106** | 0.73 | 57 |
| IIr-FR2-CDR2 | **K24** | **H39-S42** | Q50-**E51-H53-Q55** | **I106** | 0.29 | 45 |
| IIr-KSHI | **K24** | K39-**S42** | Q50-M51-**H53-**A55 | **I106** | 0.63 | 89 |

Amino acids in bold correspond to the mutated residues. The reported median fluorescence, MF, is an average of two independent experiments and is expressed as % of WT. Numbered as per Kabat nomenclature.

$V_H$-$V_L$-algo, second version: The final $V_H$ chain, IIr-N35-Q98 was combined with $V_L$-Ir-CDR2, $V_L$-IIr-FR2-CDR2 and $V_L$-IIr-KSHI. As seen in table 7, only the VB6-845 construct containing the combined $V_H$-IIr-N35-Q98 and $V_L$-IIr-KSHI had a similar expression level and biological activity to the WT and is referred as VB6-845-Algo. The other combinations yield significant loss in expression and binding to EpCAM.

TABLE 9

| $V_H$-$V_L$ Algo second version testing | | | |
|---|---|---|---|
| $V_H$ | $V_L$ | ELISA (μg/mL) | MF |
| WT | WT | 1.2 | 100 |
| IIr-N35-Q98 | Ir-CDR2 | 0.76 | 45 |
| IIr-N35-Q98 | IIr-FR2-CDR2 | 0.34 | 38 |
| IIr-N35-Q98 | IIr-KSHI | 0.9 | 94 |

TABLE 9-continued

The reported median fluorescence, MF, is an average of two independent experiments and is expressed as % of WT. Numbered as per Kabat nomenclature.

Biological Activity of VB5-845-Algo

To prevent deBouganin interference with the T-cell proliferation assay, the VB5-845 Fab version of VB6-845-Algo was created, expressed and purified. Purified VB5-845-Algo Fab protein was submitted to various biological testing and the data compared to VB5-845-WT.

Competition Assay

Figure 13:
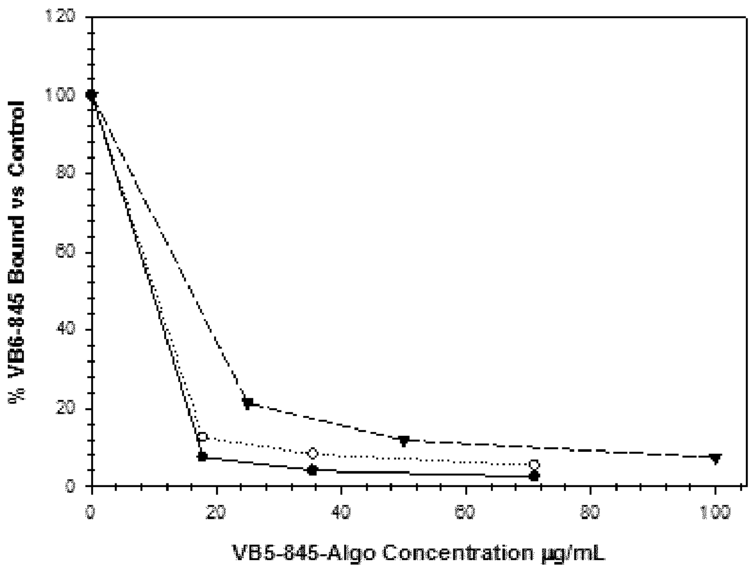
FIG. 13 discloses VB6-845 Competition assay with VB5-845-Algo (open circle). Black circle and black triangle correspond to VB5-845-WT and VB4-845, respectively.

To ensure that the specificity was not altered, the ability of VB5-845-Algo to compete with VB6-845 binding to EpCAM-positive CAL-27 cells was tested. As shown in FIG. 13, VB5-845-Algo (open circle) competed VB6-845 binding. VB4-845 and VB5-845-WT were used as positive controls.

Human Serum Stability

Figure 14:
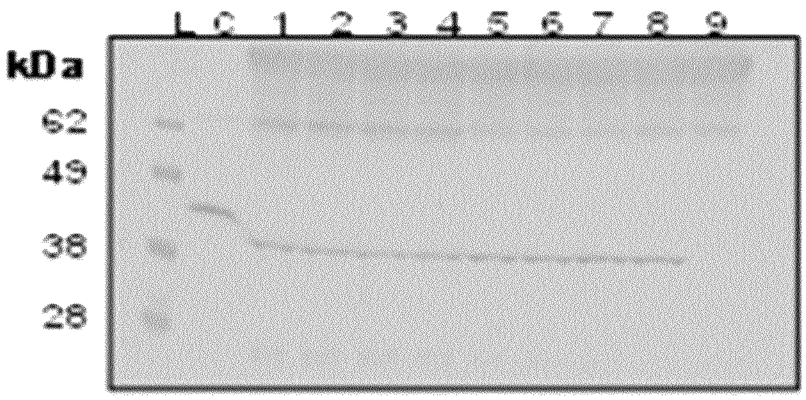
FIG. 14 shows Western blot analysis of VB5-845-Algo serum stability. Lanes 1 to 4 correspond to VB5-845-WT at 0, 3, 6 and 24 hours. Lanes 5 to 8 to VB5-845-Algo 0, 3, 6 and 24 hours. Lane 9 is human serum only. L: Ladder and C: Control.

To demonstrate that the mutations did not created proteolytic sites, VB5-845-Algo and VB5-845-WT were incubated in human serum at 37° C. to a maximum of 24 hours. The stability of the VB5 proteins was assessed by Western blot analysis. As shown in FIG. 14, the analysis revealed no changes in the intensity suggesting that both VB5-845 proteins remained intact in human serum.

Thermo-Stability

Figure 15:
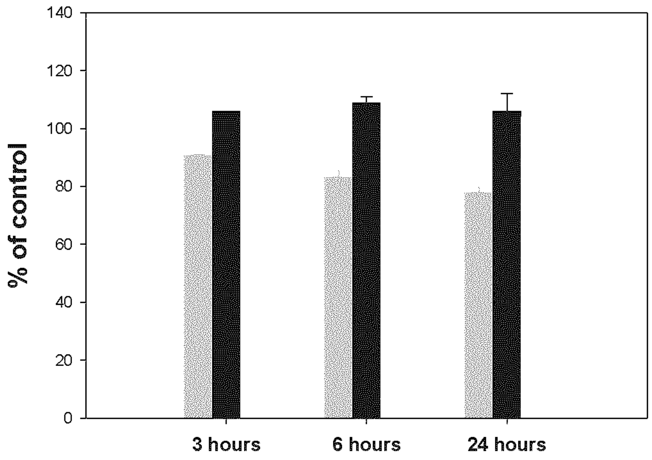
FIG. 15 shows thermo-stability of VB5-845-WT (grey) and VB5-845-Algo (black), expressed as a % of the 0 hour of an average duplicate.

To ensure that the mutations did not affect the thermostability of the $V_H$-$V_L$ interface, the biological activity of VB5-845-Algo was assessed by flow cytometry after incubation at 37° C. in 1×PBS for 0, 3, 6 and 24 hours. The data is expressed as the percentage of the median fluorescence obtained at 0 hour (FIG. 15). VB5-845-Algo showed a slight increase over the 0 hour control suggesting that the Fab moiety is thermally stable.

Binding Affinity

The binding affinity was measured by flow cytometry using CAL-27 tumor cells. Using a titration curve, the $K_D$ was determined as described in the experimental designs (Table 10).

TABLE 10

| clone | $K_D$ (nM) |
|---|---|
| VB5-845-WT | 1.56 |
| VB5-845-Algo | 1.31 |

Biological Activity of VB6-845-Algo

To assess biological activity, VB6-845-Algo (containing deBouganin) was purified and tested by flow cytometry and MTS assay using CAL-27, HT-29, MCF-7 and OVCAR-3 EpCAM-positive cell lines. A-375 and COLO-320 EpCAM-negative cell lines were also included to ensure that the VB6-845-Algo specificity was not altered. As shown in Table 11, VB6-845-Algo binding to EpCAM-positive cell lines was 53% to 32% lower than the VB6-845-WT (used as a positive control). As a consequence, VB6-845-Algo was 7 to 9 times less potent compared to WT. As expected, no binding or $IC_{50}$ were measured with the EpCAM-negative cell lines.

TABLE 11

| | VB6-845-Algo | | VB6-845-WT | |
|---|---|---|---|---|
| | FI (100 ng/mL) | $IC_{50}$ (nM) | FI (100 ng/mL) | $IC_{50}$ (nM) |
| CAL-27 | 14 | 18 | 29.3 | 2.1 |
| HT-29 | 41.6 | 15 | 58.1 | 1.7 |
| MCF-7 | 27.7 | 2.3 | 46 | 0.3 |
| OVCAR-3 | 40.9 | 2.9 | 59.3 | 0.4 |
| A-375 | 1 | >50 | 1.05 | >50 |
| COLO-320 | 1.3 | >50 | 1.6 | >50 |

Representative numbers of two independent experiments. The Fold increased (FI) is an average of two independent measurements.

Immunogenicity

Figure 16:
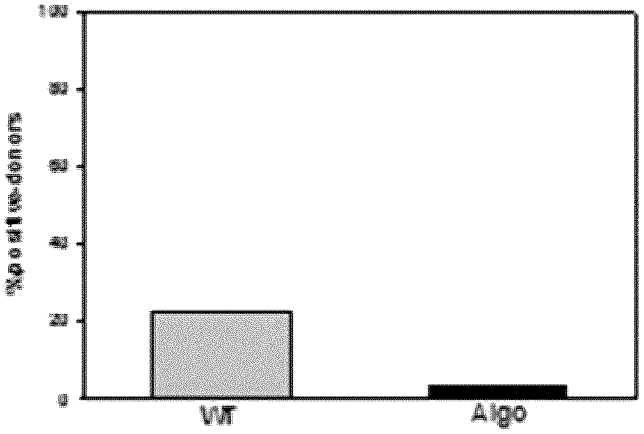
FIG. 16 shows the immunogenicity profile of the VB5-845-Algo as measured by the proliferation of CD3+CD4+ T cell assays.

The immunogenicity profile of the VB5-845-Algo was measured by the proliferation of CD3+CD4+ T cell and compare to VB5-845-WT. As expected, 12 donors out of 53 were responsive to VB5-845-WT which represents almost 23% (FIG. 16). In contrast, only 2 donors gave a response to the VB5-845-Algo (almost 4%) demonstrating that the introduced mutations have significantly reduced the immunogenic potential of the Fab moiety.

Sequence Listing (de-immunized $V_H$-$C_H$ or DI $V_H$-$C_H$)

SEQ ID NO: 1

EVQLVESGGGLVQPGGSLRLSCAASGYTFTAYGMNWVRQAPGKGLEWMG

WINTYTGESTYADSVKGRFTISADTSKNTAYLQMNSLRAEDTAVYYCARFAI

KGDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPS

NTKVDKKVEPKSC (de-immunized $V_L$-$C_L$ or DI $V_L$-$C_L$)

SEQ ID NO: 2

DIQMTQSPSSLSASVGDRVTITCRSTKSLLHSNGITYLYWYQQKPGKAPKLLI

YQMSNLASGVPSRFSSSGSGTDFTLTISSLQPEDFATYYCAQNLEIPRTFGTGT

KVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVT

KSFNRGEC (ETA toxin 252-608)

SEQ ID NO: 3

EGGSLAALTAHQACHLPLETFTRHRQPRGWEQLEQCGYPVQRLVALYLAAR

LSWNQVDQVIRNALASPGSGGDLGEAIREQPEQARLALTLAAAESERFVRQG

TGNDEAGAASADVVSLTCPVAAGECAGPADSGDALLERNYPTGAEFLGDGG

DVSFSTRGTQNWTERLLQAHRQLEERGYVFVGYHGTFLEAAQSIVEGGVRAR

SQDLDAIWRGFYIAGDPALAYGYAQDQEPDARGRIRNGALLRVYVPRSSLPG

FYRTGLTLAAPEAAGEVERUGHPLPLRLDAITGPEEEGGRLETILGWPLAERT

VVIPSAIPTDPRNVGGDLDPSSIPDKEQAISALPDYASQPGKPP (modified bouganin protein)

SEQ ID NO: 4

YNTVSFNLGEAYEYPTFIQDLRNELAKGTPVCQLPVTLQTIADDKREVLVDIT

TTSKKTVKVAIDVTDVYVVGYQDKWDGKDRAVFLDKVPTVATSKLFPGVTN

-continued

RVTLTFDGSYQKLVNAAKADRKALELGVNKLEFSIEAIHGKTINGQEAAKFFL

IVIQMVSEAARFKYIETEVVDRGLYGSFKPNFKVLNLENNWGDISDAIHKSSP

QCTTINPALQLISPSNDPWVVNKVSQISPDMGILKFKSSK (wild-type $V_H$-$C_H$ or WT $V_H$-$C_H$)

SEQ ID NO: 5

EVQLVQSGPGLVQPGGSVRISCAASGYTFTNYGMNWVKQAPGKGLEWMGW

INTYTGESTYADSFKGRFTFSLDTSASAAYLQINSLRAEDTAVYYCARFAIKG

DYWGQGTLLTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSC (wild-type $V_L$-$C_L$ or WT $V_L$-$C_L$)

SEQ ID NO: 6

DIQMTQSPSSLSASVGDRVTITCRSTKSLLHSNGITYLYWYQQKPGKAPKLLI

YQMSNLASGVPSRFSSSGSGTDFTLTISSLQPEDFATYYCAQNLEIPRTFGQGT

KVELKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVT

KSFNRGEC (DNA sequence of de-immunized VB5-845)

SEQ ID NO: 7

CTGCAGGTCTATGGAACGATAAATGCCCATGAAAATTCTATTTCAAGGAG

ACAGTCATAatgaaatacctattgcctacggcagccgctggattgttattactcg ctgcccaaccagcgatggcgGAAGTACAGCTGGTCgaaTCCGGTggtGGTCTGGT TCAGCCGGGTGGTAGCctgCGTctgAGCTGCGCGGCGAGCGGTTACACCTTCACC gcgTACGGTATGAACTGGGTTcgtCAGGCTCCGGGTAAAGGTTTGGAATGGATGG GTTGGATCAACACCTATACCGGTGAGTCTACCTACGCTGATAGCgttAAAGGCCG TTTCACCatcAGCgctGACACTAGCaaaaacaccGCGTACCTGCAGatgAACTCT

CTGCGTGCTGAGGACACTGCGGTTTACTACTGCGCTCGTTTCGCGATCAAAGGTG

ACTATTGGGGTCAGGGTACTCTGgttACCGTTAGCAGCGCTAGCACTAAgGGcCC

GTCCGTTTTCCCACTGGCTCCGTCTTCTAAAAGCACTTCTGGTGGTACCGCGGCTC

TGGGTTGCCTTGTTAAAGACTACTTCCCTGAACCGGTCACCGTTAGCTGGA

ACTCCGGTGCGTTGACCTCTGGTGTTCACACCTTCCCAGCGGTTCTGCAGT

CTAGCGGTCTGTATAGCCTGAGCTCTGTAGTTACCGTTCCGTCTTCTAGCC

TGGGTACGCAGACCTACATCTGCAACGTGAACCACAAACCGAGCAACACT

AAAGTGGATAAAAAAGTTGAACCGAAGTCTTGCTAGTAATCTAGAGTCGA

CCTGCAGGTCTATGGAACGATAAATGCCCATGAAAATTCTATTTCAAGGA

GACAGTCATAATGAAATACCTTCTGCCGACCGCTGCCGCTGGTCTGCTGCT

GTTGGCTGCTCAACCGGCTATGGCAGACATCCAGATGACCCAGTCCCCGT

CTAGCCTGAGCGCAAGCGTTGGTGACCGTGTGACCATCACCTGCCGTAGC

ACTAAATCCCTGCTGCACTCTAACGGCATCACCTACCTGTATTGGTACCAA

CAGAAACCGGGTAAAGCTCCGAAACTGCTGATCTACCAGATGTCTAACCT

GGCTAGCGGCGTTCCTTCTCGTTTTTCTTCTAGCGGTAGCGGTACTGACTT

CACCCTGACCATTAGCTCTCTGCAGCCTGAAGACTTTGCGACCTACTATTG

CGCTCAGAACCTTGAAATCCCGCGTACCTTCGGCaccGGTACCAAAGTTGA

AatcAAGCGTACCGTTGCGGCTCCGTCTGTTTTCATCTTCCCACCTAGCGAT

-continued

GAACAGCTTAAATCTGGTACTGCTAGCGTAGTTTGCCTGCTTAACAACTTC

TACCCTCGTGAAGCTAAAGTTCAGTGGAAAGTTGACAACGCTCTGCAGTC

TGGTAACTCTCAGGAATCTGTGACCGAACAGGATAGCAAAGATAGCACCT

ATAGCCTGTCTAGCACCCTGACCCTTAGCAAGGCGGACTATGAAAAACAC

AAAGTTTACGCTTGCGAGGTGACCCACCAAGGTCTGTCTTCTCCGGTGACT

AAATCCTTTAACCGTGGCGAATGCTAGTGA (4D5MOC-B)

SEQ ID NO: 8

DIQMTQSPSSLSASVGDRVTITCRSTKSLLHSNGITYLYWYQQKPGKAPK

LLIYQMSNLASGVPSRFSSSGSGTDFTLTISSLQPEDFATYYCAQNLEIP

RTFGQGTKVELKRTPSHNSHQVPSAGGPTANSGTSGSEVQLVQSGPGLVQ

PGGSVRISCAASGYTFTNYGMNWVKQAPGKGLEWMGWINTYTGESTYADSF

KGRFTFSLDTSASAAYLQINSLRAEDTAVYYCARFAIKGDYWGQGTLLTVSS (modified bouganin protein)

SEQ ID NO: 9

YNTVSFNLGEAYEYPTFIQDLRNELAKGTPVCQLPVTLQTIADDKRFVLVDIT

TTSKKTVKVAIDVTDVYVVGYQDKWDGKDRAVFLDKVPTVATSKLFPGVTN

RVTLTFDGSYQKLVNAAKX$^1$DRKX$^2$LX$^3$LGVX$^4$KLEFSIEAIHGKTINGQEX$^5$AK

FFLIVIQMVSEAARFKYIETEVVDRGLYGSFKPNFKVLNLENNWGDISDAIHK

SSPQCTTINPALQLISPSNDPWVVNKVSQISPDMGILKFKSSK wherein X$^1$ at position 123 is Thr or Ala or Gln; X$^2$ at position 127 is Gly or Ala; X$^3$ at position 129 is Gln or Gly or Glu; X$^4$ at position 133 is Asn or Asp or Thr or Ala or Arg or Gln or Glu or Gly or His or Lys or Ser; and X$^5$ at position 152 is Gln or Ala.

(VB6-845)

SEQ ID NO: 10

MKYLLPTAAAGLLLLAAQPAMAEVQLVQSGPGLVQPGGSVRISCAASGYTFT

NYGMNWVKQAPGKGLEWMGWINTYTGESTYADSFKGRFTFSLDTSASAAY

LQINSLRAEDTAVYYCARFAIKGDYWGQGTLLTVSSASTKGPSVFPLAPSSKS

TSGGTAALGCLVKDYFPEPVTVSWNSGALTSGVHTFPAVLQSSGLYSLSSVV

TVPSSSLGTQTYICNVNHKPSNTKVDKKVEPKSCTRHRQPRGWEQLYNTVSF

NLGEAYEYPTFIQDLRNELAKGTPVCQLPVTLQTIADDKRFVLVDITTTSKKT

VKVAIDVTDVYVVGYQDKWDGKDRAVFLDKVPTVATSKLFPGVTNRVTLTF

DGSYQKLVNAAKADRKALELGVNKLEFSIEAIHGKTINGQEAAKFFLIVIQMV

SEAARFKYIETEVVDRGLYGSFKPNFKVLNLENNWGDISDAIHKSSPQCTTINP

ALQLISPSNDPWVVNKVSQISPDMGILKFKSSKMKYLLPTAAAGLLLLAAQPA

MAHHEIFIEIHDIQMTQSPSSLSASVGDRVTITCRSTKSLLHSNGITYLYWYQQK

PGKAPKLLIYQMSNLASGVPSRFSSSGSGTDFTLTISSLQPEDFATYYCAQNLE

IPRTFGQGTKVELKRTVAAPSVFIFPPSDEQLKSGTASVVCLLNNFYPREAKV

QWKVDNALQSGNSQESVTEQDSKDSTYSLSSTLTLSKADYEKHKVYACEVT

HQGLSSPVTKSFNRGEC (Algo $V_H$-$C_H$)

SEQ ID NO: 11

EVQLQQSGPGLVQPGGSVRISCAASGYTFTAYGMNWVRQAPGKGLEWMGW

INTYTGESTYADSFKGRFEFSLDTHNSSAYLQIQSLREEDTAVYYCARFAIQG

DYWGQGTLVTVSSASTKGPSVFPLAPSSKSTSGGTAALGCLVKDYFPEPVTVS

-continued

WNSGALTSGVHTFPAVLQSSGLYSLSSVVTVPSSSLGTQTYICNVNHKPSNTK

VDKKVEPKSC (Algo $V_L$-$C_L$)

SEQ ID NO: 12

DIQMTQSPSSLSASVGDRVTITCKSTKSLLHSNGITYLYWYQQKPGSAPKLLIY

QMSHLASGVPSRFSSSGSGTDFTLTISSLQPEDFATYYCAQNLEIPRTFGQGTK

VEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSF

NRGEC (DI $V_H$-$C_H$-deBouganin)

SEQ ID NO: 13

EVQLVESGGGLVQPGGSLRLSCAASGYTFTAYGMNAVVRQAPGKGLEWMG

WINTYTGESTYADSVKGRFTISADTSKNTAYLQMNSLRAEDTAVYYCARFAI

KGDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPS

NTKVDKKVEPKSCTRHRQPRGWEQKYNTVSFNLGEAYEYPTFIQDLRNELAK

GTPVCQLPVTLQTIADDKRFVLVDITTTSKKTVKVAIDVTDVYVVGYQDKWD

GKDRAVFLDKVPTVATSKLFPGVTNRVTLTFDGSYQKLVNAAKADRKALEL

GVNKLEFSIEAIHGKTINGQEAAKFFLIVIQMVSEAARFKYIETEVVDRGLYGS

FKPNFKVLNLENNWGDISDAIHKSSPQCTTINPALQLISPSNDPWVVNKVSQIS

PDMGILKFKSSK (Algo $V_H$-$C_H$-deBouganin)

SEQ ID NO: 14

EVQLQQSGPGLVQPGGSVRISCAASGYTFTAYGMNWVRQAPGKGLEWMGW

INTYTGESTYADSFKGRFEFSLDTHNSSAYLQIQSLREEDTAVYYCARFAIQG

DYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSCTRHRQPRGWEQKYNTVSFNLGEAYEYPTFIQDLRNELAKGTP

VCQLPVTLQTIADDKRFVLVDITTTSKKTVKVAIDVTDVYVVGYQDKWDGK

DRAVFLDKVPTVATSKLFPGVTNRVTLTFDGSYQKLVNAAKADRKALELGV

NKLEFSIEAIHGKTINGQEAAKFFLIVIQMVSEAARFKYIETEVVDRGLYGSFK

PNFKVLNLENNWGDISDAIHKSSPQCTTINPALQLISPSNDPWVVNKVSQISPD

MGILKFKSSK (WT $V_H$-$C_H$-deBouganin)

SEQ ID NO: 15

EVQLVQSGPGLVQPGGSVRISCAASGYTFTNYGMNWVKQAPGKGLEWMGW

INTYTGESTYADSFKGRFTFSLDTSASAAYLQINSLRAEDTAVYYCARFAIKG

DYWGQGTLLTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSCTRHRQPRGWEQKYNTVSFNLGEAYEYPTFIQDLRNELAKGTP

VCQLPVTLQTIADDKRFVLVDITTTSKKTVKVAIDVTDVYVVGYQDKWDGK

DRAVFLDKVPTVATSKLFPGVTNRVTLTFDGSYQKLVNAAKADRKALELGV

NKLEFSIEAIHGKTINGQEAAKFFLIVIQMVSEAARFKYIETEVVDRGLYGSFK

PNFKVLNLENNWGDISDAIHKSSPQCTTINPALQLISPSNDPWVVNKVSQISPD

MGILKFKSSK

-continued (DI $V_L$-$C_L$-deBouganin)

SEQ ID NO: 16

DIQMTQSPSSLSASVGDRVTITCRSTKSLLHSNGITYLYWYQQKPGKAPKLLI
YQMSNLASGVPSRFSSSGSGTDFTLTISSLQPEDFATYYCAQNLEIPRTFGTGT
KVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVT
KSFNRGECTRHRQPRGWEQKYNTVSFNLGEAYEYPTFIQDLRNELAKGTPVC
QLPVTLQTIADDKRFVLVDITTTSKKTVKVAIDVTDVYVVGYQDKWDGKDR
AVFLDKVPTVATSKLFPGVTNRVTLTFDGSYQKLVNAAKADRKALELGVNK
LEFSIEAIHGKTINGQEAAKFFLIVIQMVSEAARFKYIETEVVDRGLYGSFKPNF
KVLNLENNWGDISDAIHKSSPQCTTINPALQLISPSNDPWVVNKVSQISPDMGI
LKFKSSK (Algo $V_L$-$C_L$-deBouganin)

SEQ ID NO: 17

DIQMTQSPSSLSASVGDRVTITCKSTKSLLHSNGITYLYWYQQKPGSAPKLLIY
QMSHLASGVPSRFSSSGSGTDFTLTISSLQPEDFATYYCAQNLEIPRTFGQGTK
VEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSF
NRGECTRHRQPRGWEQKYNTVSFNLGEAYEYPTFIQDLRNELAKGTPVCQLP
VTLQTIADDKRFVLVDITTTSKKTVKVAIDVTDVYVVGYQDKWDGKDRAVF
LDKVPTVATSKLFPGVTNRVTLTFDGSYQKLVNAAKADRKALELGVNKLEFS
IEAIHGKTINGQEAAKFFLIVIQMVSEAARFKYIETEVVDRGLYGSFKPNFKVL
NLENNWGDISDAIHKSSPQCTTINPALQLISPSNDPWVVNKVSQISPDMGILKF
KSSK (WT $V_L$-$C_L$-deBouganin)

SEQ ID NO: 18

DIQMTQSPSSLSASVGDRVTITCRSTKSLLHSNGITYLYWYQQKPGKAPKLLI
YQMSNLASGVPSRFSSSGSGTDFTLTISSLQPEDFATYYCAQNLEIPRTFGQGT
KVELKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVT
KSFNRGECTRHRQPRGWEQKYNTVSFNLGEAYEYPTFIQDLRNELAKGTPVC
QLPVTLQTIADDKRFVLVDITTTSKKTVKVAIDVTDVYVVGYQDKWDGKDR
AVFLDKVPTVATSKLFPGVTNRVTLTFDGSYQKLVNAAKADRKALELGVNK
LEFSIEAIHGKTINGQEAAKFFLIVIQMVSEAARFKYIETEVVDRGLYGSFKPNF
KVLNLENNWGDISDAIHKSSPQCTTINPALQLISPSNDPWVVNKVSQISPDMGI
LKFKSSK (Nucleotide sequence of DI $V_H$-$C_H$)

SEQ ID NO: 19

CTG CAG GTC TAT GGA ACG ATA AAT GCC CAT GAA AAT TCT ATT TCA
AGG AGA CAG TCA TA ATG AAA TAC CTA TTG CCT ACG GCA GCC GCT
GGA TTG TTA TTA CTC GCT GCC CAA CCA GCG ATG GCG GAA GTA CAG
CTG GTC gaa TCC GGT ggt GGT CTG GTT CAG CCG GGT GGT AGC ctg CGT
ctg AGC TGC GCG GCG AGC GGT TAC ACC TTC ACC gcg TAC GGT ATG
AAC TGG GTT cgt CAG GCT CCG GGT AAA GGT TTG GAA TGG ATG GGT
TGG ATC AAC ACC TAT ACC GGT GAG TCT ACC TAC GCT GAT AGC gtt -continued AAA GGC CGT TTC ACC atc AGC get GAC ACT TCT aaa aac acc GCG TAC
CTG CAG atg AAC TCT CTG CGT GCT GAG GAC ACT GCG GTT TAC TAC
TGC GCT CGT TTC GCG ATC AAA GGT GAC TAT TGG GGT CAG GGT ACT
CTG gtt ACC GTT AGC AGC GCT AGC ACT AAG GGC CCG TCC GTT TTC
CCA CTG GCT CCG TCT TCT AAA AGC ACT TCT GGT GGT ACC GCG GCT
CTG GGT TGC CTT GTT AAA GAC TAC TTC CCT GAA CCG GTC ACC GTT
AGC TGG AAC TCC GGT GCG TTG ACC TCT GGT GTT CAC ACC TTC CCA
GCG GTT CTG CAG TCT AGC GGT CTG TAT AGC CTG AGC TCT GTA GTT
ACC GTT CCG TCT TCT AGC CTG GGT ACG CAG ACC TAC ATC TGC AAC
GTG AAC CAC AAA CCG AGC AAC ACT AAA GTG GAT AAA AAA GTT
GAA CCG AAG TCT TGC TAG TAA (Nucleotide sequence of DI $V_L$-$C_L$)

SEQ ID NO: 20

CTG CAG GTC TAT GGA ACG ATA AAT GCC CAT GAA AAT TCT ATT TCA
AGG AGA CAG TCA TA ATG AAA TAC CTT CTG CCG ACC GCT GCC GCT
GGT CTG CTG CTG TTG GCT GCT CAA CCG GCT ATG GCA GAC ATC CAG
ATG ACC CAG TCC CCG TCT AGC CTG AGC GCA AGC GTT GGT GAC CGT
GTG ACC ATC ACC TGC CGT AGC ACT AAA TCC CTG CTG CAC TCT AAC
GGC ATC ACC TAC CTG TAT TGG TAC CAA CAG AAA CCG GGT AAA GCT
CCG AAA CTG CTG ATC TAC CAG ATG TCT AAC CTG GCT AGC GGC GTT
CCT TCT CGT TTT TCT TCT AGC GGT AGC GGT ACT GAC TTC ACC CTG
ACC ATT AGC TCT CTG CAG CCT GAA GAC TTT GCG ACC TAC TAT TGC
GCT CAG AAC CTT GAA ATC CCG CGT ACC TTC GGC acc GGT ACC AAA
GTT GAA atc AAG CGT ACC GTT GCG GCT CCG TCT GTT TTC ATC TTC
CCA CCT AGC GAT GAA CAG CTT AAA TCT GGT ACT GCT AGC GTA GTT
TGC CTG CTT AAC AAC TTC TAC CCT CGT GAA GCT AAA GTT CAG TGG
AAA GTT GAC AAC GCT CTG CAG TCT GGT AAC TCT CAG GAA TCT GTG
ACC GAA CAG GAT AGC AAA GAT AGC ACC TAT AGC CTG TCT AGC ACC
CTG ACC CTT AGC AAG GCG GAC TAT GAA AAA CAC AAA GTT TAC GCT
TGC GAG GTG ACC CAC CAA GGT CTG TCT TCT CCG GTG ACT AAA TCC
TTT AAC CGT GGC GAA TGC TAG TGA (Nucleotide sequence of WT $V_H$-$C_H$)

SEQ ID NO: 21

CTG CAG GTC TAT GGA ACG ATA AAT GCC CAT GAA AAT TCT ATT TCA
AGG AGA CAG TCA TA ATG AAA TAC CTA TTG CCT ACG GCA GCC GCT
GGA TTG TTA TTA CTC GCT GCC CAA CCA GCG ATG GCG GAA GTA CAG
CTG GTT CAG TCC GGC CCG GGT CTT GTT CAA CCG GGT GGT TCC GTT
CGT ATC TCT TGC GCT GCT TCT GGT TAC ACG TTC ACC AAC TAC GGC
ATG AAC TGG GTC AAA CAG GCT CCG GGT AAA GGC CTG GAA TGG
ATG GGC TGG ATC AAC ACC TAC ACC GGT GAA TCC ACC TAC GCT GAC
TCC TTC AAA GGT CGC TTC ACT TTC TCC CTC GAC ACA AGT GCT AGT
GCT GCA TAC CTC CAA ATC AAC TCG CTG CGT GCA GAG GAT ACA GCA
GTC TAT TAC TGC GCC CGT TTC GCT ATC AAA GGT GAC TAC TGG GGT

-continued

CAA GGC ACG CTG CTG ACC GTT TCC TCG GCT AGC ACC AAA GGC CCA

TCG GTC TTC CCC CTG GCA CCC TCC TCC AAG AGC ACC TCT GGG GGC

ACA GCG GCC CTG GGC TGC CTG GTC AAG GAC TAC TTC CCC GAA CCG

GTG ACG GTG TCG TGG AAC TCA GGC GCC CTG ACC AGC GGC GTG CAC

ACC TTC CCG GCT GTC CTA CAG TCC TCA GGA CTC TAC TCC CTC AGC

AGC GTG GTG ACC GTG CCC TCC AGC AGC TTG GGC ACC CAG ACC TAC

ATC TGC AAC GTG AAT CAC AAG CCC AGC AAC ACC AAG GTG GAC

AAG AAA GTT GAG CCC AAA TCT TGT TAG TGA (Nucleotide sequence of WT $V_L$-$C_L$)

SEQ ID NO: 22

CTG CAG GTC TAT GGA ACG ATA AAT GCC CAT GAA AAT TCT ATT TCA

AGG AGA CAG TCA TA ATG AAA TAC CTA TTG CCT ACG GCA GCC GCT

GGA TTG TTA TTA CTC GCT GCC CAA CCA GCG ATG GCG CAC CAT CAT

CAC CAT CAC GAT ATC CAG ATG ACC CAG TCC CCG TCC TCC CTG AGT

GCT TCT GTT GGT GAC CGT GTT ACC ATC ACC TGC CGT TCC ACC AAA

TCC CTC CTG CAC TCC AAC GGT ATC ACC TAC CTT TAT TGG TAT CAA

CAG AAA CCG GGT AAA GCT CCG AAA CTT CTG ATC TAC CAG ATG TCC

AAC CTG GCT TCC GGT GTT CCG TCT CGT TTC TCC AGT TCT GGT TCT

GGT ACC GAC TTC ACC CTG ACC ATC TCT TCT CTG CAG CCG GAA GAC

TTC GCT ACC TAC TAC TGC GCT CAG AAC CTG GAA ATC CCG CGT ACC

TTC GGT CAG GGT ACC AAA GTT GAA CTT AAG CGC ACT GTG GCT GCA

CCA TCT GTC TTC ATC TTC CCG CCA TCT GAT GAG CAG TTG AAA TCT

GGA ACT GCC TCT GTT GTG TGC CTG CTG AAT AAC TTC TAT CCC AGA

GAG GCC AAA GTA CAG TGG AAG GTG GAT AAC GCC CTC CAA TCG

GGT AAC TCC CAG GAG AGT GTC ACA GAG CAG GAC AGC AAG GAC

AGC ACC TAC AGC CTC AGC AGC ACC CTG ACG CTG AGC AAA GCA

GAC TAC GAG AAA CAC AAA GTC TAC GCC TGC GAA GTC ACC CAT CAG

GGC CTG AGC TCG CCC GTC ACA AAG AGC TTC AAC AGG GGA GAG TGT

TAG TGA (Nucleotide sequence of Algo $V_H$-$C_H$)

SEQ ID NO: 23

GAATTCCTGCAGGTCTATGGAACGATAAATGCCCATGAAAATTCTATTTCA

AGGAGACAGTCATAATGAAATACCTATTGCCTACGGCAGCCGCTGGATTG

TTATTACTCGCTGCCCAACCAGCGATGGCGGAAGTACAGCTGcagCAGTCC

GGTCCGGGTCTGGTTCAGCCGGGTGGTAGCGTTCGTATTAGCTGCGCGGC

GAGCGGTTACACCTTCACCgcgTACGGTATGAACTGGGTTcgtCAGGCTCCG

GGTAAAGGTTTGGAATGGATGGGTTGGATCAACACCTATACCGGTGAGTC

TACCTACGCTGATAGCTTCAAAGGCCGTTTCgaaTTTAGCCTTGACACTcacaa cAGCtctGCGTACCTGCAGATTcagTCTCTGCGTgaaGAGGACACTGCGGTTTA CTACTGCGCTCGTTTCGCGATCcagGGTGACTATTGGGGTCAGGGTACTCTG gttACCGTTAGCAGCGCTAGCACTAAgGGcCCGTCCGTTTTCCCACTGGCTCC

GTCTTCTAAAAGCACTTCTGGTGGTACCGCGGCTCTGGGTTGCCTTGTTAA

AGACTACTTCCCTGAACCGGTCACCGTTAGCTGGAACTCCGGTGCGTTGAC

-continued

CTCTGGTGTTCACACCTTCCCAGCGGTTCTGCAGTCTAGCGGTCTGTATAG

CCTGAGCTCTGTAGTTACCGTTCCGTCTTCTAGCCTGGGTACGCAGACCTA

CATCTGCAACGTGAACCACAAACCGAGCAACACTAAAGTGGATAAAAAA

GTTGAACCGAAGTCTTGCTAGTAA (Nucleotide sequence of Algo $V_L$-$C_L$)

SEQ ID NO: 24

TCTAGAGTCGACCTGCAGGTCTATGGAACGATAAATGCCCATGAAAATTC

TATTTCAAGGAGACAGTCATAATGAAATACCTTCTGCCGACCGCTGCCGCT

GGTCTGCTGCTGTTGGCTGCTCAACCGGCTATGGCAGACATCCAGATGAC

CCAGTCCCCGTCTAGCCTGAGCGCAAGCGTTGGTGACCGTGTGACCATCA

CCTGCaaaAGCACTAAATCCCTGCTGCACTCTAACGGCATCACCTACCTGTA

TTGGTACCAACAGAAACCGGGTtctGCTCCGAAACTGCTGATCTACCAGATG

TCTcacCTGGCTAGCGGCGTTCCTTCTCGTTTTTCTTCTAGCGGTAGCGGTAC

TGACTTCACCCTGACCATTAGCTCTCTGCAGCCTGAAGACTTTGCGACCTA

CTATTGCGCTCAGAACCTTGAAATCCCGCGTACCTTCGGCCAGGGTACCA

AAGTTGAAatcAAGCGTACCGTTGCGGCTCCGTCTGTTTTCATCTTCCCACC

TAGCGATGAACAGCTTAAATCTGGTACTGCTAGCGTAGTTTGCCTGCTTAA

CAACTTCTACCCTCGTGAAGCTAAAGTTCAGTGGAAAGTTGACAACGCTC

TGCAGTCTGGTAACTCTCAGGAATCTGTGACCGAACAGGATAGCAAAGAT

AGCACCTATAGCCTGTCTAGCACCCTGACCCTTAGCAAGGCGGACTATGA

AAAACACAAAGTTTACGCTTGCGAGGTGACCCACCAAGGTCTGTCTTCTC

CGGTGACTAAATCCTTTAACCGTGGCGAATGC (Nucleotide sequence of DI $V_H$-$C_H$-deBouganin)

SEQ ID NO: 25

CTG CAG GTC TAT GGA ACG ATA AAT GCC CAT GAA AAT TCT ATT TCA

AGG AGA CAG TCA TA ATG AAA TAC CTA TTG CCT ACG GCA GCC GCT

GGA TTG TTA TTA CTC GCT GCC CAA CCA GCG ATG GCG GAA GTA CAG

CTG GTC gaa TCC GGT ggt GGT CTG GTT CAG CCG GGT GGT AGC ctg CGT ctg AGC TGC GCG GCG AGC GGT TAC ACC TTC ACC gcg TAC GGT ATG AAC TGG GTT cgt CAG GCT CCG GGT AAA GGT TTG GAA TGG ATG GGT TGG ATC AAC ACC TAT ACC GGT GAG TCT ACC TAC GCT GAT AGC gtt AAA GGC CGT TTC ACC atc AGC get GAC ACT TCT aaa aac acc GCG TAC CTG CAG atg AAC TCT CTG CGT GCT GAG GAC ACT GCG GTT TAC TAC

TGC GCT CGT TTC GCG ATC AAA GGT GAC TAT TGG GGT CAG GGT ACT

CTG gtt ACC GTT AGC AGC GCT AGC ACT AAG GGC CCG TCC GTT TTC

CCA CTG GCT CCG TCT TCT AAA AGC ACT TCT GGT GGT ACC GCG GCT

CTG GGT TGC CTT GTT AAA GAC TAC TTC CCT GAA CCG GTC ACC GTT

AGC TGG AAC TCC GGT GCG TTG ACC TCT GGT GTT CAC ACC TTC CCA

GCG GTT CTG CAG TCT AGC GGT CTG TAT AGC CTG AGC TCT GTA GTT

ACC GTT CCG TCT TCT AGC CTG GGT ACG CAG ACC TAC ATC TGC AAC

GTG AAC CAC AAA CCG AGC AAC ACT AAA GTG GAT AAA AAA GTT

GAA CCG AAG TCT TGC ACC CGT CAC CGT CAG CCG CGT GGT TGG GAA

CAG aaa TATAACACCGTATCTTTTAACCTGG GTG

-continued

AGGCGTATGAATACCCGACCTTCATCCAGGACCTGCGTAATGAACTTG

CTAAAGGTACCCCTGTTTGCCAGCTGCCTGTGACCCTGCAGACCATCGCTG

ATGATAAACGTTTCGTTCTGGTTGACATTACCACCACCTCCAAAAAAACCG

TTAAAGTCGCGATCGATGTGACCGACGTTTACGTGGTAGGTTACCAGGAT

AAATGGGACGGTAAAGATCGTGCGGTTTTCCTGGACAAAGTTCCGACCGT

AGCGACTTCTAAACTGTTCCCAGGTGTGACCAACCGTGTGACCCTGACCTT

CGACGGCAGCTATCAGAAACTGGTTAACGCGGCCAAAGCTGATCGTAAAG

CTCTCGAACTGGGTGTTAACAAACTGGAGTTCAGCATTGAAGCTATCCAC

GGTAAAACCATCAACGGTCAAGAAGCAGCTAAATTCTTCCTGATCGTGAT

CCAGATGGTTAGCGAAGCAGCGCGTTTTAAATACATTGAAACCGAAGTAG

TTGATCGTGGTCTGTATGGTAGCTTCAAACCGAACTTCAAAGTTCTTAACC

TGGAGAACAACTGGGGTGACATTAGCGACGCGATCCATAAATCTTCCCCG

CAATGCACCACCATTAACCCGGCTCTGCAGCTGATCTCTCCGTCTAACGAT

CCGTGGGTAGTTAACAAAGTGTCTCAAATCAGCCCGGACATGGGTATCCT

GAAATTTAAATCTAGCAAATAGTGACTCGAG (Nucleotide sequence of Algo $V_H$-$C_H$-deBouganin)

SEQ ID NO: 26

GAATTCCTGCAGGTCTATGGAACGATAAATGCCCATGAAAATTCTATTTCA

AGGAGACAGTCATAATGAAATACCTATTGCCTACGGCAGCCGCTGGATTG

TTATTACTCGCTGCCCAACCAGCGATGGCGGAAGTACAGCTGcagCAGTCC

GGTCCGGGTCTGGTTCAGCCGGGTGGTAGCGTTCGTATTAGCTGCGCGGC

GAGCGGTTACACCTTCACCgcgTACGGTATGAACTGGGTTcgtCAGGCTCCG

GGTAAAGGTTTGGAATGGATGGGTTGGATCAACACCTATACCGGTGAGTC

TACCTACGCTGATAGCTTCAAAGGCCGTTTCgaaTTTAGCCTTGACACTcacaa cAGCtctGCGTACCTGCAGATTcagTCTCTGCGTgaaGAGGACACTGCGGTTTA CTACTGCGCTCGTTTCGCGATCcagGGTGACTATTGGGGTCAGGGTACTCTG gttACCGTTAGCAGCGCTAGCACTAAgGGcCCGTCCGTTTTCCCACTGGCTCC

GTCTTCTAAAAGCACTTCTGGTGGTACCGCGGCTCTGGGTTGCCTTGTTAA

AGACTACTTCCCTGAACCGGTCACCGTTAGCTGGAACTCCGGTGCGTTGAC

CTCTGGTGTTCACACCTTCCCAGCGGTTCTGCAGTCTAGCGGTCTGTATAG

CCTGAGCTCTGTAGTTACCGTTCCGTCTTCTAGCCTGGGTACGCAGACCTA

CATCTGCAACGTGAACCACAAACCGAGCAACACTAAAGTGGATAAAAAA

GTTGAACCGAAGTCTTGCACCCGTCACCGTCAGCCGCGTGGTTGGGAACA

GaaaTATAACACCGTATCTTTTAACCTGGGTGAGGCGTATGAATACCCGACC

TTCATCCAGGACCTGCGTAATGAACTTGCTAAAGGTACCCCTGTTTGCCAG

CTGCCTGTGACCCTGCAGACCATCGCTGATGATAAACGTTTCGTTCTGGTT

GACATTACCACCACCTCCAAAAAAACCGTTAAAGTCGCGATCGATGTGAC

CGACGTTTACGTGGTAGGTTACCAGGATAAATGGGACGGTAAAGATCGTG

CGGTTTTCCTGGACAAAGTTCCGACCGTAGCGACTTCTAAACTGTTCCCAG

GTGTGACCAACCGTGTGACCCTGACCTTCGACGGCAGCTATCAGAAACTG

GTTAACGCGGCCAAAGCTGATCGTAAAGCTCTCGAACTGGGTGTTAACAA

ACTGGAGTTCAGCATTGAAGCTATCCACGGTAAAACCATCAACGGTCAAG

-continued

AAGCAGCTAAATTCTTCCTGATCGTGATCCAGATGGTTAGCGAAGCAGCG

CGTTTTAAATACATTGAAACCGAAGTAGTTGATCGTGGTCTGTATGGTAGC

TTCAAACCGAACTTCAAAGTTCTTAACCTGGAGAACAACTGGGGTGACAT

TAGCGACGCGATCCATAAATCTTCCCCGCAATGCACCACCATTAACCCGG

CTCTGCAGCTGATCTCTCCGTCTAACGATCCGTGGGTAGTTAACAAAGTGT

CTCAAATCAGCCCGGACATGGGTATCCTGAAATTTAAATCTAGCAAATAG

TGACTCGAG (Nucleotide sequence of WT $V_H$-$C_H$-deBouganin)

SEQ ID NO: 27

CTG CAG GTC TAT GGA ACG ATA AAT GCC CAT GAA AAT TCT ATT TCA

AGG AGA CAG TCA TA ATG AAA TAC CTA TTG CCT ACG GCA GCC GCT

GGA TTG TTA TTA CTC GCT GCC CAA CCA GCG ATG GCG GAA GTA CAG

CTG GTT CAG TCC GGC CCG GGT CTT GTT CAA CCG GGT GGT TCC GTT

CGT ATC TCT TGC GCT GCT TCT GGT TAC ACG TTC ACC AAC TAC GGC

ATG AAC TGG GTC AAA CAG GCT CCG GGT AAA GGC CTG GAA TGG

ATG GGC TGG ATC AAC ACC TAC ACC GGT GAA TCC ACC TAC GCT GAC

TCC TTC AAA GGT CGC TTC ACT TTC TCC CTC GAC ACA AGT GCT AGT

GCT GCA TAC CTC CAA ATC AAC TCG CTG CGT GCA GAG GAT ACA GCA

GTC TAT TAC TGC GCC CGT TTC GCT ATC AAA GGT GAC TAC TGG GGT

CAA GGC ACG CTG CTG ACC GTT TCC TCG GCT AGC ACC AAA GGC CCA

TCG GTC TTC CCC CTG GCA CCC TCC TCC AAG AGC ACC TCT GGG GGC

ACA GCG GCC CTG GGC TGC CTG GTC AAG GAC TAC TTC CCC GAA CCG

GTG ACG GTG TCG TGG AAC TCA GGC GCC CTG ACC AGC GGC GTG CAC

ACC TTC CCG GCT GTC CTA CAG TCC TCA GGA CTC TAC TCC CTC AGC

AGC GTG GTG ACC GTG CCC TCC AGC AGC TTG GGC ACC CAG ACC TAC

ATC TGC AAC GTG AAT CAC AAG CCC AGC AAC ACC AAG GTG GAC

AAG AAA GTT GAG CCC AAA TCT

TGTACCCGTCACCGTCAGCCGCGTGGTTGG GAA CAG CTC

TATAACACCGTATCTTTTAACCTGGGTGAGGCGTATGA ATACCCG

ACCTTCATCCAGGACCTGCGTAATGAACTTGCTAAAGGTACCCCTGTTTGC

CAGCTGCCTGTGACCCTGCAGACCATCGCTGATGATAAACGTTTCGTTCTG

GTTGACATTACCACCACCTCCAAAAAAACCGTTAAAGTCGCGATCGATGT

GACCGACGTTTACGTGGTAGGTTACCAGGATAAATGGGACGGTAAAGATC

GTGCGGTTTTCCTGGACAAAGTTCCGACCGTAGCGACTTCTAAACTGTTCC

CAGGTGTGACCAACCGTGTGACCCTGACCTTCGACGGCAGCTATCAGAAA

CTGGTTAACGCGGCCAAAGCTGATCGTAAAGCTCTCGAACTGGGTGTTAA

CAAACTGGAGTTCAGCATTGAAGCTATCCACGGTAAAACCATCAACGGTC

AAGAAGCAGCTAAATTCTTCCTGATCGTGATCCAGATGGTTAGCGAAGCA

GCGCGTTTTAAATACATTGAAACCGAAGTAGTTGATCGTGGTCTGTATGGT

AGCTTCAAACCGAACTTCAAAGTTCTTAACCTGGAGAACAACTGGGGTGA

CATTAGCGACGCGATCCATAAATCTTCCCCGCAATGCACCACCATTAACC

CGGCTCTGCAGCTGATCTCTCCGTCTAACGATCCGTGGGTAGTTAACAAAG

-continued

TGTCTCAAATCAGCCCGGACATGGGTATCCTGAAATTTAAATCTAGCAAA

TAGTGACTCGAG (Nucleotide sequence of DI $V_L$-$C_L$-deBouganin)

SEQ ID NO: 28

CTG CAG GTC TAT GGA ACG ATA AAT GCC CAT GAA AAT TCT ATT TCA

AGG AGA CAG TCA TA ATG AAA TAC CTT CTG CCG ACC GCT GCC GCT

GGT CTG CTG CTG TTG GCT GCT CAA CCG GCT ATG GCA GAC ATC CAG

ATG ACC CAG TCC CCG TCT AGC CTG AGC GCA AGC GTT GGT GAC CGT

GTG ACC ATC ACC TGC CGT AGC ACT AAA TCC CTG CTG CAC TCT AAC

GGC ATC ACC TAC CTG TAT TGG TAC CAA CAG AAA CCG GGT AAA GCT

CCG AAA CTG CTG ATC TAC CAG ATG TCT AAC CTG GCT AGC GGC GTT

CCT TCT CGT TTT TCT TCT AGC GGT AGC GGT ACT GAC TTC ACC CTG

ACC ATT AGC TCT CTG CAG CCT GAA GAC TTT GCG ACC TAC TAT TGC

GCT CAG AAC CTT GAA ATC CCG CGT ACC TTC GGC acc GGT ACC AAA

GTT GAA atc AAG CGT ACC GTT GCG GCT CCG TCT GTT TTC ATC TTC

CCA CCT AGC GAT GAA CAG CTT AAA TCT GGT ACT GCT AGC GTA GTT

TGC CTG CTT AAC AAC TTC TAC CCT CGT GAA GCT AAA GTT CAG TGG

AAA GTT GAC AAC GCT CTG CAG TCT GGT AAC TCT CAG GAA TCT GTG

ACC GAA CAG GAT AGC AAA GAT AGC ACC TAT AGC CTG TCT AGC ACC

CTG ACC CTT AGC AAG GCG GAC TAT GAA AAA CAC AAA GTT TAC GCT

TGC GAG GTG ACC CAC CAA GGT CTG TCT TCT CCG GTG ACT AAA TCC

TTT AAC CGT GGC GAA TGCACCCGTCACCGTCAGCCGCGTGGTTGGGA

ACAGaaa TATAA

CACCGTATCTTTTAACCTGGGTGAGGCGTATGAATACCCGACCTTCATC

CAGGACCTGCGTAATGAACTTGCTAAAGGTACCCCTGTTTGCCAGCTGCCT

GTGACCCTGCAGACCATCGCTGATGATAAACGTTTCGTTCTGGTTGACATT

ACCACCACCTCCAAAAAAACCGTTAAAGTCGCGATCGATGTGACCGACGT

TTACGTGGTAGGTTACCAGGATAAATGGGACGGTAAAGATCGTGCGGTTT

TCCTGGACAAAGTTCCGACCGTAGCGACTTCTAAACTGTTCCCAGGTGTGA

CCAACCGTGTGACCCTGACCTTCGACGGCAGCTATCAGAAACTGGTTAAC

GCGGCCAAAGCTGATCGTAAAGCTCTCGAACTGGGTGTTAACAAACTGGA

GTTCAGCATTGAAGCTATCCACGGTAAAACCATCAACGGTCAAGAAGCAG

CTAAATTCTTCCTGATCGTGATCCAGATGGTTAGCGAAGCAGCGCGTTTTA

AATACATTGAAACCGAAGTAGTTGATCGTGGTCTGTATGGTAGCTTCAAA

CCGAACTTCAAAGTTCTTAACCTGGAGAACAACTGGGGTGACATTAGCGA

CGCGATCCATAAATCTTCCCCGCAATGCACCACCATTAACCCGGCTCTGCA

GCTGATCTCTCCGTCTAACGATCCGTGGGTAGTTAACAAAGTGTCTCAAAT

CAGCCCGGACATGGGTATCCTGAAATTTAAATCTAGCAAATAGTGACTCG

AG (Nucleotide sequence of Algo $V_L$-$C_L$-deBouganin)

SEQ ID NO: 29

TCTAGAGTCGACCTGCAGGTCTATGGAACGATAAATGCCCATGAAAATTC

TATTTCAAGGAGACAGTCATAATGAAATACCTTCTGCCGACCGCTGCCGCT

-continued

GGTCTGCTGCTGTTGGCTGCTCAACCGGCTATGGCAGACATCCAGATGAC

CCAGTCCCCGTCTAGCCTGAGCGCAAGCGTTGGTGACCGTGTGACCATCA

CCTGCaaaAGCACTAAATCCCTGCTGCACTCTAACGGCATCACCTACCTGTA

TTGGTACCAACAGAAACCGGGTtctGCTCCGAAACTGCTGATCTACCAGATG

TCTcacCTGGCTAGCGGCGTTCCTTCTCGTTTTTCTTCTAGCGGTAGCGGTAC

TGACTTCACCCTGACCATTAGCTCTCTGCAGCCTGAAGACTTTGCGACCTA

CTATTGCGCTCAGAACCTTGAAATCCCGCGTACCTTCGGCCAGGGTACCA

AAGTTGAAatcAAGCGTACCGTTGCGGCTCCGTCTGTTTTCATCTTCCCACC

TAGCGATGAACAGCTTAAATCTGGTACTGCTAGCGTAGTTTGCCTGCTTAA

CAACTTCTACCCTCGTGAAGCTAAAGTTCAGTGGAAAGTTGACAACGCTC

TGCAGTCTGGTAACTCTCAGGAATCTGTGACCGAACAGGATAGCAAAGAT

AGCACCTATAGCCTGTCTAGCACCCTGACCCTTAGCAAGGCGGACTATGA

AAAACACAAAGTTTACGCTTGCGAGGTGACCCACCAAGGTCTGTCTTCTC

CGGTGACTAAATCCTTTAACCGTGGCGAATGCACCCGTCACCGTCAGCCG

CGTGGTTGGGAACAGaaaTATAACACCGTATCTTTTAACCTGGGTG

AGGCGTATGAATACCCGACCTTCATCCAGGACCTGCGTAAT

GAACTTGCTAAAGGTACCCCTGTTTGCCAGCTGCCTGTGACCCTGCAGACC

ATCGCTGATGATAAACGTTTCGTTCTGGTTGACATTACCACCACCTCCAAA

AAAACCGTTAAAGTCGCGATCGATGTGACCGACGTTTACGTGGTAGGTTA

CCAGGATAAATGGGACGGTAAAGATCGTGCGGTTTTCCTGGACAAAGTTC

CGACCGTAGCGACTTCTAAACTGTTCCCAGGTGTGACCAACCGTGTGACC

CTGACCTTCGACGGCAGCTATCAGAAACTGGTTAACGCGGCCAAAGCTGA

TCGTAAAGCTCTCGAACTGGGTGTTAACAAACTGGAGTTCAGCATTGAAG

CTATCCACGGTAAAACCATCAACGGTCAAGAAGCAGCTAAATTCTTCCTG

ATCGTGATCCAGATGGTTAGCGAAGCAGCGCGTTTTAAATACATTGAAAC

CGAAGTAGTTGATCGTGGTCTGTATGGTAGCTTCAAACCGAACTTCAAAG

TTCTTAACCTGGAGAACAACTGGGGTGACATTAGCGACGCGATCCATAAA

TCTTCCCCGCAATGCACCACCATTAACCCGGCTCTGCAGCTGATCTCTCCG

TCTAACGATCCGTGGGTAGTTAACAAAGTGTCTCAAATCAGCCCGGACAT

GGGTATCCTGAAATTTAAATCTAGCAAATAGTGACTCGAG (Nucleotide sequence of WT $V_L$-$C_L$-deBouganin)

SEQ ID NO: 30

CTG CAG GTC TAT GGA ACG ATA AAT GCC CAT GAA AAT TCT ATT TCA

AGG AGA CAG TCA TA ATG AAA TAC CTA TTG CCT ACG GCA GCC GCT

GGA TTG TTA TTA CTC GCT GCC CAA CCA GCG ATG GCG CAC CAT CAT

CAC CAT CAC GAT ATC CAG ATG ACC CAG TCC CCG TCC TCC CTG AGT

GCT TCT GTT GGT GAC CGT GTT ACC ATC ACC TGC CGT TCC ACC AAA

TCC CTC CTG CAC TCC AAC GGT ATC ACC TAC CTT TAT TGG TAT CAA

CAG AAA CCG GGT AAA GCT CCG AAA CTT CTG ATC TAC CAG ATG TCC

AAC CTG GCT TCC GGT GTT CCG TCT CGT TTC TCC AGT TCT GGT TCT

GGT ACC GAC TTC ACC CTG ACC ATC TCT TCT CTG CAG CCG GAA GAC

-continued

TTC GCT ACC TAC TAC TGC GCT CAG AAC CTG GAA ATC CCG CGT ACC

TTC GGT CAG GGT ACC AAA GTT GAA CTT AAG CGC ACT GTG GCT GCA

CCA TCT GTC TTC ATC TTC CCG CCA TCT GAT GAG CAG TTG AAA TCT

GGA ACT GCC TCT GTT GTG TGC CTG CTG AAT AAC TTC TAT CCC AGA

GAG GCC AAA GTA CAG TGG AAG GTG GAT AAC GCC CTC CAA TCG

GGT AAC TCC CAG GAG AGT GTC ACA GAG CAG GAC AGC AAG GAC

AGC ACC TAC AGC CTC AGC AGC ACC CTG ACG CTG AGC AAA GCA

GAC TAC GAG AAA CAC AAA GTC TAC GCC TGC GAA GTC ACC CAT CAG

GGC CTG AGC TCG CCC GTC ACA AAG AGC TTC AAC AGG GGA GAG TGT

ACCCGTCACCGTCAGCCG

CGTGGTTGGGAACAGCTCTATAACACCGTATCTTTTAACCT

GGGTGAGGCGT ATG

AATACCCGACCTTCATCCAGGACCTGCGTAATGAACTTG CTAAAGGT

ACCCCTGTTTGCCAGCTGCCTGTGACCCTGCAGACCATCGCTG

ATGATAAA

CGTTTCGTTCTGGTTGACATTACCACCACCTCCAAAAAAACCGTTAAAGTC

GCGATCGATGTGACCGACGTTTACGTGGTAGGTTACCAGGATAAATGGGA

CGGTAAAGATCGTGCGGTTTTCCTGGACAAAGTTCCGACCGTAGCGACTT

CTAAACTGTTCCCAGGTGTGACCAACCGTGTGACCCTGACCTTCGACGGC

AGC TATCAGAAACTGGTTAACGCGGCCAAAGCTGATCGTAAAGCTCTCGA

ACTGGGTGTTAACAAACTGGAGTTCAGCATTGAAGCTATCCACGGTAAAA

CCATCAACGGTCAAGAAGCAGCTAAATTCTTCCTGATCGTGATCCAGATG

GTTAGCGAAGCAGCGCGTTTTAAATACATTGAAACCGAAGTAGTTGATCG

TGGTCTGTATGGTAGCTTCAAACCGAACTTCAAAGTTCTTAACCTGGAGAA

CAACTGGGGTGACATTAGCGACGCGATCCATAAATCTTCCCCGCAATGCA

CCACCATTAACCCGGCTCTGCAGCTGATCTCTCCGTCTAACGATCCGTGGG

TAGTTAACAAAGTGTCTCAAATCAGCCCGGACATGGGTATCCTGAAATTT

AAATCTAGCAAATAGTGACTCGAG (Algo $V_H$(CDRsWT)-CH)

SEQ ID NO: 31

EVQLQQSGPGLVQPGGSVRISCAASGYTFTNYGMNWVRQAPGKGLEWMGW

INTYTGESTYADSFKGRFEFSLDTHNSSAYLQIQSLREEDTAVYYCARFAIKG

DYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSC (Algo $V_H$(CDRsWT + Treg)-CH)

SEQ ID NO: 32

EVQLQQSGPGLVQPGGSVRISCAASGYTFTNYGMNWVRQAPGKGLEWMGW

INTYTGESTYADSFKGRFEFSLDTHNSSAYLQMNSLRAEDTAVYYCARFAIKG

DYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSC

-continued (deBouganin 2)

SEQ ID NO: 33

YNTVSFNLGEAYEYPTFIQDLRNELAKGTPVCQLPVTLQTIADDKRFVLVDIT

TTSKKTVKVAIDVTDVYVVGYQDKWDGKDRAVFLDKVPTVATSKLFPGVTN

RVTLTFDGSYQKLVHSAEVDRKDLELGVNKLEFSIEAIHGKTINGQEIAKFFLI

VIQMVSEAARFKYIETEVVDRGLHGSFKPDFKVLDLENNWGDISDAIHKSSPQ

CTTINPALQLISPSNDPWVVNKVSQISPDMGILKFKSSK (DI $V_H$-$C_H$-deBouganin 3)

SEQ ID NO: 34

EVQLVESGGGLVQPGGSLRLSCAASGYTFTAYGMNWVRQAPGKGLEWMG

WINTYTGESTYADSVKGRFTISADTSKNTAYLQMNSLRAEDTAVYYCARFAI

KGDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPS

NTKVDKKVEPKSCTRHRQPRGWEQKYNTVSFNLGEAYEYPTFIQDLRNELAK

GTPVCQLPVTLQTIADDKRFVLVDITTTSKKTVKVAIDVTDVYVVGYQDKWD

GKDRAVFLDKVPTVATSKLFPGVTNRVTLTFDGSYQKLV*H*AAK*A*DRK*A*LEL

GV*N*KLEFSIEAIHGKTINGQE*A*AKFFLIVIQMVSEAARFKYIETEVVDRGLYGS

FKPNFKVLNLENNWGDISDAIHKSSPQCTTINPALQLISPSNDPWVVNKVSQIS

PDMGILKFKSSK (DI $V_L$-$C_L$-deBouganin 3)

SEQ ID NO: 35

DIQMTQSPSSLSASVGDRVTITCRSTKSLLHSNGITYLYWYQQKPGKAPKLLI

YQMSNLASGVPSRFSSSGSGTDFTLTISSLQPEDFATYYCAQNLEIPRTFGTGT

KVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVT

KSFNRGEC

TRHRQPRGWEQKYNTVSFNLGEAYEYPTFIQDLRNELAKGTPVCQLPVTLQTI

ADDKRFVLVDITTTSKKTVKVAIDVTDVYVVGYQDKWDGKDRAVFLDKVPT

VATSKLFPGVTNRVTLTFDGSYQKLV*H*AAK*A*DRK*A*LELGV*N*KLEFSIEAIHG

KTINGQE*A*AKFFLIVIQMVSEAARFKYIETEVVDRGLYGSFKPNFKVLNLENN

WGDISDAIHKSSPQCTTINPALQLISPSNDPWVVNKVSQISPDMGILKFKSSK (Algo $V_H$-$C_H$-deBouganin 3)

SEQ ID NO: 36

EVQLQQSGPGLVQPGGSVRISCAASGYTFTAYGMNWVRQAPGKGLEWMGW

INTYTGESTYADSFKGRFEFSLDTHNSSAYLQIQSLREEDTAVYYCARFAIQG

DYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSCTRHRQPRGWEQKYNTVSFNLGEAYEYPTFIQDLRNELAKGTP

VCQLPVTLQTIADDKRFVLVDITTTSKKTVKVAIDVTDVYVVGYQDKWDGK

DRAVFLDKVPTVATSKLFPGVTNRVTLTFDGSYQKLV*H*AAK*A*DRK*A*LELGV

*N*KLEFSIEAIHGKTINGQE*A*AKFFLIVIQMVSEARFKYIETEVVDRGLYGSFK

PNFKVLNLENNWGDISDAIHKSSPQCTTINPALQLISPSNDPWVVNKVSQISPD

MGILKFKSSK

-continued (Algo $V_L$-$C_L$-deBouganin 3)

SEQ ID NO: 37

DIQMTQSPSSLSASVGDRVTITCKSTKSLLHSNGITYLYWYQQKPGSAPKLLIY

QMSHLASGVPSRFSSSGSGTDFTLTISSLQPEDFATYYCAQNLEIPRTFGQGTK

VEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSF

NRGECTRHRQPRGWEQKYNTVSFNLGEAYEYPTFIQDLRNELAKGTPVCQLP

VTLQTIADDKRFVLVDITTTSKKTVKVAIDVTDVYVVGYQDKWDGKDRAVF

LDKVPTVATSKLFPGVTNRVTLTFDGSYQKLV*H*AAK*A*DRK*A*LELGV*N*KLEFS

IEAIHGKTINGQE*A*AKFFLIVIQMVSEAARFKYIETEVVDRGLYGSFKPNFKVL

NLENNWGDISDAIHKSSPQCTTINPALQLISPSNDPWVVNKVSQISPDMGILKF

KSSK (Algo $V_H$(CDRsWT)-$C_H$-deBouganin)

SEQ ID NO: 38

EVQLQQSGPGLVQPGGSVRISCAASGYTFTNYGMNWVRQAPGKGLEWMGW

INTYTGESTYADSFKGRFEFSLDTHNSSAYLQIQSLREEDTAVYYCARFAIKG

DYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSCTRHRQPRGWEQKYNTVSFNLGEAYEYPTFIQDLRNELAKGTP

VCQLPVTLQTIADDKRFVLVDITTTSKKTVKVAIDVTDVYVVGYQDKWDGK

DRAVFLDKVPTVATSKLFPGVTNRVTLTFDGSYQKLVNAAKADRKALELGV

NKLEFSIEAIHGKTINGQEAAKFFLIVIQMVSEAARFKYIETEVVDRGLYGSFK

PNFKVLNLENNWGDISDAIHKSSPQCTTINPALQLISPSNDPWVVNKVSQISPD

MGILKFKSSK (Algo $V_H$(CDRsWT)-$C_H$-deBouganin3)

SEQ ID NO: 39

EVQLQQSGPGLVQPGGSVRISCAASGYTFTNYGMNWVRQAPGKGLEWMGW

INTYTGESTYADSFKGRFEFSLDTHNSSAYLQIQSLREEDTAVYYCARFAIKG

DYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSCTRHRQPRGWEQKYNTVSFNLGEAYEYPTFIQDLRNELAKGTP

VCQLPVTLQTIADDKRFVLVDITTTSKKTVKVAIDVTDVYVVGYQDKWDGK

DRAVFLDKVPTVATSKLFPGVTNRVTLTFDGSYQKLV*H*AAK*A*DRK*A*LELGV

*N*KLEFSIEAIHGKTINGQE*A*AKFFLIVIQMVSEAARFKYIETEVVDRGLYGSFK

PNFKVLNLENNWGDISDAIHKSSPQCTTINPALQLISPSNDPWVVNKVSQISPD

MGILKFKSSK (Algo $V_H$(CDRsWT + Treg)-$C_H$-deBouganin)

SEQ ID NO: 40

EVQLQQSGPGLVQPGGSVRISCAASGYTFTNYGMNWVRQAPGKGLEWMGW

INTYTGESTYADSFKGRFEFSLDTHNSSAYLQMNSLRAEDTAVYYCARFAIKG

DYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSCTRHRQPRGWEQKYNTVSFNLGEAYEYPTFIQDLRNELAKGTP

VCQLPVTLQTIADDKRFVLVDITTTSKKTVKVAIDVTDVYVVGYQDKWDGK

DRAVFLDKVPTVATSKLFPGVTNRVTLTFDGSYQKLVNAAKADRKALELGV

-continued

NKLEFSIEAIHGKTINGQEAAKFFLIVIQMVSEAARFKYIETEVVDRGLYGSFK

PNFKVLNLENNWGDISDAIHKSSPQCTTINPALQLISPSNDPWVVNKVSQISPD

MGILKFKSSK (Algo $V_H$(CDRsWT + Treg)-$C_H$-deBouganin3)

SEQ ID NO: 41

EVQLQQSGPGLVQPGGSVRISCAASGYTFTNYGMNWVRQAPGKGLEWMGW

INTYTGESTYADSFKGRFEFSLDTHNSSAYLQMNSLRAEDTAVYYCARFAIKG

DYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSCTRHRQPRGWEQKYNTVSFNLGEAYEYPTFIQDLRNELAKGTP

VCQLPVTLQTIADDKRFVLVDITTTSKKTVKVAIDVTDVYVVGYQDKWDGK

DRAVFLDKVPTVATSKLFPGVTNRVTLTFDGSYQKLV*H*AAK*A*DRK*A*LELGV

*N*KLEFSIEAIHGKTINGQE*A*AKFFLIVIQMVSEAARFKYIETEVVDRGLYGSFK

PNFKVLNLENNWGDISDAIHKSSPQCTTINPALQLISPSNDPWVVNKVSQISPD

MGILKFKSSK (deBouganin 3)

SEQ ID NO: 42

YNTVSFNLGEAYEYPTFIQDLRNELAKGTPVCQLPVTLQTIADDKRFVLVDIT

TTSKKTVKVAIDVTDVYVVGYQDKWDGKDRAVFLDKVPTVATSKLFPGVTN

RVTLTFDGSYQKLV*H*AAK*A*DRK*A*LELGV*N*KLEFSIEAIHGKTINGQE*A*AKFFL

IVIQMVSEAARFKYIETEVVDRGLYGSFKPNFKVLNLENNWGDISDAIHKSSP

QCTTINPALQLISPSNDPWVVNKVSQISPDMGILKFKSSK (deBouganin 4)

SEQ ID NO: 43

YNTVSFNLGEAYEYPTFIQDLRNELAKGTPVCQLPVTLQTIADDKRFVLVDIT

TTSKKTVKVAIDVTDVYVVGYQDKWDGKDRAVFLDKVPTVATSKLFPGVTN

RVTLTFDGSYQKLV*H*AAKVDRKDLELGV*N*KLEFSIEAIHGKTINGQEIAKFFLI

VIQMVSEAARFKYIETEVVDRGLYGSFKPNFKVLNLENNWGDISDAIHKSSPQ

CTTINPALQLISPSNDPWVVNKVSQISPDMGILKFKSSK (DI $V_H$-$C_H$-deBouganin 4)

SEQ ID NO: 44

EVQLVESGGGLVQPGGSLRLSCAASGYTFTAYGMNWVRQAPGKGLEWMG

WINTYTGESTYADSVKGRFTISADTSKNTAYLQMNSLRAEDTAVYYCARFAI

KGDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPS

NTKVDKKVEPKSCTRHRQPRGWEQKYNTVSFNLGEAYEYPTFIQDLRNELAK

GTPVCQLPVTLQTIADDKRFVLVDITTTSKKTVKVAIDVTDVYVVGYQDKWD

GKDRAVFLDKVPTVATSKLFPGVTNRVTLTFDGSYQKLV*H*AAKVDRKDLEL

GV*N*KLEFSIEAIHGKTINGQEIAKFFLIVIQMVSEAARFKYIETEVVDRGLYGSF

KPNFKVLNLENNWGDISDAIHKSSPQCTTINPALQLISPSNDPWVVNKVSQISP

DMGILKFKSSK (DI $V_L$-$C_L$-deBouganin4)

SEQ ID NO 45

DIQMTQSPSSLSASVGDRVTITCRSTKSLLHSNGITYLYWYQQKPGKAPKLLI

YQMSNLASGVPSRFSSSGSGTDFTLTISSLQPEDFATYYCAQNLEIPRTFGTGT

KVEIKRTVAAPSVFIFPPSDEQLKSGTASVVCLLNNFYPREAKVQWKVDNAL

-continued

QSGNSQESVTEQDSKDSTYSLSSTLTLSKADYEKHKVYACEVTHQGLSSPVT

KSFNRGEC

TRHRQPRGWEQKYNTVSFNLGEAYEYPTFIQDLRNELAKGTPVCQLPVTLQTI

ADDKRFVLVDITTTSKKTVKVAIDVTDVYVVGYQDKWDGKDRAVFLDKVPT

VATSKLFPGVTNRVTLTFDGSYQKLV*H*AAKVDRKDLELGV*N*KLEFSIEAIHG

KTINGQEIAKFFLIVIQMVSEAARFKYIETEVVDRGLYGSFKPNFKVLNLENN

WGDISDAIHKSSPQCTTINPALQLISPSNDPWVVNKVSQISPDMGILKFKSSK (Algo $V_H$-$C_H$-deBouganin 4)

SEQ ID NO: 46

EVQLQQSGPGLVQPGGSVRISCAASGYTFTAYGMNWVRQAPGKGLEWMGW

INTYTGESTYADSFKGRFEFSLDTHNSSAYLQIQSLREEDTAVYYCARFAIQG

DYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSCTRHRQPRGWEQKYNTVSFNLGEAYEYPTFIQDLRNELAKGTP

VCQLPVTLQTIADDKRFVLVDITTTSKKTVKVAIDVTDVYVVGYQDKWDGK

DRAVFLDKVPTVATSKLFPGVTNRVTLTFDGSYQKLV*H*AAKVDRKDLELGV

*N*KLEFSIEAIHGKTINGQEIAKFFLIVIQMVSEAARFKYIETEVVDRGLYGSFKP

NFKVLNLENNWGDISDAIHKSSPQCTTINPALQLISPSNDPWVVNKVSQISPD

MGILKFKSSK (Algo $V_L$-$C_L$-deBouganin 4)

SEQ ID NO: 47

DIQMTQSPSSLSASVGDRVTITCKSTKSLLHSNGITYLYWYQQKPGSAPKLLIY

QMSHLASGVPSRFSSSGSGTDFTLTISSLQPEDFATYYCAQNLEIPRTFGQGTK

VEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKS

FNRGEC

TRHRQPRGWEQKYNTVSFNLGEAYEYPTFIQDLRNELAKGTPVCQLPVTLQTI

ADDKRFVLVDITTTSKKTVKVAIDVTDVYVVGYQDKWDGKDRAVFLDKVPT

VATSKLFPGVTNRVTLTFDGSYQKLV*H*AAKVDRKDLELGV*N*KLEFSIEAIHG

KTINGQEIAKFFLIVIQMVSEAARFKYIETEVVDRGLYGSFKPNFKVLNLENN

WGDISDAIHKSSPQCTTINPALQLISPSNDPWVVNKVSQISPDMGILKFKSSK (Algo $V_H$(CDRsWT)-$C_H$-deBouganin4)

SEQ ID NO: 48

EVQLQQSGPGLVQPGGSVRISCAASGYTFTNYGMNWVRQAPGKGLEWMGW

INTYTGESTYADSFKGRFEFSLDTHNSSAYLQIQSLREEDTAVYYCARFAIKG

DYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSCTRHRQPRGWEQKYNTVSFNLGEAYEYPTFIQDLRNELAKGTP

VCQLPVTLQTIADDKRFVLVDITTTSKKTVKVAIDVTDVYVVGYQDKWDGK

DRAVFLDKVPTVATSKLFPGVTNRVTLTFDGSYQKLV*H*AAKVDRKDLELGV

*N*KLEFSIEAIHGKTINGQEIAKFFLIVIQMVSEAARFKYIETEVVDRGLYGSFKP

NFKVLNLENNWGDISDAIHKSSPQCTTINPALQLISPSNDPWVVNKVSQISPD

MGILKFKSSK

-continued (Algo $V_H$(CDRsWT + Treg)-$C_H$-deBouganin4)
SEQ ID NO: 49:

EVQLQQSGPGLVQPGGSVRISCAASGYTFTNYGMNWVRQAPGKGLEWMGW

INTYTGESTYADSFKGRFEFSLDTHNSSAYLQMNSLRAEDTAVYYCARFAIK

GDYWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSN

TKVDKKVEPKSCTRHRQPRGWEQKYNTVSFNLGEAVEYPTFIQDLRNELAKG

TPVCQLPVTLQTIADDKRFVLVDITTTSKKTVKVAIDVTDVYVVGYQDKWDG

KDRAVFLDKVPTVATSKLFPGVTNRVTLTFDGSYQKLV*H*AAKVDRKDLELG

V*N*KLEFSIEAIHGKTINGQEIAKFFLIVIQMVSEAARFKYIETEVVDRGLYGSFK

PNFKVLNLENNWGDISDAIHKSSPQCTTINPALQLISPSNDPWVVNKVSQISPD

MGILKFKSSK (WT $V_H$-$C_H$-deBouganin 3)

SEQ ID NO: 50

EVQLVQSGPGLVQPGGSVRISCAASGYTFTNYGMNWVKQAPGKGLEWMGW

INTYTGESTYADSFKGRFTFSLDTSASAAYLQINSLRAEDTAVYYCARFAIKG

DYWGQGTLLTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSCTRHRQPRGWEQKYNTVSFNLGEAVEYPTFIQDLRNELAKGTP

VCQLPVTLQTIADDKRFVLVDITTTSKKTVKVAIDVTDVYVVGYQDKWDGK

DRAVFLDKVPTVATSKLFPGVTNRVTLTFDGSYQKLV*H*AAK*A*DRK*A*LELGV

*N*KLEFSIEAIHGKTINGQE*A*AKFFLIVIQMVSEAARFKYIETEVVDRGLYGSFK

PNFKVLNLENNWGDISDAIHKSSPQCTTINPALQLISPSNDPWVVNKVSQISPD

MGILKFKSSK (WT $V_H$-$C_H$-deBouganin4)

SEQ ID NO: 51

EVQLVQSGPGLVQPGGSVRISCAASGYTFTNYGMNWVKQAPGKGLEWMGW

INTYTGESTYADSFKGRFTFSLDTSASAAYLQINSLRAEDTAVYYCARFAIKG

DYWGQGTLLTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTK

VDKKVEPKSCTRHRQPRGWEQKYNTVSFNLGEAYEYPTFIQDLRNELAKGTP

VCQLPVTLQTIADDKRFVLVDITTTSKKTVKVAIDVTDVYVVGYQDKWDGK

DRAVFLDKVPTVATSKLFPGVTNRVTLTFDGSYQKLV*H*AAKVDRKDLELGV

*N*KLEFSIEAIHGKTINGQEIAKFFLIVIQMVSEAARFKYIETEVVDRGLYGSFKP

NFKVLNLENNWGDISDAIHKSSPQCTTINPALQLISPSNDPWVVNKVSQISPD

MGILKFKSSK (WT $V_L$-$C_L$-deBouganin 3)

SEQ ID NO: 52

DIQMTQSPSSLSASVGDRVTITCRSTKSLLHSNGITYLYWYQQKPGKAPKLLI

YQMSNLASGVPSRFSSSGSGTDFTLTISSLQPEDFATYYCAQNLEIPRTFGQGT

KVELKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVT

KSFNRGECTRHRQPRGWEQKYNTVSFNLGEAYEYPTFIQDLRNELAKGTPVC

QLPVTLQTIADDKRFVLVDITTTSKKTVKVAIDVTDVYVVGYQDKWDGKDR

AVFLDKVPTVATSKLFPGVTNRVTLTFDGSYQKLV*H*AAK*A*DRK*A*LELGV*N*K

-continued

LEFSIEAIHGKTINGQE*A*AKFFLIVIQMVSEAARFKYIETEVVDRGLYGSFKPNF

KVLNLENNWGDISDAIHKSSPQCTTINPALQLISPSNDPWVVNKVSQISPDMGI

LKFKSSK (WT $V_L$-$C_L$-deBouganin 4)

SEQ ID NO: 53

DIQMTQSPSSLSASVGDRVTITCRSTKSLLHSNGITYLYWYQQKPGKAPKLLI

YQMSNLASGVPSRFSSSGSGTDFTLTISSLQPEDFATYYCAQNLEIPRTFGQGT

KVELKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVT

KSFNRGEC

TRHRQPRGWEQKYNTVSFNLGEAYEYPTFIQDLRNELAKGTPVCQLPVTLQTI

ADDKRFVLVDITTTSKKTVKVAIDVTDVYVVGYQDKWDGKDRAVFLDKVPT

VATSKLFPGVTNRVTLTFDGSYQKLV*H*AAKVDRKDLELGV*N*KLEFSIEAIHG

KTINGQEIAKFFLIVIQMVSEAARFKYIETEVVDRGLYGSFKPNFKVLNLENN

WGDISDAIHKSSPQCTTINPALQLISPSNDPWVVNKVSQISPDMGILKFKSSK

---

What is claimed is:

1. An antibody that binds to epithelial cell adhesion molecule (EpCAM) comprising:

a heavy chain having an amino acid sequence selected from SEQ ID NO: 1, SEQ ID NO: 11, SEQ ID NO: 31, and SEQ ID NO: 32, and a light chain having an amino acid sequence selected from SEQ ID NO: 2 and SEQ ID NO: 12.

2. An immunoconjugate comprising an antibody attached to an effector molecule, wherein the antibody binds to epithelial cell adhesion molecule (EpCAM) and comprises a heavy chain having an amino acid sequence selected from SEQ ID NO: 1, SEQ ID NO: 11, SEQ ID NO: 31, and SEQ ID NO: 32, and a light chain having an amino acid sequence selected from SEQ ID NO: 2 and SEQ ID NO: 12.

3. The immunoconjugate of claim 2, wherein the heavy chain has the amino acid sequence as shown in SEQ ID NO: 1 and the light chain has the amino acid sequence as shown in SEQ ID NO: 2.

4. The immunoconjugate of claim 2, wherein the heavy chain has the amino acid sequence as shown in SEQ ID NO: 11 and the light chain has the amino acid sequence as shown in SEQ ID NO: 12.

5. The immunoconjugate of claim 2, wherein the heavy chain has the amino acid sequence as shown in SEQ ID NO: 31 and the light chain has the amino acid sequence as shown in SEQ ID NO: 12.

6. The immunoconjugate of claim 2, wherein the heavy chain has the amino acid sequence as shown in SEQ ID NO: 32 and the light chain has the amino acid sequence as shown in SEQ ID NO: 12.

7. The immunoconjugate according to claim 2, wherein the antibody is an antibody fragment selected from the group consisting of Fab, Fab', F(ab')2, scFv, dsFv, ds-scFv, dimers, minibodies, diabodies, bispecific antibody fragments, non-immunoglobulin scaffolds, multimers, and any combination thereof.

8. The immunoconjugate according to claim 2, wherein the antibody is an antibody fragment Fab and wherein light chain and the heavy chain are linked by a covalent bond.

9. The immunoconjugate of claim 8, wherein the covalent bond is a disulfide bond.

10. The immunoconjugate according to claim 2, wherein the effector molecule is selected from the group consisting of a radioisotope, an antineoplastic agent, an immunomodulator, a biological response modifier, lectin, a toxin, a chromophore, a fluorophore, a chemiluminescent compound, an enzyme, a metal ion, and any combination thereof.

11. The immunoconjugate according to claim 2, wherein the effector molecule is a toxin selected from the group consisting of abrin, modeccin, viscumin, gelonin, bouganin, saporin, ricin, ricin A chain, bryodin, luffin, momordin, restrictocin, *Pseudomonas* exotoxin A, pertussis toxin, tetanus toxin, botulinum toxin, *Shigella* toxin, cholera toxin, diphtheria toxin, and any combination thereof.

12. The immunoconjugate according to claim 2, wherein the effector molecule is *Pseudomonas* exotoxin A (SEQ ID NO: 3).

13. The immunoconjugate according to claim 2, wherein the effector molecule is bouganin toxin (SEQ ID NO: 4).

14. The immunoconjugate according to claim 2, wherein the effector molecule is bouganin toxin selected from SEQ ID NO: 33, SEQ ID NO: 42, and SEQ ID NO: 43.

15. A composition comprising an immunoconjugate according to claim 2 and a pharmaceutically acceptable excipient, carrier, buffer or stabilizer.

16. A method of detecting or monitoring cancer in a subject comprising the steps of:

contacting a test sample taken from the subject with an antibody according to claim 1 to form an antibody-antigen complex;

measuring the amount of the antibody-antigen complex in the test sample; and normalizing the results against a control.

17. A method of imaging a tumor in a subject, the method comprising:

administering to the subject an antibody according to claim 1; and detecting the antibody by in vivo imaging.

18. A method of treating a subject with cancer, the method comprising:

administering to the subject a therapeutically effective amount of an immunoconjugate according to claim 2.

19. The method of claim 18, wherein the heavy chain has the amino acid sequence as shown in SEQ ID NO: 1 and the light chain has the amino acid sequence as shown in SEQ ID NO: 2.

20. The method of claim 18, wherein the heavy chain has the amino acid sequence as shown in SEQ ID NO: 11 and the light chain has the amino acid sequence as shown in SEQ ID NO: 12.

21. The method of claim 18, wherein the heavy chain has the amino acid sequence as shown in SEQ ID NO: 31 and the light chain has the amino acid sequence as shown in SEQ ID NO: 12.

22. The method of claim 18, wherein the heavy chain has the amino acid sequence as shown in SEQ ID NO: 32 and the light chain has the amino acid sequence as shown in SEQ ID NO: 12.

23. The method according to claim 18, wherein the antibody is an antibody fragment selected from the group consisting of Fab, Fab', F(ab')2, scFv, dsFv, ds-scFv, dimers, minibodies, diabodies, bispecific antibody fragments, non-immunoglobulin scaffolds, multimers, and any combination thereof.

24. The method according to claim 18, wherein the effector molecule is selected from the group consisting of a radioisotope, an antineoplastic agent, an immunomodulator, a biological response modifier, lectin, a toxin, a chromophore, a fluorophore, a chemiluminescent compound, an enzyme, a metal ion, and any combination thereof.

25. The method according to claim 18, wherein the administration of the immunoconjugate is by parenteral administration selected from the group consisting of subcutaneous, intramuscular, intraperitoneal, intracavity, intrathecal, intratumoral, transdermal and intravenous injection.

26. The method according to claim 18, wherein the immunoconjugate administration is at a dosage of about 0.01 mg/kg/dose to about 2000 mg/kg/dose.

27. The method according to claim 18, wherein the immunoconjugate is co-administered, concurrently administered, or sequentially administered with one or more anticancer agents.

28. The method of claim 27, wherein the anticancer agents are selected from tamoxifen, toremifen, raloxifene, droloxifene, iodoxyfene, megestrol acetate, anasfrozole, letrazole, borazole, exemestane, flutamide, nilutamide, bicalutamide, cyproterone acetate, goserelin acetate, luprolide, finasteride, herceptin, methotrexate, 5-fiuorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, Irinotecan, topotecan, epothilones, Iressa, Tarceva, angiogenesis inhibitors, EGF inhibitors, VEGF inhibitors, CDK inhibitors, cytokines, Her1 and Her2 inhibitors, and monoclonal antibodies.

29. The method according to claim 18, wherein the cancer is selected from the group consisting of lung cancer, gastric cancer, renal cancer, thyroid cancer, breast cancer, bladder cancer, ovarian cancer, colorectal cancer, head and neck cancer, hepatocellular carcinoma, esophageal, pancreas, and prostate cancer.

* * * * *

SEQUENCE LISTING

<160> NUMBER OF SEQ ID NOS: 53

<210> SEQ ID NO 1
<211> LENGTH: 219
<212> TYPE: PRT
<213> ORGANISM: Artificial Sequence
<220> FEATURE:
<223> OTHER INFORMATION: de-immunized VH-CH or DI VH-CH

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ala Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Gln Thr Tyr Ile Cys Asn Val Asn His Lys Pro Ser Asn Thr
        195                 200                 205

Lys Val Asp Lys Lys Val Glu Pro Lys Ser Cys
    210                 215


<210> SEQ ID NO 2
<211> LENGTH: 219
<212> TYPE: PRT
<213> ORGANISM: Artificial Sequence
<220> FEATURE:
<223> OTHER INFORMATION: de-immunized VL-CL or DI VL-CL

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Thr Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 3
<211> LENGTH: 356
<212> TYPE: PRT
<213> ORGANISM: Artificial Sequence
<220> FEATURE:
<223> OTHER INFORMATION: ETA toxin 252-608

<400> SEQUENCE: 3

Glu Gly Gly Ser Leu Ala Ala Leu Thr Ala His Gln Ala Cys His Leu
1               5                   10                  15

Pro Leu Glu Thr Phe Thr Arg His Arg Gln Pro Arg Gly Trp Glu Gln
            20                  25                  30

Leu Glu Gln Cys Gly Tyr Pro Val Gln Arg Leu Val Ala Leu Tyr Leu
        35                  40                  45

Ala Ala Arg Leu Ser Trp Asn Gln Val Asp Gln Val Ile Arg Asn Ala
    50                  55                  60
```

```
Leu Ala Ser Pro Gly Ser Gly Gly Asp Leu Gly Glu Ala Ile Arg Glu
65                  70                  75                  80

Gln Pro Glu Gln Ala Arg Leu Ala Leu Thr Leu Ala Ala Ala Glu Ser
                85                  90                  95

Glu Arg Phe Val Arg Gln Gly Thr Gly Asn Asp Glu Ala Gly Ala Ala
            100                 105                 110

Ser Ala Asp Val Val Ser Leu Thr Cys Pro Val Ala Ala Gly Glu Cys
        115                 120                 125

Ala Gly Pro Ala Asp Ser Gly Asp Ala Leu Leu Glu Arg Asn Tyr Pro
    130                 135                 140

Thr Gly Ala Glu Phe Leu Gly Asp Gly Gly Asp Val Ser Phe Ser Thr
145                 150                 155                 160

Arg Gly Thr Gln Asn Trp Thr Glu Arg Leu Leu Gln Ala His Arg Gln
                165                 170                 175

Leu Glu Glu Arg Gly Tyr Val Phe Val Gly Tyr His Gly Thr Phe Leu
            180                 185                 190

Glu Ala Ala Gln Ser Ile Val Phe Gly Gly Val Arg Ala Arg Ser Gln
        195                 200                 205

Asp Leu Asp Ala Ile Trp Arg Gly Phe Tyr Ile Ala Gly Asp Pro Ala
    210                 215                 220

Leu Ala Tyr Gly Tyr Ala Gln Asp Gln Glu Pro Asp Ala Arg Gly Arg
225                 230                 235                 240

Ile Arg Asn Gly Ala Leu Leu Arg Val Tyr Val Pro Arg Ser Ser Leu
                245                 250                 255

Pro Gly Phe Tyr Arg Thr Gly Leu Thr Leu Ala Ala Pro Glu Ala Ala
            260                 265                 270

Gly Glu Val Glu Arg Leu Leu Gly His Pro Leu Pro Leu Arg Leu Asp
        275                 280                 285

Ala Ile Thr Gly Pro Glu Glu Glu Gly Gly Arg Leu Glu Thr Ile Leu
    290                 295                 300

Gly Trp Pro Leu Ala Glu Arg Thr Val Val Ile Pro Ser Ala Ile Pro
305                 310                 315                 320

Thr Asp Pro Arg Asn Val Gly Gly Asp Leu Asp Pro Ser Ser Ile Pro
                325                 330                 335

Asp Lys Glu Gln Ala Ile Ser Ala Leu Pro Asp Tyr Ala Ser Gln Pro
            340                 345                 350

Gly Lys Pro Pro
        355


<210> SEQ ID NO 4
<211> LENGTH: 250
<212> TYPE: PRT
<213> ORGANISM: Artificial Sequence
<220> FEATURE:
<223> OTHER INFORMATION: modified bouganin protein

<400> SEQUENCE: 4

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60
```

-continued

```
Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Ala Asp Arg Lys Ala Leu
        115                 120                 125

Glu Leu Gly Val Asn Lys Leu Glu Phe Ser Ile Glu Ala Ile His Gly
    130                 135                 140

Lys Thr Ile Asn Gly Gln Glu Ala Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250


<210> SEQ ID NO 5
<211> LENGTH: 219
<212> TYPE: PRT
<213> ORGANISM: Artificial Sequence
<220> FEATURE:
<223> OTHER INFORMATION: wild-type VH-CH or WT VH-CH

<400> SEQUENCE: 5

Glu Val Gln Leu Val Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Thr Phe Ser Leu Asp Thr Ser Ala Ser Ala Ala Tyr
65                  70                  75                  80

Leu Gln Ile Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys
    210                 215
```

<210> SEQ ID NO 6
<211> LENGTH: 219
<212> TYPE: PRT
<213> ORGANISM: Artificial Sequence
<220> FEATURE:
<223> OTHER INFORMATION: wild-type VL-CL or WT VL-CL

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 7
<211> LENGTH: 1588
<212> TYPE: DNA
<213> ORGANISM: Artificial Sequence
<220> FEATURE:
<223> OTHER INFORMATION: DNA sequence of de-immunized VB5-845

<400> SEQUENCE: 7

```
ctgcaggtct atggaacgat aaatgcccat gaaaattcta tttcaaggag acagtcataa     60

tgaaatacct attgcctacg gcagccgctg gattgttatt actcgctgcc caaccagcga    120

tggcggaagt acagctggtc gaatccggtg gtggtctggt tcagccgggt ggtagcctgc    180

gtctgagctg cgcggcgagc ggttacacct tcaccgcgta cggtatgaac tgggttcgtc    240
```

-continued

```
aggctccggg taaaggtttg gaatggatgg gttggatcaa cacctatacc ggtgagtcta    300

cctacgctga tagcgttaaa ggccgtttca ccatcagcgc tgacactagc aaaaacaccg    360

cgtacctgca gatgaactct ctgcgtgctg aggacactgc ggtttactac tgcgctcgtt    420

tcgcgatcaa aggtgactat tggggtcagg gtactctggt taccgttagc agcgctagca    480

ctaagggccc gtccgttttc ccactggctc cgtcttctaa aagcacttct ggtggtaccg    540

cggctctggg ttgccttgtt aaagactact tccctgaacc ggtcaccgtt agctggaact    600

ccggtgcgtt gacctctggt gttcacacct tcccagcggt tctgcagtct agcggtctgt    660

atagcctgag ctctgtagtt accgttccgt cttctagcct gggtacgcag acctacatct    720

gcaacgtgaa ccacaaaccg agcaacacta aagtggataa aaaagttgaa ccgaagtctt    780

gctagtaatc tagagtcgac ctgcaggtct atggaacgat aaatgcccat gaaaattcta    840

tttcaaggag acagtcataa tgaaatacct tctgccgacc gctgccgctg gtctgctgct    900

gttggctgct caaccggcta tggcagacat ccagatgacc cagtccccgt ctagcctgag    960

cgcaagcgtt ggtgaccgtg tgaccatcac ctgccgtagc actaaatccc tgctgcactc   1020

taacggcatc acctacctgt attggtacca acagaaaccg ggtaaagctc cgaaactgct   1080

gatctaccag atgtctaacc tggctagcgg cgttccttct cgtttttctt ctagcggtag   1140

cggtactgac ttcaccctga ccattagctc tctgcagcct gaagactttg cgacctacta   1200

ttgcgctcag aaccttgaaa tcccgcgtac cttcggcacc ggtaccaaag ttgaaatcaa   1260

gcgtaccgtt gcggctccgt ctgttttcat cttcccacct agcgatgaac agcttaaatc   1320

tggtactgct agcgtagttt gcctgcttaa caacttctac cctcgtgaag ctaaagttca   1380

gtggaaagtt gacaacgctc tgcagtctgg taactctcag gaatctgtga ccgaacagga   1440

tagcaaagat agcacctata gcctgtctag caccctgacc cttagcaagg cggactatga   1500

aaaacacaaa gtttacgctt gcgaggtgac ccaccaaggt ctgtcttctc cggtgactaa   1560

atcctttaac cgtggcgaat gctagtga                                     1588


<210> SEQ ID NO 8
<211> LENGTH: 253
<212> TYPE: PRT
<213> ORGANISM: Artificial Sequence
<220> FEATURE:
<223> OTHER INFORMATION: 4D5MOC-B

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg Thr Pro Ser His Asn Ser His Gln Val Pro Ser Ala Gly Gly Pro
```

```
        115                 120                 125

Thr Ala Asn Ser Gly Thr Ser Gly Ser Glu Val Gln Leu Val Gln Ser
    130                 135                 140

Gly Pro Gly Leu Val Gln Pro Gly Gly Ser Val Arg Ile Ser Cys Ala
145                 150                 155                 160

Ala Ser Gly Tyr Thr Phe Thr Asn Tyr Gly Met Asn Trp Val Lys Gln
                165                 170                 175

Ala Pro Gly Lys Gly Leu Glu Trp Met Gly Trp Ile Asn Thr Tyr Thr
            180                 185                 190

Gly Glu Ser Thr Tyr Ala Asp Ser Phe Lys Gly Arg Phe Thr Phe Ser
        195                 200                 205

Leu Asp Thr Ser Ala Ser Ala Ala Tyr Leu Gln Ile Asn Ser Leu Arg
    210                 215                 220

Ala Glu Asp Thr Ala Val Tyr Tyr Cys Ala Arg Phe Ala Ile Lys Gly
225                 230                 235                 240

Asp Tyr Trp Gly Gln Gly Thr Leu Leu Thr Val Ser Ser
                245                 250


<210> SEQ ID NO 9
<211> LENGTH: 250
<212> TYPE: PRT
<213> ORGANISM: Artificial Sequence
<220> FEATURE:
<223> OTHER INFORMATION: modified bouganin protein
<220> FEATURE:
<221> NAME/KEY: MISC_FEATURE
<222> LOCATION: (123)..(123)
<223> OTHER INFORMATION: Xaa is Thr or Ala or Gln
<220> FEATURE:
<221> NAME/KEY: MISC_FEATURE
<222> LOCATION: (127)..(127)
<223> OTHER INFORMATION: Xaa is Gly or Ala
<220> FEATURE:
<221> NAME/KEY: MISC_FEATURE
<222> LOCATION: (129)..(129)
<223> OTHER INFORMATION: Xaa is Gln or Gly or Glu
<220> FEATURE:
<221> NAME/KEY: MISC_FEATURE
<222> LOCATION: (133)..(133)
<223> OTHER INFORMATION: Xaa is Asn or Asp or Thr or Ala or Arg or Gln
      or Glu or Gly or His or Lys or Ser
<220> FEATURE:
<221> NAME/KEY: MISC_FEATURE
<222> LOCATION: (152)..(152)
<223> OTHER INFORMATION: Xaa is Gln or Ala

<400> SEQUENCE: 9

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Xaa Asp Arg Lys Xaa Leu
```

```
        115                 120                 125

Xaa Leu Gly Val Xaa Lys Leu Glu Phe Ser Ile Glu Ala Ile His Gly
    130                 135                 140

Lys Thr Ile Asn Gly Gln Glu Xaa Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250


<210> SEQ ID NO 10
<211> LENGTH: 750
<212> TYPE: PRT
<213> ORGANISM: Artificial Sequence
<220> FEATURE:
<223> OTHER INFORMATION: VB6-845

<400> SEQUENCE: 10

Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Gln Ser Gly Pro Gly
            20                  25                  30

Leu Val Gln Pro Gly Gly Ser Val Arg Ile Ser Cys Ala Ala Ser Gly
        35                  40                  45

Tyr Thr Phe Thr Asn Tyr Gly Met Asn Trp Val Lys Gln Ala Pro Gly
    50                  55                  60

Lys Gly Leu Glu Trp Met Gly Trp Ile Asn Thr Tyr Thr Gly Glu Ser
65                  70                  75                  80

Thr Tyr Ala Asp Ser Phe Lys Gly Arg Phe Thr Phe Ser Leu Asp Thr
                85                  90                  95

Ser Ala Ser Ala Ala Tyr Leu Gln Ile Asn Ser Leu Arg Ala Glu Asp
            100                 105                 110

Thr Ala Val Tyr Tyr Cys Ala Arg Phe Ala Ile Lys Gly Asp Tyr Trp
        115                 120                 125

Gly Gln Gly Thr Leu Leu Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
```

-continued

```
225                 230                 235                 240

Cys Thr Arg His Arg Gln Pro Arg Gly Trp Glu Gln Leu Tyr Asn Thr
                245                 250                 255

Val Ser Phe Asn Leu Gly Glu Ala Tyr Glu Tyr Pro Thr Phe Ile Gln
            260                 265                 270

Asp Leu Arg Asn Glu Leu Ala Lys Gly Thr Pro Val Cys Gln Leu Pro
        275                 280                 285

Val Thr Leu Gln Thr Ile Ala Asp Asp Lys Arg Phe Val Leu Val Asp
    290                 295                 300

Ile Thr Thr Thr Ser Lys Lys Thr Val Lys Val Ala Ile Asp Val Thr
305                 310                 315                 320

Asp Val Tyr Val Val Gly Tyr Gln Asp Lys Trp Asp Gly Lys Asp Arg
                325                 330                 335

Ala Val Phe Leu Asp Lys Val Pro Thr Val Ala Thr Ser Lys Leu Phe
            340                 345                 350

Pro Gly Val Thr Asn Arg Val Thr Leu Thr Phe Asp Gly Ser Tyr Gln
        355                 360                 365

Lys Leu Val Asn Ala Ala Lys Ala Asp Arg Lys Ala Leu Glu Leu Gly
    370                 375                 380

Val Asn Lys Leu Glu Phe Ser Ile Glu Ala Ile His Gly Lys Thr Ile
385                 390                 395                 400

Asn Gly Gln Glu Ala Ala Lys Phe Phe Leu Ile Val Ile Gln Met Val
                405                 410                 415

Ser Glu Ala Ala Arg Phe Lys Tyr Ile Glu Thr Glu Val Val Asp Arg
            420                 425                 430

Gly Leu Tyr Gly Ser Phe Lys Pro Asn Phe Lys Val Leu Asn Leu Glu
        435                 440                 445

Asn Asn Trp Gly Asp Ile Ser Asp Ala Ile His Lys Ser Ser Pro Gln
    450                 455                 460

Cys Thr Thr Ile Asn Pro Ala Leu Gln Leu Ile Ser Pro Ser Asn Asp
465                 470                 475                 480

Pro Trp Val Val Asn Lys Val Ser Gln Ile Ser Pro Asp Met Gly Ile
                485                 490                 495

Leu Lys Phe Lys Ser Ser Lys Met Lys Tyr Leu Leu Pro Thr Ala Ala
            500                 505                 510

Ala Gly Leu Leu Leu Leu Ala Ala Gln Pro Ala Met Ala His His His
        515                 520                 525

His His His Asp Ile Gln Met Thr Gln Ser Pro Ser Ser Leu Ser Ala
    530                 535                 540

Ser Val Gly Asp Arg Val Thr Ile Thr Cys Arg Ser Thr Lys Ser Leu
545                 550                 555                 560

Leu His Ser Asn Gly Ile Thr Tyr Leu Tyr Trp Tyr Gln Gln Lys Pro
                565                 570                 575

Gly Lys Ala Pro Lys Leu Leu Ile Tyr Gln Met Ser Asn Leu Ala Ser
            580                 585                 590

Gly Val Pro Ser Arg Phe Ser Ser Ser Gly Ser Gly Thr Asp Phe Thr
        595                 600                 605

Leu Thr Ile Ser Ser Leu Gln Pro Glu Asp Phe Ala Thr Tyr Tyr Cys
    610                 615                 620

Ala Gln Asn Leu Glu Ile Pro Arg Thr Phe Gly Gln Gly Thr Lys Val
625                 630                 635                 640

Glu Leu Lys Arg Thr Val Ala Ala Pro Ser Val Phe Ile Phe Pro Pro
                645                 650                 655
```

```
Ser Asp Glu Gln Leu Lys Ser Gly Thr Ala Ser Val Val Cys Leu Leu
            660                 665                 670

Asn Asn Phe Tyr Pro Arg Glu Ala Lys Val Gln Trp Lys Val Asp Asn
        675                 680                 685

Ala Leu Gln Ser Gly Asn Ser Gln Glu Ser Val Thr Glu Gln Asp Ser
    690                 695                 700

Lys Asp Ser Thr Tyr Ser Leu Ser Ser Thr Leu Thr Leu Ser Lys Ala
705                 710                 715                 720

Asp Tyr Glu Lys His Lys Val Tyr Ala Cys Glu Val Thr His Gln Gly
                725                 730                 735

Leu Ser Ser Pro Val Thr Lys Ser Phe Asn Arg Gly Glu Cys
            740                 745                 750


<210> SEQ ID NO 11
<211> LENGTH: 219
<212> TYPE: PRT
<213> ORGANISM: Artificial Sequence
<220> FEATURE:
<223> OTHER INFORMATION: Algo VH-CH

<400> SEQUENCE: 11

Glu Val Gln Leu Gln Gln Ser Gly Pro Gly Leu Val Gln Pro Gly Gly
1               5                   10                  15

Ser Val Arg Ile Ser Cys Ala Ala Ser Gly Tyr Thr Phe Thr Ala Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
65                  70                  75                  80

Leu Gln Ile Gln Ser Leu Arg Glu Glu Asp Thr Ala Val Tyr Tyr Cys
                85                  90                  95

Ala Arg Phe Ala Ile Gln Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys
    210                 215


<210> SEQ ID NO 12
<211> LENGTH: 219
<212> TYPE: PRT
<213> ORGANISM: Artificial Sequence
<220> FEATURE:
<223> OTHER INFORMATION: Algo VL-CL
```

<400> SEQUENCE: 12

Asp Ile Gln Met Thr Gln Ser Pro Ser Ser Leu Ser Ala Ser Val Gly
1 5 10 15

Asp Arg Val Thr Ile Thr Cys Lys Ser Thr Lys Ser Leu Leu His Ser
20 25 30

Asn Gly Ile Thr Tyr Leu Tyr Trp Tyr Gln Gln Lys Pro Gly Ser Ala
35 40 45

Pro Lys Leu Leu Ile Tyr Gln Met Ser His Leu Ala Ser Gly Val Pro
50 55 60

Ser Arg Phe Ser Ser Ser Gly Ser Gly Thr Asp Phe Thr Leu Thr Ile
65 70 75 80

Ser Ser Leu Gln Pro Glu Asp Phe Ala Thr Tyr Tyr Cys Ala Gln Asn
85 90 95

Leu Glu Ile Pro Arg Thr Phe Gly Gln Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 13
<211> LENGTH: 481
<212> TYPE: PRT
<213> ORGANISM: Artificial Sequence
<220> FEATURE:
<223> OTHER INFORMATION: DI VH-CH-deBouganin

<400> SEQUENCE: 13

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Thr Phe Thr Ala Tyr
20 25 30

Gly Met Asn Trp Val Arg Gln Ala Pro Gly Lys Gly Leu Glu Trp Met
35 40 45

Gly Trp Ile Asn Thr Tyr Thr Gly Glu Ser Thr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Phe Ala Ile Lys Gly Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu

```
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val Asn Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 14
<211> LENGTH: 481
<212> TYPE: PRT
<213> ORGANISM: Artificial Sequence
<220> FEATURE:
<223> OTHER INFORMATION: Algo VH-CH-deBouganin

<400> SEQUENCE: 14

Glu Val Gln Leu Gln Gln Ser Gly Pro Gly Leu Val Gln Pro Gly Gly
1               5                   10                  15
```

-continued

```
Ser Val Arg Ile Ser Cys Ala Ala Ser Gly Tyr Thr Phe Thr Ala Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
65                  70                  75                  80

Leu Gln Ile Gln Ser Leu Arg Glu Glu Asp Thr Ala Val Tyr Tyr Cys
                85                  90                  95

Ala Arg Phe Ala Ile Gln Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val Asn Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430
```

```
Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 15
<211> LENGTH: 481
<212> TYPE: PRT
<213> ORGANISM: Artificial Sequence
<220> FEATURE:
<223> OTHER INFORMATION: WT VH-CH-deBouganin

<400> SEQUENCE: 15

Glu Val Gln Leu Val Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Thr Phe Ser Leu Asp Thr Ser Ala Ser Ala Ala Tyr
65                  70                  75                  80

Leu Gln Ile Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
```

```
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val Asn Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 16
<211> LENGTH: 481
<212> TYPE: PRT
<213> ORGANISM: Artificial Sequence
<220> FEATURE:
<223> OTHER INFORMATION: DI VL-CL-deBouganin

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Thr Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
        195                 200                 205

Pro Val Thr Lys Ser Phe Asn Arg Gly Glu Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val Asn Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 17
<211> LENGTH: 481
<212> TYPE: PRT
<213> ORGANISM: Artificial Sequence
<220> FEATURE:
<223> OTHER INFORMATION: Algo VL-CL-deBouganin

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ser Thr Lys Ser Leu Leu His Ser
            20                  25                  30

Asn Gly Ile Thr Tyr Leu Tyr Trp Tyr Gln Gln Lys Pro Gly Ser Ala
        35                  40                  45

Pro Lys Leu Leu Ile Tyr Gln Met Ser His Leu Ala Ser Gly Val Pro
    50                  55                  60
```

-continued

```
Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val Asn Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys
```

<210> SEQ ID NO 18
<211> LENGTH: 481
<212> TYPE: PRT
<213> ORGANISM: Artificial Sequence
<220> FEATURE:
<223> OTHER INFORMATION: WT VL-CL-deBouganin

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val Asn Ala Ala
            340                 345                 350

Lys Ala Asp Arg Lys Ala Leu Glu Leu Gly Val Asn Lys Leu Glu Phe
        355                 360                 365
```

```
Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 19
<211> LENGTH: 788
<212> TYPE: DNA
<213> ORGANISM: Artificial Sequence
<220> FEATURE:
<223> OTHER INFORMATION: Nucleotide sequence of DI VH-CH

<400> SEQUENCE: 19

ctgcaggtct atggaacgat aaatgcccat gaaaattcta tttcaaggag acagtcataa      60

tgaaatacct attgcctacg gcagccgctg gattgttatt actcgctgcc caaccagcga     120

tggcggaagt acagctggtc gaatccggtg gtggtctggt tcagccgggt ggtagcctgc     180

gtctgagctg cgcggcgagc ggttacacct tcaccgcgta cggtatgaac tgggttcgtc     240

aggctccggg taaaggtttg gaatggatgg gttggatcaa cacctatacc ggtgagtcta     300

cctacgctga tagcgttaaa ggccgtttca ccatcagcgc tgacacttct aaaaacaccg     360

cgtacctgca gatgaactct ctgcgtgctg aggacactgc ggtttactac tgcgctcgtt     420

tcgcgatcaa aggtgactat tggggtcagg gtactctggt taccgttagc agcgctagca     480

ctaagggccc gtccgttttc ccactggctc cgtcttctaa aagcacttct ggtggtaccg     540

cggctctggg ttgccttgtt aaagactact tccctgaacc ggtcaccgtt agctggaact     600

ccggtgcgtt gacctctggt gttcacacct tcccagcggt tctgcagtct agcggtctgt     660

atagcctgag ctctgtagtt accgttccgt cttctagcct gggtacgcag acctacatct     720

gcaacgtgaa ccacaaaccg agcaacacta aagtggataa aaaagttgaa ccgaagtctt     780

gctagtaa                                                              788


<210> SEQ ID NO 20
<211> LENGTH: 788
<212> TYPE: DNA
<213> ORGANISM: Artificial Sequence
<220> FEATURE:
<223> OTHER INFORMATION: Nucleotide sequence of DI VL-CL

<400> SEQUENCE: 20

ctgcaggtct atggaacgat aaatgcccat gaaaattcta tttcaaggag acagtcataa      60

tgaaatacct tctgccgacc gctgccgctg gtctgctgct gttggctgct caaccggcta     120

tggcagacat ccagatgacc cagtccccgt ctagcctgag cgcaagcgtt ggtgaccgtg     180

tgaccatcac ctgccgtagc actaaatccc tgctgcactc taacggcatc acctacctgt     240
```

attggtacca acagaaaccg ggtaaagctc cgaaactgct gatctaccag atgtctaacc 300
tggctagcgg cgttccttct cgtttttctt ctagcggtag cggtactgac ttcaccctga 360
ccattagctc tctgcagcct gaagactttg cgacctacta ttgcgctcag aaccttgaaa 420
tcccgcgtac cttcggcacc ggtaccaaag ttgaaatcaa gcgtaccgtt gcggctccgt 480
ctgttttcat cttcccacct agcgatgaac agcttaaatc tggtactgct agcgtagttt 540
gcctgcttaa caacttctac cctcgtgaag ctaaagttca gtggaaagtt gacaacgctc 600
tgcagtctgg taactctcag gaatctgtga ccgaacagga tagcaaagat agcacctata 660
gcctgtctag caccctgacc cttagcaagg cggactatga aaaacacaaa gtttacgctt 720
gcgaggtgac ccaccaaggt ctgtcttctc cggtgactaa atcctttaac cgtggcgaat 780
gctagtga 788

<210> SEQ ID NO 21
<211> LENGTH: 788
<212> TYPE: DNA
<213> ORGANISM: Artificial Sequence
<220> FEATURE:
<223> OTHER INFORMATION: Nucleotide sequence of WT VH-CH

<400> SEQUENCE: 21
ctgcaggtct atggaacgat aaatgcccat gaaaattcta tttcaaggag acagtcataa 60
tgaaatacct attgcctacg gcagccgctg gattgttatt actcgctgcc caaccagcga 120
tggcggaagt acagctggtt cagtccggcc cgggtcttgt tcaaccgggt ggttccgttc 180
gtatctcttg cgctgcttct ggttacacgt tcaccaacta cggcatgaac tgggtcaaac 240
aggctccggg taaaggcctg gaatggatgg gctggatcaa cacctacacc ggtgaatcca 300
cctacgctga ctccttcaaa ggtcgcttca ctttctccct cgacacaagt gctagtgctg 360
catacctcca aatcaactcg ctgcgtgcag aggatacagc agtctattac tgcgcccgtt 420
tcgctatcaa aggtgactac tggggtcaag gcacgctgct gaccgtttcc tcggctagca 480
ccaaaggccc atcggtcttc cccctggcac cctcctccaa gagcacctct gggggcacag 540
cggccctggg ctgcctggtc aaggactact tccccgaacc ggtgacggtg tcgtggaact 600
caggcgccct gaccagcggc gtgcacacct tcccggctgt cctacagtcc tcaggactct 660
actccctcag cagcgtggtg accgtgccct ccagcagctt gggcacccag acctacatct 720
gcaacgtgaa tcacaagccc agcaacacca aggtggacaa gaaagttgag cccaaatctt 780
gttagtga 788

<210> SEQ ID NO 22
<211> LENGTH: 806
<212> TYPE: DNA
<213> ORGANISM: Artificial Sequence
<220> FEATURE:
<223> OTHER INFORMATION: Nucleotide sequence of WT VL-CL

<400> SEQUENCE: 22
ctgcaggtct atggaacgat aaatgcccat gaaaattcta tttcaaggag acagtcataa 60
tgaaatacct attgcctacg gcagccgctg gattgttatt actcgctgcc caaccagcga 120
tggcgcacca tcatcaccat cacgatatcc agatgaccca gtccccgtcc tccctgagtg 180
cttctgttgg tgaccgtgtt accatcacct gccgttccac caaatccctc ctgcactcca 240
acggtatcac ctacctttat tggtatcaac agaaaccggg taaagctccg aaacttctga 300

```
tctaccagat gtccaacctg gcttccggtg ttccgtctcg tttctccagt tctggttctg    360

gtaccgactt caccctgacc atctcttctc tgcagccgga agacttcgct acctactact    420

gcgctcagaa cctggaaatc ccgcgtacct tcggtcaggg taccaaagtt gaacttaagc    480

gcactgtggc tgcaccatct gtcttcatct tcccgccatc tgatgagcag ttgaaatctg    540

gaactgcctc tgttgtgtgc ctgctgaata acttctatcc cagagaggcc aaagtacagt    600

ggaaggtgga taacgccctc caatcgggta actcccagga gagtgtcaca gagcaggaca    660

gcaaggacag cacctacagc ctcagcagca ccctgacgct gagcaaagca gactacgaga    720

aacacaaagt ctacgcctgc gaagtcaccc atcagggcct gagctcgccc gtcacaaaga    780

gcttcaacag gggagagtgt tagtga                                         806


<210> SEQ ID NO 23
<211> LENGTH: 794
<212> TYPE: DNA
<213> ORGANISM: Artificial Sequence
<220> FEATURE:
<223> OTHER INFORMATION: Nucleotide sequence of Algo VH-CH

<400> SEQUENCE: 23

gaattcctgc aggtctatgg aacgataaat gcccatgaaa attctatttc aaggagacag     60

tcataatgaa atacctattg cctacggcag ccgctggatt gttattactc gctgcccaac    120

cagcgatggc ggaagtacag ctgcagcagt ccggtccggg tctggttcag ccgggtggta    180

gcgttcgtat tagctgcgcg gcgagcggtt acaccttcac cgcgtacggt atgaactggg    240

ttcgtcaggc tccgggtaaa ggtttggaat ggatgggttg gatcaacacc tataccggtg    300

agtctaccta cgctgatagc ttcaaaggcc gtttcgaatt tagccttgac actcacaaca    360

gctctgcgta cctgcagatt cagtctctgc gtgaagagga cactgcggtt tactactgcg    420

ctcgtttcgc gatccagggt gactattggg gtcagggtac tctggttacc gttagcagcg    480

ctagcactaa gggcccgtcc gttttcccac tggctccgtc ttctaaaagc acttctggtg    540

gtaccgcggc tctgggttgc cttgttaaag actacttccc tgaaccggtc accgttagct    600

ggaactccgg tgcgttgacc tctggtgttc acaccttccc agcggttctg cagtctagcg    660

gtctgtatag cctgagctct gtagttaccg ttccgtcttc tagcctgggt acgcagacct    720

acatctgcaa cgtgaaccac aaaccgagca acactaaagt ggataaaaaa gttgaaccga    780

agtcttgcta gtaa                                                      794


<210> SEQ ID NO 24
<211> LENGTH: 794
<212> TYPE: DNA
<213> ORGANISM: Artificial Sequence
<220> FEATURE:
<223> OTHER INFORMATION: Nucleotide sequence of Algo VL-CL

<400> SEQUENCE: 24

tctagagtcg acctgcaggt ctatggaacg ataaatgccc atgaaaattc tatttcaagg     60

agacagtcat aatgaaatac cttctgccga ccgctgccgc tggtctgctg ctgttggctg    120

ctcaaccggc tatggcagac atccagatga cccagtcccc gtctagcctg agcgcaagcg    180

ttggtgaccg tgtgaccatc acctgcaaaa gcactaaatc cctgctgcac tctaacggca    240

tcacctacct gtattggtac caacagaaac cgggttctgc tccgaaactg ctgatctacc    300

agatgtctca cctggctagc ggcgttcctt ctcgtttttc ttctagcggt agcggtactg    360

acttcaccct gaccattagc tctctgcagc ctgaagactt tgcgacctac tattgcgctc    420
```

agaaccttga aatcccgcgt accttcggcc agggtaccaa agttgaaatc aagcgtaccg 480
ttgcggctcc gtctgttttc atcttcccac ctagcgatga acagcttaaa tctggtactg 540
ctagcgtagt ttgcctgctt aacaacttct accctcgtga agctaaagtt cagtggaaag 600
ttgacaacgc tctgcagtct ggtaactctc aggaatctgt gaccgaacag gatagcaaag 660
atagcaccta tagcctgtct agcaccctga cccttagcaa ggcggactat gaaaaacaca 720
aagtttacgc ttgcgaggtg acccaccaag gtctgtcttc tccggtgact aaatccttta 780
accgtggcga atgc 794

<210> SEQ ID NO 25
<211> LENGTH: 1580
<212> TYPE: DNA
<213> ORGANISM: Artificial Sequence
<220> FEATURE:
<223> OTHER INFORMATION: Nucleotide sequence of DI VH-CH-deBouganin

<400> SEQUENCE: 25
ctgcaggtct atggaacgat aaatgcccat gaaaattcta tttcaaggag acagtcataa 60
tgaaatacct attgcctacg gcagccgctg gattgttatt actcgctgcc caaccagcga 120
tggcggaagt acagctggtc gaatccggtg gtggtctggt tcagccgggt ggtagcctgc 180
gtctgagctg cgcggcgagc ggttacacct tcaccgcgta cggtatgaac tgggttcgtc 240
aggctccggg taaaggtttg gaatggatgg gttggatcaa cacctatacc ggtgagtcta 300
cctacgctga tagcgttaaa ggccgtttca ccatcagcgc tgacacttct aaaaacaccg 360
cgtacctgca gatgaactct ctgcgtgctg aggacactgc ggtttactac tgcgctcgtt 420
tcgcgatcaa aggtgactat tggggtcagg gtactctggt taccgttagc agcgctagca 480
ctaagggccc gtccgttttc ccactggctc cgtcttctaa aagcacttct ggtggtaccg 540
cggctctggg ttgccttgtt aaagactact tccctgaacc ggtcaccgtt agctggaact 600
ccggtgcgtt gacctctggt gttcacacct tcccagcggt tctgcagtct agcggtctgt 660
atagcctgag ctctgtagtt accgttccgt cttctagcct gggtacgcag acctacatct 720
gcaacgtgaa ccacaaaccg agcaacacta aagtggataa aaaagttgaa ccgaagtctt 780
gcacccgtca ccgtcagccg cgtggttggg aacagaaata taacaccgta tcttttaacc 840
tgggtgaggc gtatgaatac ccgaccttca tccaggacct gcgtaatgaa cttgctaaag 900
gtacccctgt ttgccagctg cctgtgaccc tgcagaccat cgctgatgat aaacgtttcg 960
ttctggttga cattaccacc acctccaaaa aaaccgttaa agtcgcgatc gatgtgaccg 1020
acgtttacgt ggtaggttac caggataaat gggacggtaa agatcgtgcg gttttcctgg 1080
acaaagttcc gaccgtagcg acttctaaac tgttcccagg tgtgaccaac cgtgtgaccc 1140
tgaccttcga cggcagctat cagaaactgg ttaacgcggc caaagctgat cgtaaagctc 1200
tcgaactggg tgttaacaaa ctggagttca gcattgaagc tatccacggt aaaaccatca 1260
acggtcaaga agcagctaaa ttcttcctga tcgtgatcca gatggttagc gaagcagcgc 1320
gttttaaata cattgaaacc gaagtagttg atcgtggtct gtatggtagc ttcaaaccga 1380
acttcaaagt tcttaacctg gagaacaact ggggtgacat tagcgacgcg atccataaat 1440
cttccccgca atgcaccacc attaacccgg ctctgcagct gatctctccg tctaacgatc 1500
cgtgggtagt taacaaagtg tctcaaatca gcccggacat gggtatcctg aaatttaaat 1560
ctagcaaata gtgactcgag 1580

<210> SEQ ID NO 26
<211> LENGTH: 1586
<212> TYPE: DNA
<213> ORGANISM: Artificial Sequence
<220> FEATURE:
<223> OTHER INFORMATION: Nucleotide sequence of Algo VH-CH-deBouganin

<400> SEQUENCE: 26

```
gaattcctgc aggtctatgg aacgataaat gcccatgaaa attctatttc aaggagacag     60

tcataatgaa atacctattg cctacggcag ccgctggatt gttattactc gctgcccaac    120

cagcgatggc ggaagtacag ctgcagcagt ccggtccggg tctggttcag ccgggtggta    180

gcgttcgtat tagctgcgcg gcgagcggtt acaccttcac cgcgtacggt atgaactggg    240

ttcgtcaggc tccgggtaaa ggtttggaat ggatgggttg gatcaacacc tataccggtg    300

agtctaccta cgctgatagc ttcaaaggcc gtttcgaatt tagccttgac actcacaaca    360

gctctgcgta cctgcagatt cagtctctgc gtgaagagga cactgcggtt tactactgcg    420

ctcgtttcgc gatccagggt gactattggg gtcagggtac tctggttacc gttagcagcg    480

ctagcactaa gggcccgtcc gttttcccac tggctccgtc ttctaaaagc acttctggtg    540

gtaccgcggc tctgggttgc cttgttaaag actacttccc tgaaccggtc accgttagct    600

ggaactccgg tgcgttgacc tctggtgttc acaccttccc agcggttctg cagtctagcg    660

gtctgtatag cctgagctct gtagttaccg ttccgtcttc tagcctgggt acgcagacct    720

acatctgcaa cgtgaaccac aaaccgagca acactaaagt ggataaaaaa gttgaaccga    780

agtcttgcac ccgtcaccgt cagccgcgtg gttgggaaca gaaatataac accgtatctt    840

ttaacctggg tgaggcgtat gaatacccga ccttcatcca ggacctgcgt aatgaacttg    900

ctaaaggtac ccctgtttgc cagctgcctg tgaccctgca gaccatcgct gatgataaac    960

gtttcgttct ggttgacatt accaccacct ccaaaaaaac cgttaaagtc gcgatcgatg   1020

tgaccgacgt ttacgtggta ggttaccagg ataaatggga cggtaaagat cgtgcggttt   1080

tcctggacaa agttccgacc gtagcgactt ctaaactgtt cccaggtgtg accaaccgtg   1140

tgaccctgac cttcgacggc agctatcaga aactggttaa cgcggccaaa gctgatcgta   1200

aagctctcga actgggtgtt aacaaactgg agttcagcat tgaagctatc cacggtaaaa   1260

ccatcaacgg tcaagaagca gctaaattct tcctgatcgt gatccagatg gttagcgaag   1320

cagcgcgttt taaatacatt gaaaccgaag tagttgatcg tggtctgtat ggtagcttca   1380

aaccgaactt caaagttctt aacctggaga acaactgggg tgacattagc gacgcgatcc   1440

ataaatcttc cccgcaatgc accaccatta acccggctct gcagctgatc tctccgtcta   1500

acgatccgtg ggtagttaac aaagtgtctc aaatcagccc ggacatgggt atcctgaaat   1560

ttaaatctag caaatagtga ctcgag                                        1586
```

<210> SEQ ID NO 27
<211> LENGTH: 1580
<212> TYPE: DNA
<213> ORGANISM: Artificial Sequence
<220> FEATURE:
<223> OTHER INFORMATION: Nucleotide sequence of WT VH-CH-deBouganin

<400> SEQUENCE: 27

```
ctgcaggtct atggaacgat aaatgcccat gaaaattcta tttcaaggag acagtcataa     60

tgaaatacct attgcctacg gcagccgctg gattgttatt actcgctgcc caaccagcga    120

tggcggaagt acagctggtt cagtccggcc cgggtcttgt tcaaccgggt ggttccgttc    180
```

```
gtatctcttg cgctgcttct ggttacacgt tcaccaacta cggcatgaac tgggtcaaac    240
aggctccggg taaaggcctg gaatggatgg gctggatcaa cacctacacc ggtgaatcca    300
cctacgctga ctccttcaaa ggtcgcttca ctttctccct cgacacaagt gctagtgctg    360
catacctcca aatcaactcg ctgcgtgcag aggatacagc agtctattac tgcgcccgtt    420
tcgctatcaa aggtgactac tggggtcaag gcacgctgct gaccgtttcc tcggctagca    480
ccaaaggccc atcggtcttc cccctggcac cctcctccaa gagcacctct gggggcacag    540
cggccctggg ctgcctggtc aaggactact tccccgaacc ggtgacggtg tcgtggaact    600
caggcgccct gaccagcggc gtgcacacct tcccggctgt cctacagtcc tcaggactct    660
actccctcag cagcgtggtg accgtgccct ccagcagctt gggcacccag acctacatct    720
gcaacgtgaa tcacaagccc agcaacacca aggtggacaa gaaagttgag cccaaatctt    780
gtacccgtca ccgtcagccg cgtggttggg aacagctcta taacaccgta tcttttaacc    840
tgggtgaggc gtatgaatac ccgaccttca tccaggacct gcgtaatgaa cttgctaaag    900
gtacccctgt ttgccagctg cctgtgaccc tgcagaccat cgctgatgat aaacgtttcg    960
ttctggttga cattaccacc acctccaaaa aaaccgttaa agtcgcgatc gatgtgaccg   1020
acgtttacgt ggtaggttac caggataaat gggacggtaa agatcgtgcg gttttcctgg   1080
acaaagttcc gaccgtagcg acttctaaac tgttcccagg tgtgaccaac cgtgtgaccc   1140
tgaccttcga cggcagctat cagaaactgg ttaacgcggc caaagctgat cgtaaagctc   1200
tcgaactggg tgttaacaaa ctggagttca gcattgaagc tatccacggt aaaaccatca   1260
acggtcaaga agcagctaaa ttcttcctga tcgtgatcca gatggttagc gaagcagcgc   1320
gttttaaata cattgaaacc gaagtagttg atcgtggtct gtatggtagc ttcaaaccga   1380
acttcaaagt tcttaacctg gagaacaact ggggtgacat tagcgacgcg atccataaat   1440
cttccccgca atgcaccacc attaacccgg ctctgcagct gatctctccg tctaacgatc   1500
cgtgggtagt taacaaagtg tctcaaatca gcccggacat gggtatcctg aaatttaaat   1560
ctagcaaata gtgactcgag                                               1580
```

```
<210> SEQ ID NO 28
<211> LENGTH: 1580
<212> TYPE: DNA
<213> ORGANISM: Artificial Sequence
<220> FEATURE:
<223> OTHER INFORMATION: Nucleotide sequence of DI VL-CL-deBouganin

<400> SEQUENCE: 28

ctgcaggtct atggaacgat aaatgcccat gaaaattcta tttcaaggag acagtcataa     60
tgaaatacct tctgccgacc gctgccgctg gtctgctgct gttggctgct caaccggcta    120
tggcagacat ccagatgacc cagtccccgt ctagcctgag cgcaagcgtt ggtgaccgtg    180
tgaccatcac ctgccgtagc actaaatccc tgctgcactc taacggcatc acctacctgt    240
attggtacca acagaaaccg ggtaaagctc cgaaactgct gatctaccag atgtctaacc    300
tggctagcgg cgttccttct cgtttttctt ctagcggtag cggtactgac ttcaccctga    360
ccattagctc tctgcagcct gaagactttg cgacctacta ttgcgctcag aaccttgaaa    420
tcccgcgtac cttcggcacc ggtaccaaag ttgaaatcaa gcgtaccgtt gcggctccgt    480
ctgttttcat cttcccacct agcgatgaac agcttaaatc tggtactgct agcgtagttt    540
gcctgcttaa caacttctac cctcgtgaag ctaaagttca gtggaaagtt gacaacgctc    600
```

-continued

```
tgcagtctgg taactctcag gaatctgtga ccgaacagga tagcaaagat agcacctata    660
gcctgtctag caccctgacc cttagcaagg cggactatga aaaacacaaa gtttacgctt    720
gcgaggtgac ccaccaaggt ctgtcttctc cggtgactaa atcctttaac cgtggcgaat    780
gcacccgtca ccgtcagccg cgtggttggg aacagaaata taacaccgta tcttttaacc    840
tgggtgaggc gtatgaatac ccgaccttca tccaggacct gcgtaatgaa cttgctaaag    900
gtacccctgt ttgccagctg cctgtgaccc tgcagaccat cgctgatgat aaacgtttcg    960
ttctggttga cattaccacc acctccaaaa aaaccgttaa agtcgcgatc gatgtgaccg   1020
acgtttacgt ggtaggttac caggataaat gggacggtaa agatcgtgcg gttttcctgg   1080
acaaagttcc gaccgtagcg acttctaaac tgttcccagg tgtgaccaac cgtgtgaccc   1140
tgaccttcga cggcagctat cagaaactgg ttaacgcggc caaagctgat cgtaaagctc   1200
tcgaactggg tgttaacaaa ctggagttca gcattgaagc tatccacggt aaaaccatca   1260
acggtcaaga agcagctaaa ttcttcctga tcgtgatcca gatggttagc gaagcagcgc   1320
gttttaaata cattgaaacc gaagtagttg atcgtggtct gtatggtagc ttcaaaccga   1380
acttcaaagt tcttaacctg gagaacaact ggggtgacat tagcgacgcg atccataaat   1440
cttccccgca atgcaccacc attaacccgg ctctgcagct gatctctccg tctaacgatc   1500
cgtgggtagt taacaaagtg tctcaaatca gcccggacat gggtatcctg aaatttaaat   1560
ctagcaaata gtgactcgag                                                1580
```

<210> SEQ ID NO 29
<211> LENGTH: 1592
<212> TYPE: DNA
<213> ORGANISM: Artificial Sequence
<220> FEATURE:
<223> OTHER INFORMATION: Nucleotide sequence of Algo VL-CL-deBouganin

<400> SEQUENCE: 29

```
tctagagtcg acctgcaggt ctatggaacg ataaatgccc atgaaaattc tatttcaagg     60
agacagtcat aatgaaatac cttctgccga ccgctgccgc tggtctgctg ctgttggctg    120
ctcaaccggc tatggcagac atccagatga cccagtcccc gtctagcctg agcgcaagcg    180
ttggtgaccg tgtgaccatc acctgcaaaa gcactaaatc cctgctgcac tctaacggca    240
tcacctacct gtattggtac caacagaaac cgggttctgc tccgaaactg ctgatctacc    300
agatgtctca cctggctagc ggcgttcctt ctcgtttttc ttctagcggt agcggtactg    360
acttcaccct gaccattagc tctctgcagc ctgaagactt tgcgacctac tattgcgctc    420
agaaccttga aatcccgcgt accttcggcc agggtaccaa agttgaaatc aagcgtaccg    480
ttgcggctcc gtctgttttc atcttcccac ctagcgatga acagcttaaa tctggtactg    540
ctagcgtagt ttgcctgctt aacaacttct accctcgtga agctaaagtt cagtggaaag    600
ttgacaacgc tctgcagtct ggtaactctc aggaatctgt gaccgaacag gatagcaaag    660
atagcaccta tagcctgtct agcaccctga cccttagcaa ggcggactat gaaaaacaca    720
aagtttacgc ttgcgaggtg acccaccaag gtctgtcttc tccggtgact aaatccttta    780
accgtggcga atgcacccgt caccgtcagc cgcgtggttg ggaacagaaa tataacaccg    840
tatcttttaa cctgggtgag gcgtatgaat acccgacctt catccaggac ctgcgtaatg    900
aacttgctaa aggtacccct gtttgccagc tgcctgtgac cctgcagacc atcgctgatg    960
ataaacgttt cgttctggtt gacattacca ccacctccaa aaaaaccgtt aaagtcgcga   1020
tcgatgtgac cgacgtttac gtggtaggtt accaggataa atgggacggt aaagatcgtg   1080
```

```
cggttttcct ggacaaagtt ccgaccgtag cgacttctaa actgttccca ggtgtgacca   1140

accgtgtgac cctgaccttc gacggcagct atcagaaact ggttaacgcg gccaaagctg   1200

atcgtaaagc tctcgaactg ggtgttaaca aactggagtt cagcattgaa gctatccacg   1260

gtaaaaccat caacggtcaa gaagcagcta aattcttcct gatcgtgatc cagatggtta   1320

gcgaagcagc gcgttttaaa tacattgaaa ccgaagtagt tgatcgtggt ctgtatggta   1380

gcttcaaacc gaacttcaaa gttcttaacc tggagaacaa ctggggtgac attagcgacg   1440

cgatccataa atcttccccg caatgcacca ccattaaccc ggctctgcag ctgatctctc   1500

cgtctaacga tccgtgggta gttaacaaag tgtctcaaat cagcccggac atgggtatcc   1560

tgaaatttaa atctagcaaa tagtgactcg ag                                 1592
```

<210> SEQ ID NO 30
<211> LENGTH: 1598
<212> TYPE: DNA
<213> ORGANISM: Artificial Sequence
<220> FEATURE:
<223> OTHER INFORMATION: Nucleotide sequence of WT VL-CL-deBouganin

<400> SEQUENCE: 30

```
ctgcaggtct atggaacgat aaatgcccat gaaaattcta tttcaaggag acagtcataa     60

tgaaatacct attgcctacg gcagccgctg gattgttatt actcgctgcc caaccagcga    120

tggcgcacca tcatcaccat cacgatatcc agatgaccca gtccccgtcc tccctgagtg    180

cttctgttgg tgaccgtgtt accatcacct gccgttccac caaatccctc ctgcactcca    240

acggtatcac ctacctttat tggtatcaac agaaaccggg taaagctccg aaacttctga    300

tctaccagat gtccaacctg gcttccggtg ttccgtctcg tttctccagt tctggttctg    360

gtaccgactt caccctgacc atctcttctc tgcagccgga agacttcgct acctactact    420

gcgctcagaa cctggaaatc ccgcgtacct tcggtcaggg taccaaagtt gaacttaagc    480

gcactgtggc tgcaccatct gtcttcatct tcccgccatc tgatgagcag ttgaaatctg    540

gaactgcctc tgttgtgtgc ctgctgaata acttctatcc cagagaggcc aaagtacagt    600

ggaaggtgga taacgccctc caatcgggta actcccagga gagtgtcaca gagcaggaca    660

gcaaggacag cacctacagc ctcagcagca ccctgacgct gagcaaagca gactacgaga    720

aacacaaagt ctacgcctgc gaagtcaccc atcagggcct gagctcgccc gtcacaaaga    780

gcttcaacag gggagagtgt acccgtcacc gtcagccgcg tggttgggaa cagctctata    840

acaccgtatc ttttaacctg ggtgaggcgt atgaataccc gaccttcatc caggacctgc    900

gtaatgaact tgctaaaggt accccctgttt gccagctgcc tgtgaccctg cagaccatcg    960

ctgatgataa acgtttcgtt ctggttgaca ttaccaccac ctccaaaaaa accgttaaag   1020

tcgcgatcga tgtgaccgac gtttacgtgg taggttacca ggataaatgg gacggtaaag   1080

atcgtgcggt tttcctggac aaagttccga ccgtagcgac ttctaaactg ttcccaggtg   1140

tgaccaaccg tgtgaccctg accttcgacg gcagctatca gaaactggtt aacgcggcca   1200

aagctgatcg taaagctctc gaactgggtg ttaacaaact ggagttcagc attgaagcta   1260

tccacggtaa aaccatcaac ggtcaagaag cagctaaatt cttcctgatc gtgatccaga   1320

tggttagcga agcagcgcgt tttaaataca ttgaaaccga agtagttgat cgtggtctgt   1380

atggtagctt caaaccgaac ttcaaagttc ttaacctgga gaacaactgg ggtgacatta   1440

gcgacgcgat ccataaatct tccccgcaat gcaccaccat taacccggct ctgcagctga   1500
```

```
tctctccgtc taacgatccg tgggtagtta acaaagtgtc tcaaatcagc ccggacatgg   1560

gtatcctgaa atttaaatct agcaaatagt gactcgag                           1598


<210> SEQ ID NO 31
<211> LENGTH: 219
<212> TYPE: PRT
<213> ORGANISM: Artificial Sequence
<220> FEATURE:
<223> OTHER INFORMATION: Algo VH (CDRsWT) -CH

<400> SEQUENCE: 31

Glu Val Gln Leu Gln Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
65                  70                  75                  80

Leu Gln Ile Gln Ser Leu Arg Glu Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys
    210                 215


<210> SEQ ID NO 32
<211> LENGTH: 219
<212> TYPE: PRT
<213> ORGANISM: Artificial Sequence
<220> FEATURE:
<223> OTHER INFORMATION: Algo VH(CDRsWT + Treg) - CH

<400> SEQUENCE: 32

Glu Val Gln Leu Gln Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
```

```
65                  70                  75                  80

Leu Gln Met Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys
    210                 215


<210> SEQ ID NO 33
<211> LENGTH: 250
<212> TYPE: PRT
<213> ORGANISM: Artificial Sequence
<220> FEATURE:
<223> OTHER INFORMATION: deBouganin 2

<400> SEQUENCE: 33

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val His Ser Ala Glu Val Asp Arg Lys Asp Leu
        115                 120                 125

Glu Leu Gly Val Asn Lys Leu Glu Phe Ser Ile Glu Ala Ile His Gly
    130                 135                 140

Lys Thr Ile Asn Gly Gln Glu Ile Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu His Gly Ser Phe Lys Pro Asp Phe Lys Val Leu
            180                 185                 190

Asp Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
```

```
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250


<210> SEQ ID NO 34
<211> LENGTH: 481
<212> TYPE: PRT
<213> ORGANISM: Artificial Sequence
<220> FEATURE:
<223> OTHER INFORMATION: DI VH-CH-deBouganin 3

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ala Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
```

-continued

```
                325                 330                 335

Val Thr Leu Thr Phe Asp Gly Ser Tyr Gln Lys Leu Val His Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 35
<211> LENGTH: 481
<212> TYPE: PRT
<213> ORGANISM: Artificial Sequence
<220> FEATURE:
<223> OTHER INFORMATION: DI VL-CL-deBouganin 3

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Thr Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 36
<211> LENGTH: 481
<212> TYPE: PRT
<213> ORGANISM: Artificial Sequence
<220> FEATURE:
<223> OTHER INFORMATION: Algo VH-CH-deBouganin 3

<400> SEQUENCE: 36

Glu Val Gln Leu Gln Gln Ser Gly Pro Gly Leu Val Gln Pro Gly Gly
1               5                   10                  15

Ser Val Arg Ile Ser Cys Ala Ala Ser Gly Tyr Thr Phe Thr Ala Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
65                  70                  75                  80
```

```
Leu Gln Ile Gln Ser Leu Arg Glu Glu Asp Thr Ala Val Tyr Tyr Cys
                85                  90                  95

Ala Arg Phe Ala Ile Gln Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys

<210> SEQ ID NO 37
```

<211> LENGTH: 481
<212> TYPE: PRT
<213> ORGANISM: Artificial Sequence
<220> FEATURE:
<223> OTHER INFORMATION: Algo VL-CL-deBouganin 3

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Lys Ser Thr Lys Ser Leu Leu His Ser
            20                  25                  30

Asn Gly Ile Thr Tyr Leu Tyr Trp Tyr Gln Gln Lys Pro Gly Ser Ala
        35                  40                  45

Pro Lys Leu Leu Ile Tyr Gln Met Ser His Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380
```

```
Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 38
<211> LENGTH: 481
<212> TYPE: PRT
<213> ORGANISM: Artificial Sequence
<220> FEATURE:
<223> OTHER INFORMATION: Algo VH(CDRsWT)-CH-deBouganin

<400> SEQUENCE: 38

Glu Val Gln Leu Gln Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
65                  70                  75                  80

Leu Gln Ile Gln Ser Leu Arg Glu Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255
```

```
Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val Asn Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 39
<211> LENGTH: 481
<212> TYPE: PRT
<213> ORGANISM: Artificial Sequence
<220> FEATURE:
<223> OTHER INFORMATION: Algo VH(CDRsWT)-CH-deBouganin3

<400> SEQUENCE: 39

Glu Val Gln Leu Gln Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
65                  70                  75                  80

Leu Gln Ile Gln Ser Leu Arg Glu Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
```

```
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 40
<211> LENGTH: 481
<212> TYPE: PRT
<213> ORGANISM: Artificial Sequence
<220> FEATURE:
<223> OTHER INFORMATION: Algo VH(CDRsWT + Treg)-CH-deBouganin

<400> SEQUENCE: 40

Glu Val Gln Leu Gln Gln Ser Gly Pro Gly Leu Val Gln Pro Gly Gly
1               5                   10                  15
```

-continued

```
Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
65                  70                  75                  80

Leu Gln Met Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val Asn Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430
```

```
Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 41
<211> LENGTH: 481
<212> TYPE: PRT
<213> ORGANISM: Artificial Sequence
<220> FEATURE:
<223> OTHER INFORMATION: Algo VH(CDRsWT+Treg)-CH-deBouganin3

<400> SEQUENCE: 41

Glu Val Gln Leu Gln Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
65                  70                  75                  80

Leu Gln Met Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
```

```
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 42
<211> LENGTH: 250
<212> TYPE: PRT
<213> ORGANISM: Artificial Sequence
<220> FEATURE:
<223> OTHER INFORMATION: deBouganin 3

<400> SEQUENCE: 42

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val His Ala Ala Lys Ala Asp Arg Lys Ala Leu
        115                 120                 125

Glu Leu Gly Val Asn Lys Leu Glu Phe Ser Ile Glu Ala Ile His Gly
    130                 135                 140

Lys Thr Ile Asn Gly Gln Glu Ala Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190
```

```
Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250


<210> SEQ ID NO 43
<211> LENGTH: 250
<212> TYPE: PRT
<213> ORGANISM: Artificial Sequence
<220> FEATURE:
<223> OTHER INFORMATION: deBouganin 4

<400> SEQUENCE: 43

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val His Ala Ala Lys Val Asp Arg Lys Asp Leu
        115                 120                 125

Glu Leu Gly Val Asn Lys Leu Glu Phe Ser Ile Glu Ala Ile His Gly
    130                 135                 140

Lys Thr Ile Asn Gly Gln Glu Ile Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250


<210> SEQ ID NO 44
<211> LENGTH: 481
<212> TYPE: PRT
<213> ORGANISM: Artificial Sequence
<220> FEATURE:
<223> OTHER INFORMATION: DI VH-CH-deBouganin 4
```

<400> SEQUENCE: 44

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ala Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Val Asp Arg Lys Asp Leu Glu Leu Gly Val Asn Lys Leu Glu Phe
        355                 360                 365

Ser Ile Glu Ala Ile His Gly Lys Thr Ile Asn Gly Gln Glu Ile Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415
```

```
Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 45
<211> LENGTH: 481
<212> TYPE: PRT
<213> ORGANISM: Artificial Sequence
<220> FEATURE:
<223> OTHER INFORMATION: DI VL-CL-deBouganin4

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Thr Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285
```

```
Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Val Asp Arg Lys Asp Leu Glu Leu Gly Val Asn Lys Leu Glu Phe
        355                 360                 365

Ser Ile Glu Ala Ile His Gly Lys Thr Ile Asn Gly Gln Glu Ile Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 46
<211> LENGTH: 481
<212> TYPE: PRT
<213> ORGANISM: Artificial Sequence
<220> FEATURE:
<223> OTHER INFORMATION: Algo VH-CH-deBouganin 4

<400> SEQUENCE: 46

Glu Val Gln Leu Gln Gln Ser Gly Pro Gly Leu Val Gln Pro Gly Gly
1               5                   10                  15

Ser Val Arg Ile Ser Cys Ala Ala Ser Gly Tyr Thr Phe Thr Ala Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
65                  70                  75                  80

Leu Gln Ile Gln Ser Leu Arg Glu Glu Asp Thr Ala Val Tyr Tyr Cys
                85                  90                  95

Ala Arg Phe Ala Ile Gln Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
```

```
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Val Asp Arg Lys Asp Leu Glu Leu Gly Val Asn Lys Leu Glu Phe
        355                 360                 365

Ser Ile Glu Ala Ile His Gly Lys Thr Ile Asn Gly Gln Glu Ile Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 47
<211> LENGTH: 481
<212> TYPE: PRT
<213> ORGANISM: Artificial Sequence
<220> FEATURE:
<223> OTHER INFORMATION: Algo VL-CL-deBouganin 4

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ser Thr Lys Ser Leu Leu His Ser
            20                  25                  30

Asn Gly Ile Thr Tyr Leu Tyr Trp Tyr Gln Gln Lys Pro Gly Ser Ala
        35                  40                  45
```

-continued

```
Pro Lys Leu Leu Ile Tyr Gln Met Ser His Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Val Asp Arg Lys Asp Leu Glu Leu Gly Val Asn Lys Leu Glu Phe
        355                 360                 365

Ser Ile Glu Ala Ile His Gly Lys Thr Ile Asn Gly Gln Glu Ile Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460
```

-continued

```
Val Ser Gln Ile Ser Pro Asp Met Gly Ile Leu Lys Phe Lys Ser Ser
465                 470                 475                 480

Lys


<210> SEQ ID NO 48
<211> LENGTH: 481
<212> TYPE: PRT
<213> ORGANISM: Artificial Sequence
<220> FEATURE:
<223> OTHER INFORMATION: Algo VH(CDRsWT)-CH-deBouganin4

<400> SEQUENCE: 48

Glu Val Gln Leu Gln Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
65                  70                  75                  80

Leu Gln Ile Gln Ser Leu Arg Glu Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
```

-continued

```
            340                 345                 350

Lys Val Asp Arg Lys Asp Leu Glu Leu Gly Val Asn Lys Leu Glu Phe
        355                 360                 365

Ser Ile Glu Ala Ile His Gly Lys Thr Ile Asn Gly Gln Glu Ile Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 49
<211> LENGTH: 481
<212> TYPE: PRT
<213> ORGANISM: Artificial Sequence
<220> FEATURE:
<223> OTHER INFORMATION: Algo VH(CDRsWT +Treg)-CH-deBouganin4

<400> SEQUENCE: 49

Glu Val Gln Leu Gln Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Glu Phe Ser Leu Asp Thr His Asn Ser Ser Ala Tyr
65                  70                  75                  80

Leu Gln Met Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220
```

```
Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Val Asp Arg Lys Asp Leu Glu Leu Gly Val Asn Lys Leu Glu Phe
        355                 360                 365

Ser Ile Glu Ala Ile His Gly Lys Thr Ile Asn Gly Gln Glu Ile Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 50
<211> LENGTH: 481
<212> TYPE: PRT
<213> ORGANISM: Artificial Sequence
<220> FEATURE:
<223> OTHER INFORMATION: WT VH-CH-deBouganin 3

<400> SEQUENCE: 50

Glu Val Gln Leu Val Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Thr Phe Ser Leu Asp Thr Ser Ala Ser Ala Ala Tyr
65                  70                  75                  80

Leu Gln Ile Asn Ser Leu Arg Ala Glu Asp Thr Ala Val Tyr Tyr Cys
                85                  90                  95
```

-continued

```
Ala Arg Phe Ala Ile Lys Gly Asp Tyr Trp Gly Gln Gly Thr Leu Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys
```

<210> SEQ ID NO 51
<211> LENGTH: 481
<212> TYPE: PRT
<213> ORGANISM: Artificial Sequence
<220> FEATURE:
<223> OTHER INFORMATION: WT VH-CH-deBouganin4

<400> SEQUENCE: 51

Glu Val Gln Leu Val Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Glu Trp Met
        35                  40                  45

Gly Trp Ile Asn Thr Tyr Thr Gly Glu Ser Thr Tyr Ala Asp Ser Phe
    50                  55                  60

Lys Gly Arg Phe Thr Phe Ser Leu Asp Thr Ser Ala Ser Ala Ala Tyr
65                  70                  75                  80

Leu Gln Ile Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Val Asp Arg Lys Asp Leu Glu Leu Gly Val Asn Lys Leu Glu Phe
        355                 360                 365

Ser Ile Glu Ala Ile His Gly Lys Thr Ile Asn Gly Gln Glu Ile Ala
    370                 375                 380

Lys Phe Phe Leu Ile Val Ile Gln Met Val Ser Glu Ala Ala Arg Phe
385                 390                 395                 400

```
Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 52
<211> LENGTH: 481
<212> TYPE: PRT
<213> ORGANISM: Artificial Sequence
<220> FEATURE:
<223> OTHER INFORMATION: WT VL-CL-deBouganin 3

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270
```

```
Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Ala Asp Arg Lys Ala Leu Glu Leu Gly Val Asn Lys Leu Glu Phe
        355                 360                 365

Ser Ile Glu Ala Ile His Gly Lys Thr Ile Asn Gly Gln Glu Ala Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys


<210> SEQ ID NO 53
<211> LENGTH: 481
<212> TYPE: PRT
<213> ORGANISM: Artificial Sequence
<220> FEATURE:
<223> OTHER INFORMATION: WT VL-CL-deBouganin 4

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

-continued

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Thr Arg His Arg Gln
    210                 215                 220

Pro Arg Gly Trp Glu Gln Lys Tyr Asn Thr Val Ser Phe Asn Leu Gly
225                 230                 235                 240

Glu Ala Tyr Glu Tyr Pro Thr Phe Ile Gln Asp Leu Arg Asn Glu Leu
                245                 250                 255

Ala Lys Gly Thr Pro Val Cys Gln Leu Pro Val Thr Leu Gln Thr Ile
            260                 265                 270

Ala Asp Asp Lys Arg Phe Val Leu Val Asp Ile Thr Thr Thr Ser Lys
        275                 280                 285

Lys Thr Val Lys Val Ala Ile Asp Val Thr Asp Val Tyr Val Val Gly
    290                 295                 300

Tyr Gln Asp Lys Trp Asp Gly Lys Asp Arg Ala Val Phe Leu Asp Lys
305                 310                 315                 320

Val Pro Thr Val Ala Thr Ser Lys Leu Phe Pro Gly Val Thr Asn Arg
                325                 330                 335

Val Thr Leu Thr Phe Asp Gly Ser Tyr Gln Lys Leu Val His Ala Ala
            340                 345                 350

Lys Val Asp Arg Lys Asp Leu Glu Leu Gly Val Asn Lys Leu Glu Phe
        355                 360                 365

Ser Ile Glu Ala Ile His Gly Lys Thr Ile Asn Gly Gln Glu Ile Ala
    370                 375                 380

Lys Phe Phe Leu Ile Val Ile Gln Met Val Ser Glu Ala Ala Arg Phe
385                 390                 395                 400

Lys Tyr Ile Glu Thr Glu Val Val Asp Arg Gly Leu Tyr Gly Ser Phe
                405                 410                 415

Lys Pro Asn Phe Lys Val Leu Asn Leu Glu Asn Asn Trp Gly Asp Ile
            420                 425                 430

Ser Asp Ala Ile His Lys Ser Ser Pro Gln Cys Thr Thr Ile Asn Pro
        435                 440                 445

Ala Leu Gln Leu Ile Ser Pro Ser Asn Asp Pro Trp Val Val Asn Lys
    450                 455                 460

Val Ser Gln Ile Ser Pro Asp Met Gly Ile Leu Lys Phe Lys Ser Ser
465                 470                 475                 480

Lys
```